United States Patent
Cook et al.

(10) Patent No.: US 11,976,333 B2
(45) Date of Patent: *May 7, 2024

(54) METHODS OF DIAGNOSING AND TREATING PATIENTS WITH CUTANEOUS SQUAMOUS CELL CARCINOMA

(71) Applicant: Castle Biosciences, Inc., Friendswood, TX (US)

(72) Inventors: Robert Willis Cook, Houston, TX (US); Kyle R. Covington, Missouri City, TX (US); Derek Maetzold, Friendswood, TX (US); Sarah J Kurley, Friendswood, TX (US)

(73) Assignee: CASTLE BIOSCIENCES, INC., Friendswood, TX (US)

( * ) Notice: Subject to any disclaimer, the term of this patent is extended or adjusted under 35 U.S.C. 154(b) by 605 days.

This patent is subject to a terminal disclaimer.

(21) Appl. No.: 16/993,401

(22) Filed: Aug. 14, 2020

(65) Prior Publication Data

US 2021/0238688 A1 Aug. 5, 2021

Related U.S. Application Data

(63) Continuation-in-part of application No. 16/779,515, filed on Jan. 31, 2020.

(51) Int. Cl.
 *C12Q 1/6886* (2018.01)
(52) U.S. Cl.
 CPC ..... *C12Q 1/6886* (2013.01); *C12Q 2600/106* (2013.01); *C12Q 2600/118* (2013.01); *C12Q 2600/158* (2013.01)
(58) Field of Classification Search
 CPC ............ C12Q 1/6886; C12Q 2600/106; C12Q 2600/118; C12Q 2600/158
 See application file for complete search history.

(56) References Cited

U.S. PATENT DOCUMENTS

| | | |
|---|---|---|
| 2011/0124525 A1 | 5/2011 | Harbour |
| 2013/0224192 A1 | 8/2013 | Lidereau et al. |
| 2015/0152474 A1 | 6/2015 | Pawloski et al. |
| 2016/0058777 A1 | 3/2016 | Bittner et al. |
| 2019/0330625 A1 | 10/2019 | Sampath et al. |
| 2020/0149115 A1 | 5/2020 | Dobak et al. |

FOREIGN PATENT DOCUMENTS

| | | |
|---|---|---|
| WO | WO 2017/210662 | 12/2017 |
| WO | WO 2019/161126 | 8/2019 |
| WO | WO 2019/213321 | 11/2019 |
| WO | WO 2021/155377 | 8/2021 |

OTHER PUBLICATIONS

Thompson et. al., JAMA Dermatol., vol. 152(4), pp. 419-428, publ. 2016 (Year: 2016).*
Hameetman et al., "Molecular profiling of cutaneous squamous cell carcinomas and actinic keratoses from organ transplant recipients." BMC Cancer. 13:58 pp. 1-16 (Feb. 2013).
International Search Report from International application No. PCT/US2019/30282; dated Sep. 9, 2019, pp. 1-4.
Jambusaria-Pahlajani et al., "Evaluation of AJCC Tumor Staging for Cutaneous Squamous Cell Carcinoma and a Proposed Alternative Tumor Staging System" JAMA Dermatol. 149:402-10 (Apr. 2013).
Karia et al., "Cutaneous squamous cell carcinoma: estimated incidence of disease, nodal metastasis, and deaths from disease in the United States, 2012" J. Am. Acad. Dermatol. 68(6):957-66 (Jun. 2013).—Abstract only submitted.
Karia et al., "Evaluation of American Joint Committee on Cancer, International Union Against Cancer, and Brigham and Women's Hospital tumor staging for cutaneous squamous cell carcinoma" J. Clin. Oncol. 32(4):327-34 (Feb. 2014).
Karia et al., "Comparison of Tumor Classifications for Cutaneous Squamous Cell Carcinoma of the Head and Neck in the 7th vs 8th Edition of the AJCC Cancer Staging Manual" JAMA Dermatol. 154(2):175-81 (Feb. 2018).
NCCN Guidelines@ Squamous Cell Skin Cancer Version 2.2018, updated Oct. 5, 2017, available on the World Wide Web at NCCN.org.
Ruiz et al., "Performance of the American Joint Committee on Cancer Staging Manual, 8th Edition vs the Brigham and Women's Hospital Tumor Classification System for Cutaneous Squamous Cell Carcinoma" JAMA Dermatol. 155(7):819-25 (Jul. 2019).
Zilberg et al., "Is high-risk cutaneous squamous cell carcinoma of the head and neck a suitable candidate for current targeted therapies?" Journal of Clinical Pathology, 73(1):17-22 (Jan. 2020; Epub Jul. 12, 2019).
Farberg et al., "Integrating gene expression profiling into NCCN high-risk cutaneous squamous cell carcinoma magagement recommendations: impact on patient management" Current Medical Research and Opinion, 36(8):1301-07 (May 18, 2020).
Kunz, "Microarray Technology in Dermatology" Seminars in Cutaneous Medicine and Surgery 27:16-24 (2008).
Wysong et al., "Validation of a 40-gene expression profile test to predict metastatic risk localized high-risk cutaneous squamous cell carcinoma" J. American Academy of Dermatology 84(2):361-69 (Apr. 25, 2020).
International Search Report for International Application No. PCT/US2021/016097; dated Jul. 14, 2021, pp. 1-3.
International Search Report for International Application No. PCT/US2021/045981; dated Dec. 1, 2021, pp. 1-2.
International Search Report for International Application No. PCT/US2021/046105; dated Dec. 21, 2021, pp. 1-2.
Alam et. al., J. Amer. Acad. Dermatol., vol. 78(3), pp. 1-40, publ. 2018 (Year: 2018).
Mitsui et al., J. Investig. Derm., vol. 134, pp. 1418-1427, publ. 2014 (Year: 2014).

* cited by examiner

*Primary Examiner* — Sarah Pihonak

(74) *Attorney, Agent, or Firm* — McDonnell Boehnen Hulbert & Berghoff LLP

(57) ABSTRACT

The present disclosure relates to methods for predicting the risk of recurrence and/or metastasis, or both in primary cutaneous squamous cell carcinoma (cSCC).

17 Claims, 23 Drawing Sheets

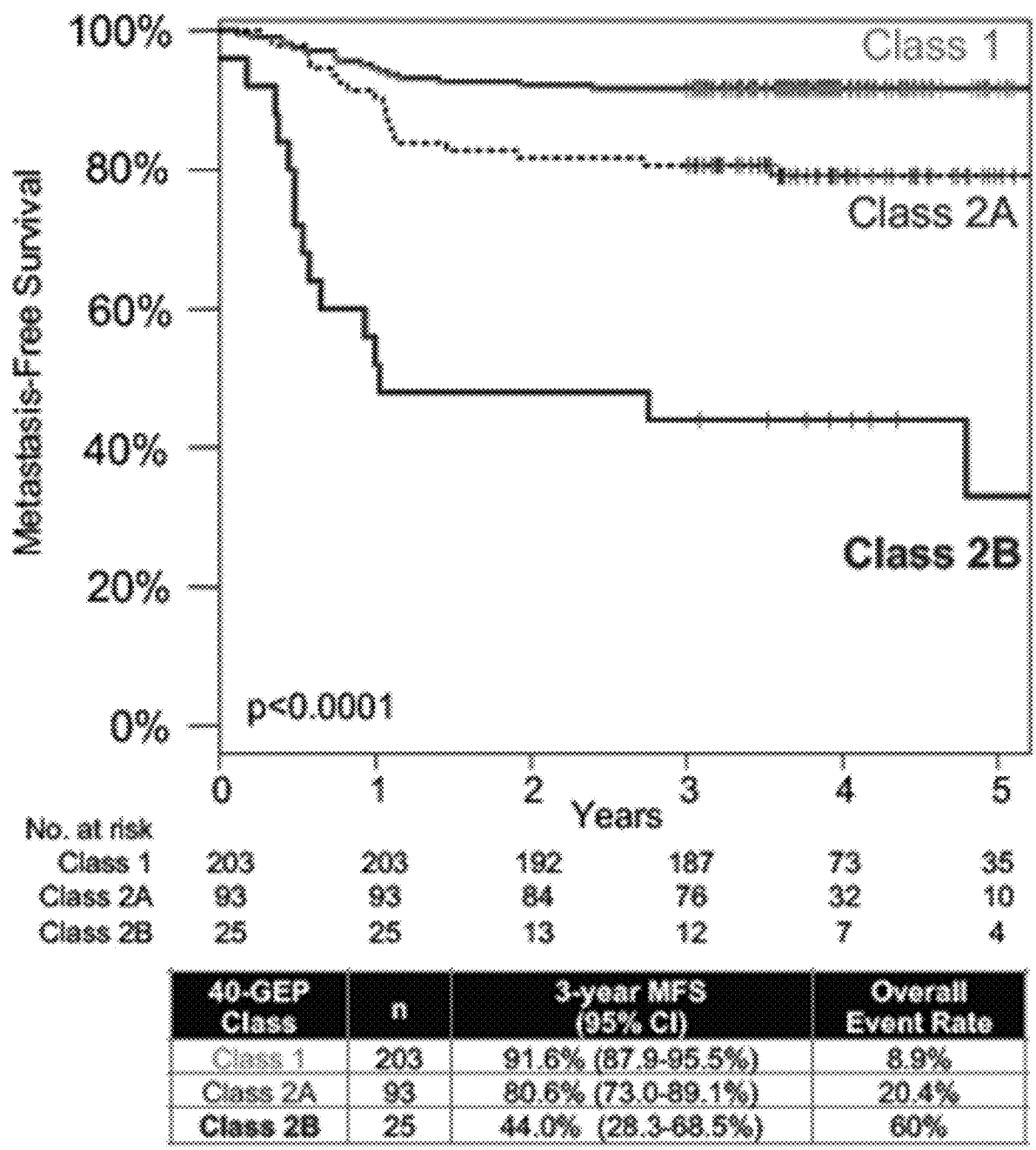

FIG.7

| Feature | All (n=321) | NonMet (n=269) | Regional/distant met (n=52) | p value |
|---|---|---|---|---|
| Age: Median years (range) | 70 (34-95) | 70 (34-95) | 72 (44-90) | 0.84 |
| Male sex | 235 (73.2%) | 191 (71.0%) | 44 (84.6%) | 0.042 |
| Caucasian | 320 (99.7%) | 269 (100%) | 51 (98.1%) | 0.16 |
| Non-Hispanic* | 312 (97.2%) | 262 (97.4%) | 50 (96.2%) | 0.62 |
| Immune deficient | 76 (23.7%) | 59 (21.9%) | 17 (32.7%) | 0.10 |
| Prior Hx of SCC | 135 (42.1%) | 109 (40.5%) | 26 (50.0%) | 0.22 |
| Located on H&N | 214 (66.7%) | 171 (63.6%) | 43 (82.7%) | 0.007 |
| Tumor diameter: Mean cm (StDev)** | 1.8 (+/-1.9) | 1.6 (+/-1.8) | 2.8 (+/-2.4) | <0.0001 |
| Tumor thickness: Mean mm (StDev)# | 3.9 (+/-6.4) | 3.4 (+/-6.6) | 7.2 (+/-3.5) | <0.0001 |
| Poorly differentiated | 36 (11.2%) | 22 (8.2%) | 14 (26.9%) | <0.0001 |
| Clark Level IV / V | 62 (19.3%) | 49 (18.2%) | 13 (25.0%) | <0.0001 |
| PNI present | 36 (11.2%) | 21 (7.8%) | 15 (28.9%) | <0.0001 |
| Invasion into fat | 43 (13.4%) | 28 (10.4%) | 15 (28.9%) | 0.0004 |
| Definitive surgery MMS## | 256 (79.8%) | 222 (82.5%) | 34 (65.4%) | 0.032 |
| AJCC8 T Stage | | | | |
| T1 | 187 (58.3%) | 165 (61.3%) | 22 (42.3%) | |
| T2 | 58 (18.1%) | 53 (19.7%) | 5 (9.6%) | 0.0001 |
| T3 | 69 (21.5%) | 46 (17.1%) | 23 (44.2%) | |
| T4 | 7 (2.2%) | 5 (1.9%) | 2 (3.9%) | |
| BWH T Stage | | | | |
| T1 | 178 (55.5%) | 160 (59.5%) | 18 (34.6%) | |
| T2a | 98 (30.5%) | 80 (29.7%) | 18 (34.6%) | 0.0002 |
| T2b | 30 (9.3%) | 21 (7.8%) | 9 (17.3%) | |
| T3 | 15 (4.7%) | 8 (3.0%) | 7 (13.5%) | |
| NCCN High risk | 300 (93.5%) | 250 (92.9%) | 50 (96.2%) | |

FIG.8

| Multivariate Cox Regression | | |
|---|---|---|
| n=321 (52 events) | HR (95% CI) | p value |
| 40-GEP | | |
|    Class 1 | 1.0 | --- |
|    Class 2A | 2.17 (1.13-4.14) | 0.019 |
|    Class 2B | 9.34 (4.68-18.64) | <0.0001 |
| AJCC8 | | |
|    T1/T2 | 1.0 | --- |
|    T3/T4 | 2.98 (1.73-5.16) | <0.0001 |
| 40-GEP | | |
|    Class 1 | 1.0 | --- |
|    Class 2A | 2.23 (1.16-4.27) | 0.016 |
|    Class 2B | 8.68 (4.30-17.51) | <0.0001 |
| BWH | | |
|    T1/T2a | 1.0 | --- |
|    T2b/T3 | 2.32 (1.27-4.23) | 0.006 |

NOTE. An event was regional or distant metastasis.
Abbreviations: HR, hazard ratio; CI, confidence interval; GEP, gene expression profile; AJCC8, American Joint Committee on Cancer, Cancer Staging Manual, Eighth Edition; BWH, Brigham and Women's Hospital.

FIG.9

| Clinicopathologic Risk Group* | 40-GEP Class | | | | | | Total (n=321) |
|---|---|---|---|---|---|---|---|
| | Class 1 | | Class 2A | | Class 2B | | |
| | NonMet | Met | NonMet | Met | NonMet | Met | |
| AJCC8 | | | | | | | |
| T1 | 121 | 8 | 39 | 7 | 5 | 7 | 187 |
| T2 | 32 | 2 | 18 | 2 | 3 | 1 | 58 |
| T3 | 31 | 8 | 14 | 10 | 1 | 5 | 69 |
| T4 | 1 | 0 | 3 | 0 | 1 | 2 | 7 |
| BWH | | | | | | | |
| T1 | 119 | 7 | 37 | 5 | 4 | 6 | 178 |
| T2a | 50 | 6 | 26 | 8 | 4 | 4 | 98 |
| T2b | 13 | 5 | 7 | 3 | 1 | 1 | 30 |
| T3 | 3 | 0 | 4 | 3 | 1 | 4 | 15 |
| NCCN | | | | | | | |
| low risk | 13 | 1 | 5 | 1 | 1 | 0 | 21 |
| high risk | 172 | 17 | 69 | 18 | 9 | 15 | 300 |

Abbreviations: GEP, gene expression profile; AJCC8, American Joint Committee on Cancer, Cancer Staging Manual, Eighth Edition; BWH, Brigham and Women's Hospital; NCCN, National Comprehensive Cancer Network; PPV, positive predictive value; NPV, negative predictive value.
*Missing histopathologic information was treated as negative.

FIG.10

| Accuracy Metric | 40-GEP (Class 2B v 1/2A) | 40-GEP (Class 2 v 1) | AJCC 8* (T3/T4 v T1/T2) | BWH* (T2b/T3 v T1/T2a) | NCCN* (High v low) |
|---|---|---|---|---|---|
| Sensitivity | 28.8% | 65.4% | 53.8% | 30.8% | 96.2% |
| Specificity | 96.3% | 68.8% | 63.2% | 89.2% | 7.1% |
| PPV | 60.0% | 28.8% | 22.0% | 35.6% | 16.7% |
| NPV | 87.5% | 91.1% | 87.0% | 87.0% | 90.5% |

Abbreviations: GEP, gene expression profile; AJCC, American Joint Committee on Cancer, Cancer Staging Manual, Eighth Edition; BWH, Brigham and Women's Hospital; NCCN, National Comprehensive Cancer Network; PPV, positive predictive value; NPV, negative predictive value.
*Missing histopathologic information was treated as negative.

FIG.11

| Multivariate Cox Regression | | |
|---|---|---|
| n=321 (52 events) | HR (95% CI) | p value |
| 40-GEP | | |
|    Class 1 | 1.0 | — |
|    Class 2A | 2.27 (1.19-4.35) | 0.013 |
|    Class 2B | 12.44 (6.11-25.32) | <0.0001 |
| AJCC8 | | |
|    T1 | 1.0 | — |
|    T2 | 0.64 (0.24-1.69) | 0.37 |
|    T3 | 3.38 (1.87-6.12) | <0.0001 |
|    T4 | 0.78 (0.18-3.45) | 0.75 |
| 40-GEP | | |
|    Class 1 | 1.0 | — |
|    Class 2A | 2.13 (1.10-4.09) | 0.024 |
|    Class 2B | 8.55 (4.16-17.59) | <0.0001 |
| BWH | | |
|    T1 | 1.0 | — |
|    T2a | 1.67 (0.87-3.23) | 0.13 |
|    T2b | 3.15 (1.41-7.04) | 0.0051 |
|    T3 | 2.66 (1.06-6.63) | 0.037 |

NOTE. An event was regional or distant metastasis.

Abbreviations: HR, hazard ratio; CI, confidence interval; GEP, gene expression profile; AJCC8, American Joint Committee on Cancer, Cancer Staging Manual, Eighth Edition; BWH, Brigham and Women's Hospital.

FIG.12

| Feature | All (n=122) | NonMet (n=109) | Regional/distant met (n=13) | p value |
|---|---|---|---|---|
| Age: Median years (range) | 74 (49-97) | 74 (50-97) | 74 (49-91) | 0.03 |
| Male sex | 94 (77.1%) | 82 (75.2%) | 12 (92.3%) | 0.16 |
| Immune deficient | 17 (13.9%) | 14 (12.8%) | 3 (23.1%) | 0.31 |
| Located on H&N | 87 (71.3%) | 78 (71.6%) | 9 (69.2%) | 0.86 |
| Tumor diameter: Mean cm (StDev) | 2.05 (+/-2.86) | 1.56 (+/-1.29) | 6.12 (+/-6.84) | <0.0001 |
| Tumor thickness: Mean mm (StDev) | 2.39 (+/-2.84) | 1.97 (+/-1.56) | 10.5 (+/-8.32) | 0.005 |
| Poorly differentiated | 5 (4.1%) | 4 (3.7%) | 1 (7.7%) | 0.08 |
| Clark Level IV / V | 45 (36.9%) | 41 (37.6%) | 4 (30.8%) | 0.017 |
| PNI present | 7 (5.7%) | 7 (6.4%) | 0 (0%) | 0.35 |
| Invasion into fat | 7 (5.7%) | 5 (4.6%) | 2 (15.4%) | 0.11 |
| AJCC8 T Stage | | | | |
| T1 | 62 (50.8%) | 62 (56.9%) | 0 (0%) | |
| T2 | 36 (29.5%) | 32 (29.4%) | 4 (30.8%) | <0.0001 |
| T3 | 23 (18.9%) | 14 (12.8%) | 9 (69.2%) | |
| T4 | 1 (0.8%) | 1 (0.9%) | 0 (0%) | |
| BWH T Stage | | | | |
| T1 | 58 (47.5%) | 58 (53.2%) | 0 (0%) | |
| T2a | 55 (45.1%) | 45 (41.3%) | 10 (76.9%) | 0.001 |
| T2b | 8 (6.6%) | 5 (4.6%) | 3 (23.1%) | |
| T3 | 1 (0.8%) | 1 (0.9%) | 0 (0%) | |

NOTE. Data analyzed using Chi-square test or Kruskal-Wallis F test.
Abbreviations: H&N, head and neck; StDev, standard deviation; PNI, perineural invasion; AJCC8, American Joint Committee on Cancer, Cancer Staging Manual, Eighth Edition; BWH, Brigham and Women's Hospital.

FIG. 13

Cox Regression Analysis

| Feature | Univariate HR | Univariate p value | Multivariate HR (95% CI) | Multivariate p value |
|---|---|---|---|---|
| *Analysis with clinical features captured prior to definitive surgery (n = 295\*\*)* | | | | |
| Age[a] | 1.00 | 0.84 | — | — |
| Male sex | 2.16 | 0.045 | 1.28 (0.58-2.81) | 0.54 |
| Tumor diameter[a] | 1.13 | 0.00058 | 1.11 (1.02-1.21) | 0.016 |
| Immune deficient | 1.54 | 0.15 | — | — |
| Located on H&N | 2.56 | 0.011 | 2.44 (1.11-5.37) | 0.027 |
| GEP Class 2A | 2.44 | 0.0068 | 2.08 (1.03-4.20) | 0.041 |
| GEP Class 2B | 10.15 | <0.0001 | 7.56 (3.33-17.15) | <0.0001 |
| *Analysis with histopathological features captured after definitive surgery (n=321\*\*)* | | | | |
| Tumor thickness >6mm | 3.59 | 0.00091 | 1.86 (0.75-4.65) | 0.18 |
| Poor histological grade | 3.45 | <0.0001 | 1.99 (0.98-4.00) | 0.057 |
| Clarks Level IV/V | 1.51 | 0.20 | — | — |
| Perineural invasion | 3.65 | <0.0001 | 1.14 (0.48-2.69) | 0.77 |
| Invasion into fat | 3.04 | <0.0001 | 2.10 (1.01-4.39) | 0.045 |
| GEP Class 2A | 2.44 | 0.0068 | 1.88 (0.96-3.68) | 0.060 |
| GEP Class 2B | 10.15 | <0.0001 | 7.94 (3.88-16.27) | <0.0001 |

NOTE. Only variables demonstrating statistical significance in univariate analysis were included in the multivariate analysis.

Abbreviations: HR, hazard ratio; CI, confidence interval; H&N, head and neck; GEP, gene expression profile.

\*Cases without reported tumor diameters were excluded from the multivariate analysis (n=26).

[a] Assessed as a continuous variable per unit increase.

\*\*Analysis of post-operative features indicated a violation of the assumptions of proportional hazards for several features, indicating that the hazard ratio estimates for the features may not be accurate. Two parametric survival regression models were used in addition to the Cox proportional hazards model, all of which resulted in similar conclusions of independence of the GEP risk categorization and significance of the post-operative histopathological factors.

FIG.14A

Cohort stratification and metastasis rate by 40-GEP Class and T Stage

| 40-GEP Class | Overall Rate* | AJCC T Stage* | | BWH T Stage* | |
|---|---|---|---|---|---|
| | | T1-T2 | T3-T4 | T1-T2a | T2b-T3 |
| Class 1 | 9% (189) | 7.5% (159) | 16.7% (30) | 8.1% (173) | 18.8% (16) |
| Class 2A | 21% (87) | 15.6% (64) | 34.8% (23) | 17.8% (73) | 35.7% (14) |
| Class 2B | 63% (24) | 50.0% (16) | 87.5% (8) | 58.8% (17) | 71.4% (7) |

*Metastasis incidence and number (n) of patients in each Class and per T stage.

FIG.14B

Management intensity determined by risk for metastasis

- Low intensity (<10% risk)
- Moderate intensity (10-50% risk)
- High intensity (>50% risk)

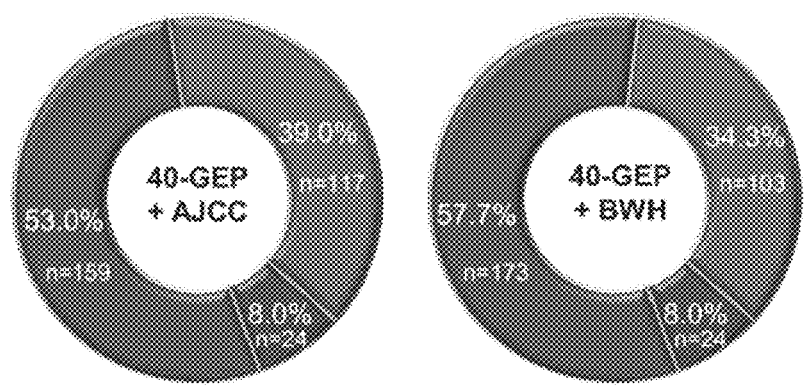

FIG.16

Characteristics of the NCCN high-risk cSCC cohort (n=300).

| Feature of Modeling Cohort | Cases (% of Cohort) |
| --- | --- |
| Age: Median years (range) | 70 (34-95) |
| Sex: Male | 219 (73%) |
| Immune deficient | 76 (25%) |
| Located on H&N | 201 (67%) |
| Tumor diameter*: mean cm (≥2 cm) | 1.85 (36%) |
| Tumor thickness**: mean mm (>6 mm) | 3.90 (16%) |
| Poorly differentiated | 36 (12%) |
| Clark Level IV / V | 62 (21%) |
| PNI present | 36 (12%) |
| Subcutaneous fat invasion | 43 (14%) |
| 40-GEP Result | |
|     Class 1 | 189 (63%) |
|     Class 2A | 87 (29%) |
|     Class 2B | 24 (8%) |

*275 cases had tumor diameter reported; **109 cases had thickness reported. NCCN, National Comprehensive Cancer Network; H&N, head and neck; PNI, perineural invasion; GEP, gene expression profile.

Note, NCCN high-risk criteria include tumor size ≥2 cm; tumor depth >6 mm or invasion beyond subcutaneous fat; poorly differentiated; perineural invasion; bone invasion; on ear or lip; on mask area of the face; on genitalia, hands, or feet; on forehead, scalp, cheek, or neck (size ≥10mm); rapid growth; immunosuppression; site of prior radiation therapy or chronic inflammatory process; recurrent tumor; neurologic symptoms; high-risk subtypes (acantholytic, adenosquamous, or desmoplastic).

Overall Clinical Validation Cohort n=420
p<0.0001

No. at risk

| | | | | | | |
|---|---|---|---|---|---|---|
| Class 1 | 212 | 205 | 200 | 199 | 73 | 37 |
| Class 2A | 185 | 164 | 151 | 149 | 81 | 39 |
| Class 2B | 23 | 14 | 12 | 11 | 7 | 3 |

| 40-GEP Risk Class | Overall Cohort | |
|---|---|---|
| | 3-year MFS (95% CI) | Overall Event Rate |
| Class 1 | 93.9% (90.7-97.2%) | 6.6% |
| Class 2A | 80.5% (75.0-86.5%) | 20.0% |
| Class 2B | 47.8% (31.2-73.3%) | 52.2% |
| Pre-Test | 85.5% (82.2-88.9%) | 15.0% |

| No. at risk | | | | | | |
|---|---|---|---|---|---|---|
| Class 1 | 101 | 97 | 97 | 97 | 31 | 14 |
| Class 2A | 65 | 60 | 58 | 58 | 33 | 13 |
| Class 2B | 5 | 2 | 2 | 2 | 1 | 0 |

| 40-GEP Risk Class | 1 Risk Factor | |
|---|---|---|
| | 3-year MFS (95% CI) | Overall Event Rate |
| Class 1 | 96.0% (92.3-99.9%) | 4.0% |
| Class 2A | 89.2% (82.0-97.1%) | 10.8% |
| Class 2B | 40.0% (13.7-100%) | 60.0% |
| Pre-test | 91.8% (87.7-96.0%) | 8.2% |

No. at risk
| | | | | | | |
|---|---|---|---|---|---|---|
| Class 1 | 111 | 108 | 103 | 102 | 42 | 23 |
| Class 2A | 120 | 104 | 93 | 91 | 48 | 26 |
| Class 2B | 18 | 12 | 10 | 9 | 6 | 3 |

| 40-GEP Risk Class | ≥2 Risk Factors | |
|---|---|---|
| | 3-year MFS (95% CI) | Overall Event Rate |
| Class 1 | 91.9% (87.0-97.1%) | 9.0% |
| Class 2A | 75.8% (68.5-83.9%) | 25.0% |
| Class 2B | 50.0% (31.5-79.4%) | 50.0% |
| Pre-test | 81.1% (76.4-86.1%) | 19.7% |

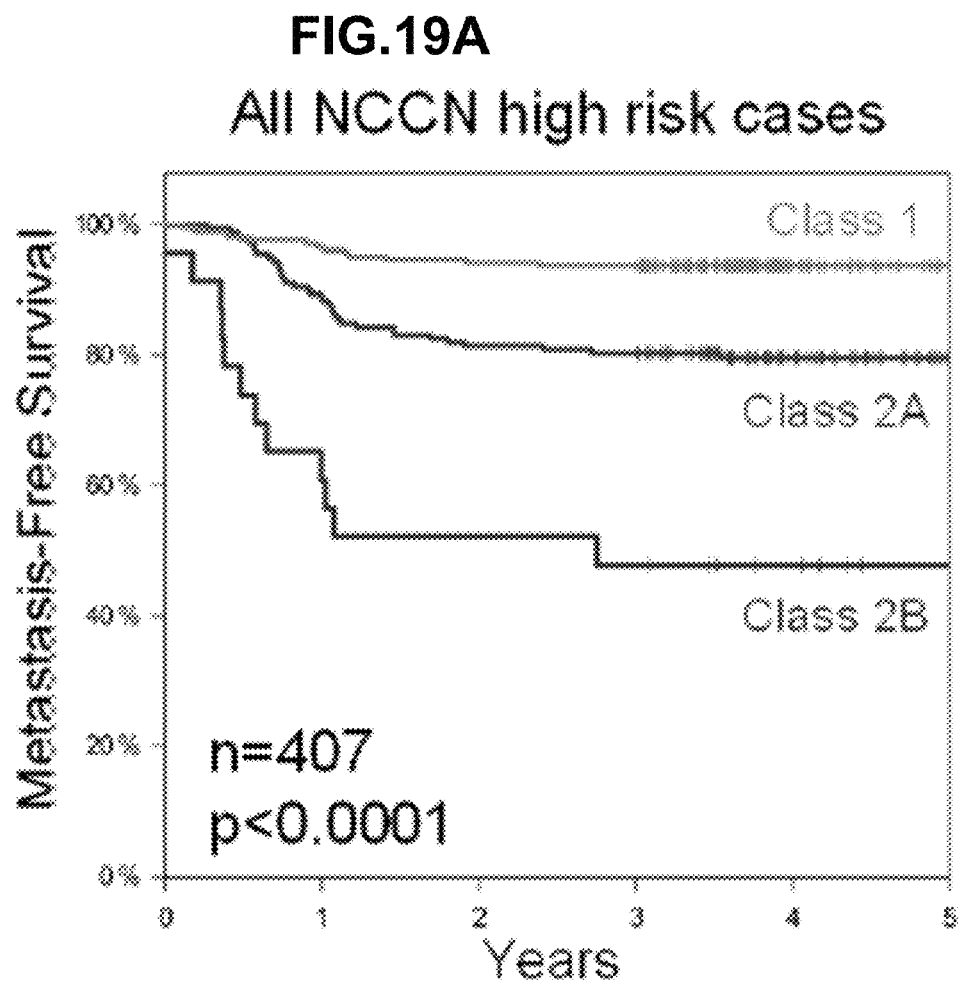

METHODS OF DIAGNOSING AND TREATING PATIENTS WITH CUTANEOUS SQUAMOUS CELL CARCINOMA

FIELD OF THE DISCLOSURE

The present disclosure relates to methods for predicting the risk of recurrence and/or metastasis in primary cutaneous squamous cell carcinoma (cSCC).

BACKGROUND

Cutaneous squamous cell carcinoma (cSCC) is rivaled only by basal cell carcinoma as the most common cancer in the U.S. Though most cases are cured by excision, a subset recur and become incurable with the number of deaths approximating melanoma (Karia et al., *J. Am. Acad. Dermatol.* 68(6): 957-66 (2013)). Despite overall good prognosis for patients with cSCC, a subset will develop local, regional, or distant recurrences/metastases following complete excision of the primary tumor. Those at high risk of recurrence are eligible for adjuvant treatment options. While specific clinical and pathologic features are associated with recurrence, they collectively fail to identify 30-40% of all cSCC recurrences and many tumors that possess high risk features will not recur. Furthermore, the rates of metastasis in high-risk patients (e.g., immunocompromised) and those diagnosed with tumors with high-risk features can exceed 20%. Once metastasis is detected, survival rates are poor. Prediction models with increased positive predictive values while maintaining high negative predictive values are needed to accurately identify patients with high-risk features who are at a much higher risk of developing metastasis and dying from cSCC than the high-risk features alone suggest. Prediction models with increased positive predictive values while maintaining high negative predictive values are critical and may allow for early intervention with adjuvant therapies. Similarly, many patients with high-risk features do not have recurrences and thus maintaining a high negative predictive value is important to avoid overtreatment and prevent unnecessary procedures in patients with low risk cSCC that are mis-categorized as high risk cSCC when using clinical and pathologic features alone. Patients with high-risk features but who are at an actual low risk of metastasis can avoid overtreatment of low risk tumors. To address the need for more accurate predictive factors and facilitate appropriate intervention strategies, gene expression analysis was used to determine a signature associated with recurrence in patients with cSCC, and the combination of the novel signature with clinicopathologic risk factors demonstrated improved risk stratification, which can facilitate risk-appropriate management decisions for high-risk cSCC patients.

SUMMARY

There is a need in the art for a more objective method of predicting which tumors display aggressive recurrence/metastatic activity. Development of an accurate molecular footprint, such as the gene expression profile assay disclosed herein, would be a significant advance forward for the field. A multi-center study using archived primary tissue samples with extensive capture of associated clinical and pathologic data (subjects with pathologically confirmed cSCC, minimum 2 years of follow-up, and in some cases a minimum of 3 years follow-up, and two separate outcome measures: nodal/distant metastasis and local recurrence) was used to identify a 40-gene expression profile (40-GEP) test that accurately predicts primary cSCC with a high risk of metastasis, and primary cSCC with high risk of recurrence after complete surgical clearance. In particular, the 40-GEP test disclosed herein identifies three classes (Class 1, Class 2A, and Class 2B) of cSCC patients who have increased likelihood of developing nodal or distant metastasis within 3 years of diagnosis. The 40-GEP test is an independent predictor of patient outcomes and improves upon risk prediction with American Joint Committee on Cancer (AJCC), Brigham Women's Hospital (BWH), and National Comprehensive Cancer Network (NCCN) systems supporting its clinical use in conjunction with or independent of standard staging and patient management criteria.

In one embodiment, a method for treating a patient with a cutaneous squamous cell carcinoma (cSCC) tumor is disclosed herein, the method comprising: (a) obtaining a diagnosis identifying a risk of metastasis, in a cSCC tumor sample from the patient, wherein the diagnosis was obtained by: (1) determining the expression level of 34 genes in a gene set; wherein the 34 genes in the gene set are: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839; (2) comparing the expression levels of the 34 genes in the gene set from the cSCC tumor sample to the expression levels of the 34 genes in the gene set from a predictive training set to generate a probability score of the risk of metastasis, and; (3) providing an indication as to whether the cSCC tumor has a low risk to a high risk of metastasis, based on the probability score generated in step (2); and (4) identifying that the cSCC tumor has a high risk of metastasis, based on the probability score and diagnosing the cSCC tumor as having a high risk of metastasis; (b) administering to the patient an aggressive treatment when the determination is made in the affirmative that the patient has a cSCC tumor with a high risk of metastasis. In certain embodiments, the method further comprises performing a resection of the cSCC tumor when the determination is made in the affirmative that the patient has a cSCC tumor with a high risk of metastasis. In certain embodiments, the method further comprises identifying that the cSCC tumor has a high risk of metastasis based on the probability score in combination with at least one risk factor, wherein the at least one risk factor is selected from tumor size, tumor location, immune status, perineural involvement (PNI), depth of invasion, differentiation, histological subtype, and lymphovascular invasion.

In some embodiments, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR). In certain embodiments, the cSCC tumor sample is obtained from formalin-fixed, paraffin embedded sample.

In another embodiment, the gene set comprises at least one additional gene selected from the genes AIM2, ANXA9, ARPC2, ATP6AP1, BLOC1S1, ClQL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

In another embodiment, a method of treating a patient with a cutaneous squamous cell carcinoma (cSCC) tumor is disclosed herein, the method comprising administering an aggressive cancer treatment regimen to the patient, wherein the patient has a cSCC tumor with a moderate risk (Class 2A) or a high risk (Class 2B) as generated by comparing the expression levels of 34 genes selected from ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839 from the cSCC tumor with the expression levels of the same 34 genes selected from ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839 from a predictive training set. In one embodiment, the cSCC tumor is determined to have a low risk (Class 1), a moderate risk (Class 2A), or a high risk (Class 2B), wherein a patient having a low risk (Class 1) cSCC tumor has about a 0-10% risk for metastasis, a patient having a moderate risk (Class 2A) cSCC tumor has about a 10-49% risk for metastasis, and a patient having a high risk (Class 2B) cSCC tumor has about a 50-100% risk for metastasis. In certain embodiments, the method further comprises determining that the cSCC tumor has a low risk (Class 1), a moderate risk (Class 2A), or a high risk (Class 2B) based on the expression levels of the 34 genes in combination with at least one risk factor, wherein the at least one risk factor is selected from tumor size, tumor location, immune status, perineural involvement (PNI), depth of invasion, differentiation, histological subtype, and lymphovascular invasion.

In another embodiment, the gene set comprises at least one additional gene selected from the genes AIM2, ANXA9, ARPC2, ATP6AP1, BLOC1S1, C1QL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

In another embodiment, a kit comprising primer pairs suitable for the detection and quantification of nucleic acid expression of 34 genes is disclosed herein, wherein the 34 genes are selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839.

In some embodiments, the primer pairs suitable for the detection and quantification of nucleic acid expression of 34 genes are primer pairs for: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839. In other embodiments, the primer pairs comprise primer pairs for at least one additional gene selected from the genes AIM2, ANXA9, ARPC2, ATP6AP1, BLOC1S1, C1QL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

In another embodiment, a method for predicting risk of metastasis, in a patient with a cutaneous squamous cell carcinoma (cSCC) tumor is disclosed herein, the method comprising: (a) obtaining a cSCC tumor sample from the patient and isolating mRNA from the sample; (b) determining the expression level of 34 genes in a gene set; wherein the 34 genes in the gene set are selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839; (c) comparing the expression levels of the 34 genes in the gene set from the cSCC tumor sample to the expression levels of the 34 genes in the gene set from a predictive training set to generate a probability score of the risk of metastasis; and (d) providing an indication as to whether the cSCC tumor has a low risk to a high risk of metastasis, based on the probability score generated in step (c). In certain embodiments, the method further comprises identifying that the cSCC tumor has a high risk of metastasis based on the probability score in combination with at least one risk factor, wherein the at least one risk factor is selected from tumor size, tumor location, immune status, perineural involvement (PNI), depth of invasion, differentiation, histological subtype, and lymphovascular invasion.

In some embodiments, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR). In certain embodiments, the cSCC tumor sample is obtained from formalin-fixed, paraffin embedded sample. In one embodiment, the method further comprises identifying the cSCC tumor as having a high risk of metastasis, based on the probability score, and administering to the patient an aggressive tumor treatment.

In another embodiment, the gene set comprises at least one additional gene selected from the genes AIM2, ANXA9, ARPC2, ATP6AP1, BLOC1S1, C1QL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or 10, 15, 20, 25, 30, 35, 40, or more than 40 genes selected from the genes listed above.

In another embodiment, a method for predicting risk of metastasis, in a patient with a cutaneous squamous cell carcinoma (cSCC) tumor is disclosed herein, the method comprising: (a) obtaining a cSCC tumor sample from the patient and isolating mRNA from the sample; (b) determining the expression level of 34 genes in a gene set; wherein the 34 genes in the gene set are selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839; and (c) providing an indication as to whether the cSCC tumor has a low risk to a high risk of metastasis, based on the expression level of 34 genes generated in step (b).

In some embodiments, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR). In certain embodiments, the cSCC tumor sample is obtained from formalin-fixed, paraffin embedded sample.

In another embodiment, the gene set comprises at least one additional gene selected from the genes AIM2, ANXA9, ARPC2, ATP6AP1, BLOC1S1, C1QL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

In certain embodiments, the expression level of: ACSBG1 is decreased, ALOX12 is decreased, APOBEC3G is increased, ATP6V0E2 is increased, BBC3 is increased, BHLHB9 is decreased, CEP76 is decreased, DUXAP8 is increased, GTPBP2 is decreased, HDDC3 is increased, ID2 is decreased, LCE2B is decreased, LIME1 (ZGPAT) is increased, LOC100287896 is increased, LOC101927502 is increased, MMP10 is decreased, MRC1 is decreased, MSANTD4 is decreased, NFASC is decreased, NFIC is decreased, PDPN is increased, PI3 is decreased, PLS3 is decreased, RCHY1 is increased, RNF135 is increased, RPP38 is decreased, RUNX3 is increased, SLC1A3 is increased, SPP1 is increased, TAF6L is increased, TFAP2B is decreased, ZNF48 is increased, ZNF496 is increased, and ZNF839 is increased when comparing a recurrent tumor to a non-recurrent sample.

In certain embodiments, the expression level of the at least one additional gene: ACSBG1 is decreased, AIM2 is increased, ALOX12 is decreased, ANXA9 is decreased, APOBEC3G is increased, ARPC2 is decreased, ATP6AP1 is decreased, ATP6V0E2 is increased, BBC is increased, BHLHB9 is decreased, BLOC1S1 is decreased, C1QL4 is increased, C21orf59 is increased, C3orf70 is increased, CCL27 is decreased, CD163 is increased, CEP76 is decreased, CHI3L1 is increased, CHMP2B is decreased, CXCL10 is decreased, CXCR4 is increased, CYP2D6 (LOC101929829) is decreased, DARS is decreased, DCT is decreased, DDAH1 is decreased, DSS1 is decreased, DUXAP8 is increased, EGFR is increased, EphB2 is increased, FCHSD1 is decreased, FDFT1 is decreased, FLG is decreased, FN1 is increased, GTPBP2 is decreased, HDDC3 is increased, HNRNPL is decreased, HOXA10 (HOXA9, MIR196B) is decreased, HPGD is decreased, ID2 is decreased, IL24 is increased, IL2RB is decreased, IL7R is increased, INHBA is increased, IPO5P1 is increased, KIT is increased, KLK5 is decreased, KRT17 is decreased, KRT18 is increased, KRT19 is decreased, KRT6B is decreased, LAMC2 is decreased, LCE2B is decreased, LIME1 (ZGPAT) is increased, LOC100287896 is increased, LOC101927502 is increased, LOR is decreased, LRRC47 is increased, MIER2 is increased, MIR129-1 is increased, MIR3916 is increased, MKLN1 is increased, MMP1 is increased, MMP10 is decreased, MMP12 is increased, MMP13 is increased, MMP3 is increased, MMP7 is increased, MMP9 is decreased, MRC1 is decreased, MRPL21 is increased, MSANTD4 is decreased, MYC is decreased, NEB is decreased, NEFL is decreased, NFASC is decreased, NFIA is decreased, NFIB is decreased, NFIC is decreased, NOA1 is increased, PD1 is decreased, PDL1 is increased, PDPN is increased, PI3 is decreased, PIG3 is decreased, PIGBOS1 is increased, PIM2 is increased, PLAU is increased, PLS3 is decreased, PTHLH is decreased, PTRHD1 is decreased, RBM33 is increased, RCHY1 is increased, RNF135 is increased, RPL26L1 is increased, RPP38 is decreased, RUNX3 is increased, S100A8 is decreased, S100A9 is decreased, SEPT3 is decreased, SERPINB2 is decreased, SERPINB4 is decreased, SLC1A3 is increased, SLC25A11 is increased, SNORD124 is increased, SPATA41 is increased, SPP1 is increased, TAF6L is increased, TFAP2B is decreased, THYN1 is increased, TMEM41B is decreased, TNNC1 is decreased, TUBB3 is decreased, TUFM (MIR4721) is increased, TYRP1 is decreased, UGP2 is decreased, USP7 is decreased, VIM is increased, YKT6 is increased, ZNF48 is increased, ZNF496 is increased, ZNF839 is increased, and/or ZSCAN31 is decreased. In certain embodiments, the increase or decrease in the expression level is the gene level from a recurrent tumor sample versus a non-recurrent tumor sample. In other embodiments, the increase or decrease in the expression level is the gene level from a metastatic tumor sample versus a non-metastatic tumor sample.

In another embodiment, a method for treating a patient with cutaneous squamous cell carcinoma (cSCC) tumor is disclosed herein, the method comprising: (a) obtaining a cSCC tumor sample from the patient and isolating mRNA from the sample; (b) determining the expression level of 34 genes in a gene set; wherein the 34 genes in the gene set are selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839; (c) providing an indication as to whether the cSCC tumor has a low risk (Class 1), a moderate risk (Class 2A), or a high risk (Class 2B) of metastasis, based on the expression level of the 34 genes generated in step (b); and (d) administering to the patient an aggressive treatment when the determination is made in the affirmative that the patient has a cSCC tumor with a moderate risk or a high risk of metastasis. In certain embodiments, the method further comprises determining that the cSCC tumor has a low risk (Class 1), a moderate risk (Class 2A), or a high risk (Class 2B) based on the expression levels of the 34 genes in combination with at least one risk factor, wherein the at least one risk factor is selected from tumor size, tumor location, immune status, perineural involvement (PNI), depth of invasion, differentiation, histological subtype, and lymphovascular invasion.

In some embodiments, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR). In certain embodiments, the cSCC tumor sample is obtained from formalin-fixed, paraffin embedded sample.

In another embodiment, the gene set comprises at least one additional gene selected from the genes AIM2, ANXA9, ARPC2, ATP6AP1, BLOC1S1, ClQL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

In another embodiment, the disclosure provides a method of determining one or more treatment options for a patient with a cutaneous squamous cell carcinoma (cSCC) tumor, the method comprising:
(a) identifying a risk of metastasis in a cSCC tumor sample from the patient, wherein the risk of metastasis was identified by:
    (1) determining the expression level of 34 genes in a gene set; wherein the 34 genes in the gene set are: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839;
    (2) comparing the expression levels of the 34 genes in the gene set from the cSCC tumor sample to the expression levels of the 34 genes in the gene set from a predictive training set to identify the risk of metastasis and providing an indication as to whether the cSCC tumor has a low risk (Class 1), a moderate risk (Class 2A), or a high risk (Class 2B) of metastasis; and
(b) determining that the patient receive a low intensity treatment, a moderate intensity treatment, or a high intensity treatment when the determination is made that the patient has a cSCC tumor with a low risk (Class 1), a moderate risk (Class 2A), or a high risk (Class 2B) of metastasis, respectively.

In certain embodiments, the method further comprises determining that the cSCC tumor has a low risk (Class 1), a moderate risk (Class 2A), or a high risk (Class 2B) based on the expression levels of the 34 genes in combination with at least one risk factor, wherein the at least one risk factor is selected from tumor size, tumor location, immune status, perineural involvement (PNI), depth of invasion, differentiation, histological subtype, and lymphovascular invasion.

In certain embodiments, the low intensity treatment comprises one or more of:
(a) clinical follow-up of one to two times per year;
(b) reduced imaging or low frequency to no imaging;
(c) reduced nodal assessment; and/or
(d) no adjuvant treatment.

In other embodiments, the moderate intensity treatment comprises one or more of:
(a) clinical follow-up of two to four times per year for about 3 years;
(b) baseline and annual nodal imaging for about 2 years;
(c) consider a nodal biopsy or a neck dissection; and/or
(d) consider an adjuvant treatment.

In some embodiments, the high intensity treatment comprises one or more of:
(a) clinical follow-up of four to twelve times per year for about 3 years;
(b) baseline and annual nodal imaging at least twice a year for about 2 years;
(c) recommend a nodal biopsy or a neck dissection; and/or
(d) recommend an adjuvant treatment and/or a clinical trial.

In certain embodiments, the method further comprises performing a resection of the cSCC tumor when the determination is made in the affirmative that the patient has a cSCC tumor with a moderate risk (Class 2A) or a high risk (Class 2B) of metastasis.

In some embodiments, the expression level of each gene in a gene set is determined by reverse transcribing the isolated mRNA and measuring a level of fluorescence for each gene in the gene set by a nucleic acid sequence detection system following RT-PCR. In an embodiment, the cSCC tumor sample is obtained from a formalin-fixed, paraffin embedded sample.

In certain embodiments, the gene set further comprises at least one control gene, wherein the at least one control gene is selected from the group consisting of BAG6, KMT2D/MLL2, MDM2, FXR1, KMT2C, MDM4, VIM, and NF1B. In an embodiment, the control genes are MDM2, KMT2D, BAG6, FXR1, MDM4, and KMT2C.

Other aspects, embodiments, and implementations will become apparent from the following detailed description and claims, with reference, where appropriate, to the accompanying drawings.

BRIEF DESCRIPTION OF THE DRAWINGS

FIG. 6 shows the Kaplan-Meier analysis of the 40-GEP prognostic test and outcomes from independent validation of cutaneous SCC cases (n=321).

FIG. 7 shows the demographics and clinical characteristics of validation cohort (n=321). Data analyzed using Chi-square test or Kruskal-Wallis F test. Abbreviations: Hx, history; SCC, squamous cell carcinoma; H&N, head and neck; StDev, standard deviation; PNI, perineural invasion; MMS, Mohs micrographic surgery; AJCC8, American Joint Committee on Cancer, Cancer Staging Manual, Eighth Edition; BWH, Brigham and Women's Hospital; NCCN, National Comprehensive Cancer Network. *One (n=1) patient did not report ethnicity. **Tumor diameter reported (n=295). #Tumor thickness reported (n=115). ##Mohs or wide local excision (n=319) with 2 cases not having additional surgery beyond biopsy.

FIG. 8 shows Multivariate Cox regression analyses of risk for metastasis in 40-GEP validation cases (n=321) with binary AJCC and BWH T stage. An event was regional or distant metastasis. Abbreviations: HR, hazard ratio; CI, confidence interval; GEP, gene expression profile; AJCC8, American Joint Committee on Cancer, Cancer Staging Manual, Eighth Edition; BWH, Brigham and Women's Hospital.

FIG. 9 shows classification of cases by 40-GEP Class and clinicopathologic risk group (n=321).

FIG. 10 shows the accuracy of risk prediction of the 40-GEP and risk assessment methods (n=321).

FIG. 11 shows Multivariate Cox regression analyses of risk for metastasis in 40-GEP validation cases (n=321) with AJCC or BWH T stage.

FIG. 12 shows the demographics of the training cohort.

FIG. 13 shows Multivariate Cox regression analyses for risk of metastasis in validation cases with individual pre-operative and post-operative features.

FIG. 14A-14B show the application of 40-GEP test results and T stage to NCCN-defined levels of risk for improving risk-appropriate management of cSCC. FIG. 14A—Using a cohort (n=300) of clinicopathologically defined cSCC patients meeting study criteria and who were NCCN-defined high risk, the 40-GEP test stratified the patients into three groups depending on risk for metastasis at 3 years post-diagnosis: low (Class 1, n=189), high (Class 2A, n=87), or highest (Class 2B, n=24). Patients stratified as Class 1, 2A, and 2B had a 9%, 21%, and 63% risk for metastasis, respectively, per the 40-GEP test alone. Corresponding AJCC and BWH T stages and metastasis rates were analyzed. FIG. 14B—Incorporation of 40-GEP Class plus AJCC and BWH T stages into three metastasis risk bins (<10%, 10-50%, and >50% risk) resulted in low, moderate, and high intensity management strategies. The 40-GEP integration demonstrates low management intensity for 53.0% (AJCC) or 57.7% (BWH), high intensity management for 8.0%, and moderate intensity management for the remainder (39.0%, AJCC; 34.3%, BWH) of the 300-patient cohort.

FIG. 16 shows the characteristics of the NCCN high-risk cSCC cohort (n=300).

FIG. 19A shows that when only including cases classified as NCCN high risk (n=407, 62 metastatic cases), stratification of risk by the 40-GEP in line with that of the full cohort was observed.

DETAILED DESCRIPTION

Figure 1:
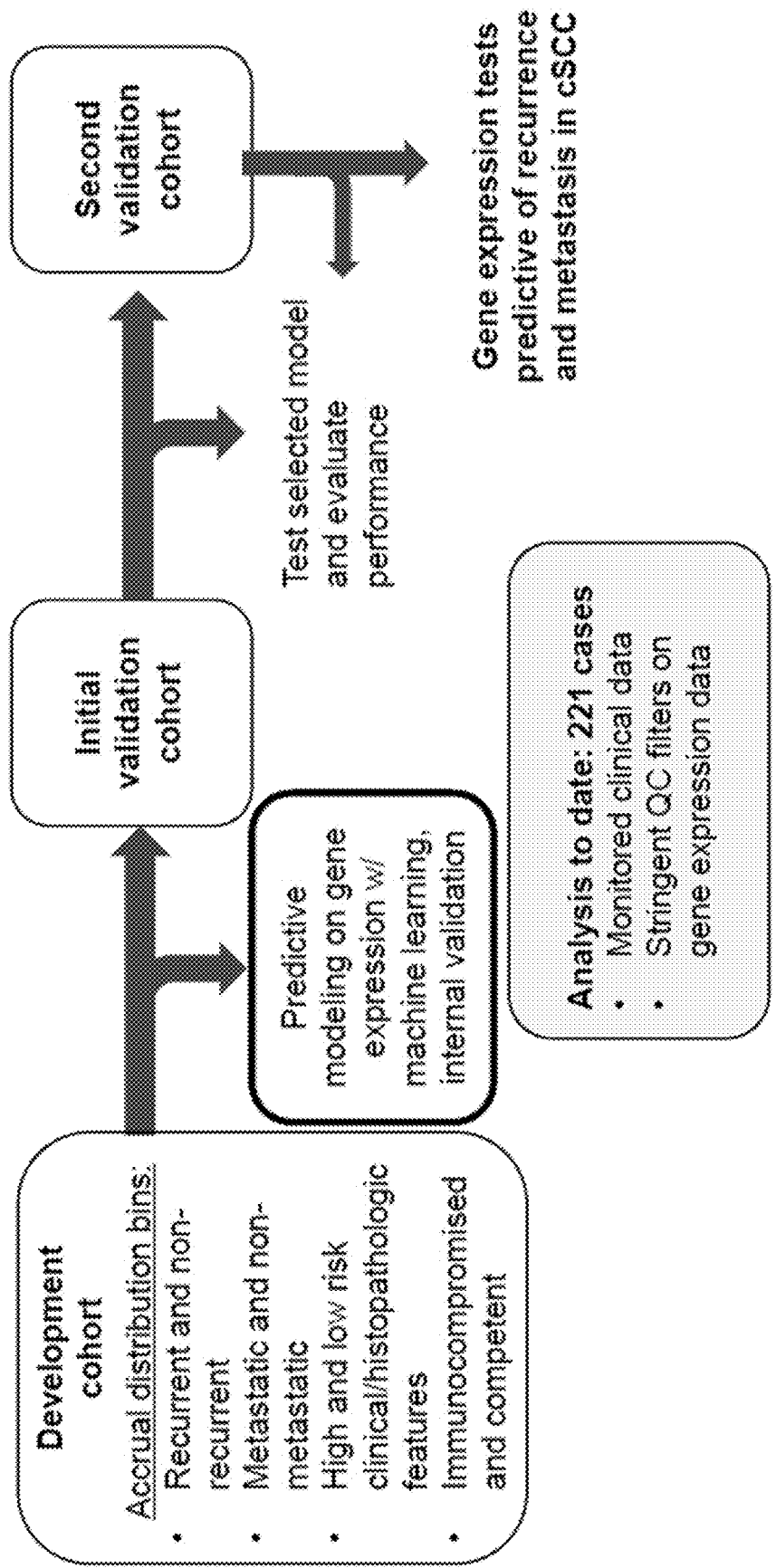
FIG. 1 shows the study design workflow.

Despite overall good prognosis for patients with cSCC, a subset will develop metastasis (i.e., local, regional, or distant recurrences, or any combination) following complete excision of the primary tumor. Those at high risk of metastasis/recurrence are eligible for adjuvant treatment options. While specific clinical features are associated with metastasis/recurrence, they collectively fail to identify 30-40% of all cSCC recurrences and many tumors that express high risk features will not recur. To address the need for more accurate predictive factors and facilitate appropriate intervention strategies, a gene expression analysis was used to determine a signature associated with metastasis/recurrence in cSCC. In that analysis, 140 candidate genes were selected for evaluation of gene expression changes in recurrent (metastatic) and non-recurrent cases. A total of 230 primary cSCC tumors were collected under an IRB-approved, multi-center protocol and analyzed. After quality filtering, expression of the genes was assessed across 202 samples. Multiple subsets of genes were significantly differentially expressed between metastatic/recurrent and non-recurrent cases. The results demonstrate that gene expression differences can distinguish between metastatic/recurrent and non-recurrent cSCC. Such gene expression differences can help identify those patients who might benefit from additional therapeutic interventions and treatments.

Unless otherwise defined, all technical and scientific terms used herein have the same meaning as would be commonly understood by one of ordinary skill in the art to which the claimed invention belongs. Although methods and materials similar or equivalent to those described herein can be used to practice the methods and kits disclosed or claimed herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting. Other features and advantages of the claimed invention will be apparent from the following detailed description.

As used herein, the singular forms "a," "an," and "the" include plural referents unless the context clearly dictates otherwise. For example, reference to "a nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment disclosed or claimed herein.

As used herein, the terms "polynucleotide," "nucleotide," "oligonucleotide," and "nucleic acid" can be used interchangeably to refer to nucleic acid comprising DNA, cDNA, RNA, derivatives thereof, or combinations thereof.

In an embodiment, a method for treating a patient with a cutaneous squamous cell carcinoma (cSCC) tumor is disclosed herein, the method comprising: (a) obtaining a diagnosis identifying a risk of local metastasis (i.e., recurrence, regional metastasis, distant metastasis, or any combination), in a cSCC tumor sample from the patient, wherein the diagnosis was obtained by: (1) determining the expression level of 34 genes in a gene set; wherein the 34 genes in the gene set are selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839; (2) comparing the expression levels of the 34 genes in the gene set from the cSCC tumor sample to the expression levels of the 34 genes in the gene set from a predictive training set to generate a probability score of the risk of metastasis, and; (3) providing an indication as to whether the cSCC tumor has a low risk to a high risk of metastasis, based on the probability score generated in step (2); and (4) identifying that the cSCC tumor has a high risk of metastasis, based on the probability score and diagnosing the cSCC tumor as having a high risk of metastasis; (b) administering to the patient an aggressive treatment when the determination is made in the affirmative that the patient has a cSCC tumor with a high risk of metastasis. In certain embodiments, the method further comprises performing a resection of the cSCC tumor when the determination is made in the affirmative that the patient has a cSCC tumor with a high risk of metastasis. In certain embodiments, the method further comprises identifying that the cSCC tumor has a high risk of metastasis based on the probability score in combination with at least one risk factor, wherein the at least one risk factor is selected from tumor size, tumor location, immune status, perineural involvement (PNI), depth of invasion, differentiation, histological subtype, and lymphovascular invasion.

In some embodiments, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR). In certain embodiments, the cSCC tumor sample is obtained from formalin-fixed, paraffin embedded sample.

In another embodiment, the gene set comprises at least one additional gene selected from the genes AIM2, ANXA9, ARPC2, ATP6AP1, BLOC1S1, C1QL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or 10, 15, 20, 25, 30, 35, 40, or more than 40 genes selected from the genes listed above.

In an embodiment, a method of treating a patient with a cutaneous squamous cell carcinoma (cSCC) tumor is disclosed herein, the method comprising administering an aggressive cancer treatment regimen to the patient, wherein the patient has a cSCC tumor with moderate risk (Class 2A), or a high risk (Class 2B) as generated by comparing the expression levels of 34 genes selected from ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839 from the cSCC tumor with the expression levels of the same 34 genes selected from ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839 from a predictive training set. In one embodiment, the cSCC tumor is determined to have a low risk (Class 1), a moderate risk (Class 2A), or a high risk (Class 2B), wherein a patient having a low risk (Class 1) cSCC tumor has about a 0-10% risk for metastasis, a patient having a moderate risk (Class 2A) cSCC tumor has about a 10-49% risk for metastasis, and a patient having a high risk (Class 2B) cSCC tumor has about a 50-100% risk for metastasis (i.e., local recurrence, regional metastasis, distant metastasis, or any combination). In certain embodiments, the method further comprises determining that the cSCC tumor has a low risk (Class 1), a moderate risk (Class 2A), or a high risk (Class 2B) based on the expression levels of the 34 genes in combination with at least one risk factor, wherein the at least one risk factor is selected from tumor size, tumor location, immune status, perineural involvement (PNI), depth of invasion, differentiation, histological subtype, and lymphovascular invasion.

In another embodiment, the gene set comprises at least one additional gene selected from the genes AIM2, ANXA9, ARPC2, ATP6AP1, BLOC1S1, C1QL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

As used herein, the terms "metastasis" and "recurrence" are used interchangeably, and refer to the recurrence or disease progression that may occur locally (such as local recurrence and in transit disease), regionally (such as regional metastasis, nodal micrometastasis or macrometastasis), or distally (such as distal metastasis to brain, lung and/or other tissues). In certain embodiment, regional metastasis refers to a metastatic lesion within the regional nodal basin, including satellite or in-transit metastasis, but excluding local recurrence, and distant metastasis refers to metastasis beyond the regional lymph node basin. Risk, as used herein, includes low-risk, moderate-risk, or high-risk of metastasis according to any of the statistical methods disclosed herein. In one embodiment, risk of recurrence or metastasis for cSCC can be classified from a low risk to a high risk (for example, the cSCC tumor has a graduated risk from low risk to high risk or high risk to low risk of metastasis, local recurrence, regional metastasis, or distant metastasis). In other embodiments, low risk refers to a 3-year relapse-free survival rate, a 3-year metastasis free survival rate, or a 3-year disease specific survival rate of greater than 50%, 55%, 60%, 65%, 70%, 75%, 80%, 85%, 90%, 95%, or more than 95%, and high risk refers to a 3-year relapse-free survival rate, a 3-year metastasis free survival rate, or a 3-year disease specific survival rate of less than 50%, 45%, 40%, 35%, 30%, 25%, 20%, 15%, 10%, 5%, or less than 5%. Class 1, Class 2A, or Class 2B risk of metastasis, as used herein, includes low-risk (Class 1; for example having a recurrence risk of less than 25%, 20%, 15%, 10%, 5%, or less than 5%), moderate risk (Class 2A; for example having a recurrence risk of 75%, 70%, 65%, 60%, 55%, 50%, 45%, 40%, 35%, 30%, 25%, or any number in between) or high-risk (Class 2B; for example, having a recurrence risk of 50, 75%, 80%, 85%, 90%, 95%, or higher than 95%) of metastasis according to any of the statistical methods disclosed herein. In certain embodiments, a low risk (Class 1) cSCC tumor has about a 0-10% risk for metastasis, a patient having a moderate risk (Class 2A) cSCC tumor has about a 10-49% risk for metastasis, and a patient having a high risk (Class 2B) cSCC tumor has about a 50-100% risk for metastasis.

In certain embodiments, risk stratifications may be binned, for example a group with an arbitrary designation Class 1 may be selected based on recurrence risk of less than 25%, 20%, 15%, 10%, 5%, or less than 5%. A group with arbitrary designation Class 2A may be selected based on a risk of 75%, 70%, 65%, 60%, 55%, 50%, 45%, 40%, 35%, 30%, 25%, or any number in between. A group with arbitrary designation Class 2B may be selected based on a risk of 75%, 80%, 85%, 90%, 95%, or higher than 95%. These Class designations may comprise more than three groups or as few as two groups depending on the separation characteristics of the predictive algorithm. A person familiar with the art will be able to determine the optimal binning strategy depending on the distributions of Class probability scores developed by modeling.

The term "distant metastasis" or "distal metastasis" as used herein, refers to metastases from a primary cSCC tumor that are disseminated widely. Patients with distant metastases require aggressive treatments, which can eradicate metastatic cSCC, prolong life, and/or cure some patients. In certain embodiments, a low risk (Class 1) cSCC tumor has about a 0-10% risk for distant metastasis, a patient having a moderate risk (Class 2A) cSCC tumor has about a 10-49% risk for distant metastasis, and a patient having a high risk (Class 2B) cSCC tumor has about a 50-100% risk for distant metastasis.

As used herein, the terms "local metastasis" and "local recurrence" can be used interchangeably and refer to cancer cells that have spread to tissue immediately surrounding the primary cSCC tumor or were not completely ablated or removed by previous treatment or surgical resection. Local recurrences are typically resistant to chemotherapy and radiation therapy. Local recurrence can be difficult to control and/or treat if: (1) the primary cSCC tumor is located or involves a vital organ or structure that limits the potential for treatment; (2) recurrence after surgery or other therapy occurs, because while likely not a result from metastasis, high rates of recurrence indicate an advanced cSCC tumor; and (3) presence of lymph node metastases, while rare in cSCC, indicate advanced disease.

In some embodiments, the methods described herein can comprise determining that the cSCC tumor has an increased risk of metastasis or decreased overall survival by combining with clinical staging factors (i.e., risk factors) recommended by, for example, the American Joint Committee on Cancer (AJCC), the Brigham Women's Hospital (BWH), the National Comprehensive Cancer Network (NCCN), the American Academy of Dermatology (AAD), or the American College of Mohs Surgeons (ACMS), to stage the primary cSCC tumor, or other histological features associated with risk of cSCC tumor metastasis or disease-related death.

As used herein, the terms "risk factor" or "clinical staging factors" or "clinicopathologic factor" refer to any staging factor (i.e., risk factor) recommended by, for example, the American Joint Committee on Cancer (AJCC), the Brigham Women's Hospital (BWH), the National Comprehensive Cancer Network (NCCN), the American Academy of Dermatology (AAD), or the American College of Mohs Surgeons (ACMS), to stage the primary cSCC tumor, or other histological features associated with risk of cSCC tumor metastasis or disease-related death. For example, a risk factors can include, but are not limited to tumor size (any size on the head, neck, genitalia, hands, feet or pretibial surface (Areas H or M), or ≥2 cm size (or ≥1 cm if keratoacanthoma type) on any other area of the body (Area L)), tumor location, immune status, perineural involvement (PNI; large (>0.1 mm), named nerve involvement, <0.1 mm in caliber, or unknown), depth of invasion (for example, any one or combination of: invasion beyond subcutaneous fat; depth≥2 mm; and/or Clark level≥IV), differentiation (i.e., poorly differentiated tumor histology), histological subtype (for example aggressive histological subtypes, which can be for example, any of acantholytic, adenosquamous, desmoplastic, sclerosing, basosquamous, small cell, spindle cell, infiltrating, clear cell, lymphoepithelial, sarcomatoid, or metaplastic subtypes), and lymphovascular invasion (see also Table 16). Tumor location definitions can be assigned according to the National Comprehensive Cancer Network (NCCN) Guidelines. For example, Area H, 'mask areas' of face (central face, eyelids, eyebrows, periorbital, nose, lips [cutaneous and vermillion], chin, mandible, preauricular and postauricular skin/sulci, temple, and ear), genitalia, hands, and feet; Area M, cheeks, forehead, scalp, neck, and pretibia; and Area L, trunk and extremities (excluding hands, nail units, pretibial, ankles, and feet). Immune status can refer to immunosuppressed, and types of immunosuppression can include patients that had an organ transplant, or have leukemia, lymphoma, or HIV.

As used herein, the terms "cutaneous squamous cell carcinoma" or "cSCC" or "SCC" refer to any cutaneous squamous cell carcinoma, regardless of tumor size, in patients without clinical or histologic evidence of regional or distant metastatic disease. A cutaneous squamous cell carcinoma sample may be obtained through a variety of sampling methods such as punch biopsy, shave biopsy, surgical excision (including Mohs micrographic surgery and wide local excision, or similar technique), core needle biopsy, incisional biopsy, endoscope ultrasound (EUS) guided-fine needle aspirate (FNA) biopsy, percutaneous biopsy, and other means of extracting RNA from the primary cSCC tumor. A carcinoma is a type of cancer that develops from epithelial cells. Specifically, a carcinoma is a cancer that begins in a tissue that lines the inner or outer surfaces of the body, and that arises from cells originating in the endodermal, mesodermal, and ectodermal germ layer during embryogenesis. Squamous cell carcinomas have observable features and characteristics indicative of squamous differentiation (e.g., intercellular bridges, keratinization, squamous pearls). The most recognized risk factor for cSCC is exposure to sunlight; thus, most cSCC tumors develop on sun-exposed skin sites, for example, the head or neck area. They can also be found on the face, ears, lips, trunk, arms, legs, hands, or feet. Squamous cell carcinoma is the second most common skin cancer.

As used herein, "overall survival" (OS) refers to the percentage of people in a study or treatment group who are still alive for a certain period of time after they were diagnosed with or started treatment for a disease, such as cancer. The overall survival rate for cSCC is often stated as a three-year survival rate, which is the percentage of people in a study or treatment group who are alive three years after their diagnosis or the start of treatment.

The phrase "measuring the gene-expression levels" or "determining the gene-expression levels," as used herein, refers to determining or quantifying RNA or proteins expressed by the gene or genes. The term "RNA" includes mRNA transcripts, and/or specific spliced variants of mRNA. The term "RNA product of the gene," as used herein, refers to RNA transcripts transcribed from the gene and/or specific spliced variants. In some embodiments, mRNA is converted to cDNA before the gene expression levels are measured. With respect to proteins, gene expression refers to proteins translated from the RNA transcripts transcribed from the gene. The term "protein product of the gene" refers to proteins translated from RNA products of the gene. A number of methods can be used to detect or quantify the level of RNA products of the gene or genes within a sample, including microarrays, Real-Time PCR (RT-PCR; including quantitative RT-PCR), nuclease protection assays, RNA-sequencing (RNA-seq), and Northern blot analyses. In one embodiment, the assay uses the APPLIED BIOSYSTEMS™ HT7900 fast Real-Time PCR system. In addition, a person skilled in the art will appreciate that a number of methods can be used to determine the amount of a protein product of a gene of the methods disclosed herein, including immunoassays such as Western blots, ELISA, and immunoprecipitation followed by SDS-PAGE and immunocytochemistry. In certain embodiments, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR).

A person skilled in the art will appreciate that a number of detection agents can be used to determine gene expression. For example, to detect RNA products of the biomarkers, probes, primers, complementary nucleotide sequences, or nucleotide sequences that hybridize to the RNA products can be used. In another example, to detect cDNA products of the biomarkers, probes, primers, complementary nucleotide sequences, or nucleotide sequences that hybridize to the cDNA products can be used. To detect protein products of the biomarkers, ligands or antibodies that specifically bind to the protein products can be used.

As used herein, the term "hybridize" refers to the sequence specific non-covalent binding interaction with a complementary nucleic acid. In one embodiment, the hybridization is under high stringency conditions. Appropriate stringency conditions that promote hybridization are known to those skilled in the art.

As used herein, the terms "probe" and "primer" refer to a nucleic acid sequence that will hybridize to a nucleic acid target sequence. In one example, the probe and/or primer hybridizes to an RNA product of the gene or a complementary nucleic acid sequence. In another example, the probe and/or primer hybridizes to a cDNA product. The length of probe or primer depends on the hybridizing conditions and the sequences of the probe or primer and nucleic acid target sequence. In one embodiment, the probe or primer is at least 8, 10, 15, 20, 25, 50, 75, 100, 150, 200, 250, 400, 500, or more than 500 nucleotides in length. Probes and/or primers may include one or more label. Probes and/or primers may be commercially sourced from various providers (e.g., ThermoFisher Scientific). In certain embodiments, a label may be any substance capable of aiding a machine, detector, sensor, device, or enhanced or unenhanced human eye from differentiating a labeled composition from an unlabeled composition. Examples of labels include, but are not limited to, a radioactive isotope or chelate thereof, dye (fluorescent or non-fluorescent), stain, enzyme, or nonradioactive metal. Specific examples include, but are not limited to, fluorescein, biotin, digoxigenin, alkaline phosphates, biotin, streptavidin, $^3$H, $^{14}$C, $^{32}$P, $^{35}$S, or any other compound capable of emitting radiation, rhodamine, 4-(4'-dimethylamino-phenylazo)benzoic acid; 4-(4'-dimethylamino-phenylazo)sulfonic acid (sulfonyl chloride); 5-((2-aminoethyl)-amino)-naphtalene-1-sulfonic acid; Psoralene derivatives, haptens, cyanines, acridines, fluorescent rhodol derivatives, cholesterol derivatives; ethylene-diamine-tetra-acetic acid and derivatives thereof, or any other compound that may be differentially detected. The label may also include one or more fluorescent dyes. Examples of dyes include, but are not limited to, CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.

As used herein, a "sequence detection system" is any computational method in the art that can be used to analyze the results of a PCR reaction. One example is the APPLIED BIOSYSTEMS™ HT7900 fast Real-Time PCR system. In certain embodiments, gene expression can be analyzed using, e.g., direct DNA expression in microarray, Sanger sequencing analysis, Northern blot, the NANOSTRING® technology, serial analysis of gene expression (SAGE), RNA-seq, tissue microarray, or protein expression with immunohistochemistry or western blot technique. PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured. In one embodiment, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR).

As used herein, the terms "differentially expressed" or "differential expression" refer to a difference in the level of expression of the genes that can be assayed by measuring the level of expression of the products of the genes, such as the difference in level of messenger RNA transcript expressed (or converted cDNA) or proteins expressed of the genes. In one embodiment, the difference can be statistically significant. The term "difference in the level of expression" refers to an increase or decrease in the measurable expression level of a given gene as measured by the amount of messenger RNA transcript (or converted cDNA) and/or the amount of protein in a sample as compared with the measurable expression level of a given gene in a control, or control gene or genes in the same sample (for example, a non-recurrence sample). In another embodiment, the differential expression can be compared using the ratio of the level of expression of a given gene or genes as compared with the expression level of the given gene or genes of a control, wherein the ratio is not equal to 1.0. For example, an RNA, cDNA, or protein is differentially expressed if the ratio of the level of expression in a first sample as compared with a second sample is greater than or less than 1.0. For example, a ratio of greater than 1, 1.2, 1.5, 1.7, 2, 3, 3, 5, 10, 15, 20, or more than 20, or a ratio less than 1, 0.8, 0.6, 0.4, 0.2, 0.1, 0.05, 0.001, or less than 0.0001. In yet another embodiment, the differential expression is measured using p-value. For instance, when using p-value, a biomarker is identified as being differentially expressed as between a first sample and a second sample when the p-value is less than 0.1, less than 0.05, less than 0.01, less than 0.005, or less than 0.001.

The terms "increased expression" or "decreased expression," as used herein, refer to an expression level of one or more genes, or prognostic RNA transcripts, or their corresponding cDNAs, or their expression products that has been found to be differentially expressed in recurrent versus non-recurrent cSCC tumors. The higher the expression level of a gene that predominantly has increased expression in tumors of patients who had recurrence, the higher is the likelihood that the patient suffering from this tumor is expected to have a poor clinical outcome (i.e., higher risk of recurrence, metastasis, or both). In contrast, the lower the expression level of a gene that predominantly has increased expressed in tumors of patients who have recurrent tumors, the higher is the likelihood that the patient suffering from this tumor is expected to have a promising clinical outcome (i.e., decreased risk of recurrence, metastasis, or both). The lower the expression level of a gene that predominantly has decreased expression in tumors of patients who had recurrence, the higher is the likelihood that the patient suffering from this tumor is expected to have a poor clinical outcome (i.e., higher risk of recurrence, metastasis, or both). In contrast, the higher the expression level of a gene that predominantly has decreased expressed in tumors of patients who have recurrent tumors, the higher is the likelihood that the patient suffering from this tumor is expected to have a promising clinical outcome (i.e., decreased risk of recurrence, metastasis, or both).

References herein to the "same" level of biomarker indicate that the level of biomarker measured in each sample is identical (i.e., when compared to the selected reference). References herein to a "similar" level of biomarker indicate that levels are not identical but the difference between them is not statistically significant (i.e., the levels have comparable quantities).

As used herein, the terms "control" and "standard" refer to a specific value that one can use to determine the value obtained from the sample. In one embodiment, a dataset may be obtained from samples from a group of subjects known to have a cutaneous squamous cell carcinoma or subtype. The expression data of the genes in the dataset can be used to create a control (standard) value that is used in testing samples from new subjects. In such an embodiment, the "control" or "standard" is a predetermined value for each gene or set of genes obtained from subjects with a cutaneous squamous cell carcinoma whose gene expression values and tumor types are known. In certain embodiments of the methods disclosed herein, non-limiting examples of control genes can include, but are not limited to, BAG6 (probe ID: Hs00190383), KMT2D/MLL2 (probe ID: Hs00912419_m1), MDM2 (probe ID: Hs00540450_s1), FXR1 (probe ID: Hs01096876_g1), KMT2C (probe ID: Hs01005521_m1), MDM4 (probe ID: Hs00967238_m1), VIM, and NF1B. In certain embodiments of the methods disclosed herein, the control genes are BAG6 (probe ID: Hs00190383), KMT2D/MLL2 (probe ID: Hs00912419_m1), MDM2 (probe ID: Hs00540450_s1), FXR1 (probe ID: Hs01096876_g1), KMT2C (probe ID: Hs01005521_m1), and MDM4 (probe ID: Hs00967238_m1). In some embodiments, a control population may comprise healthy individuals, individuals with cancer, or a mixed population of individuals with or without cancer. In certain embodiments, a control population may comprise individuals with non-metastatic cancer or cancer that did not recur.

As used herein, the term "normal" when used with respect to a sample population refers to an individual or group of individuals that does/do not have a particular disease or condition (e.g., cSCC or recurrent cSCC) and is also not suspected of having or being at risk for developing the disease or condition. The term "normal" is also used herein to qualify a biological specimen or sample (e.g., a biological fluid) isolated from a normal or healthy individual or subject (or group of such subjects), for example, a "normal control sample." The "normal" level of expression of a marker is the level of expression of the marker in cells in a similar environment or response situation, in a patient not afflicted with cancer. A normal level of expression of a marker may also refer to the level of expression of a "reference sample" (e.g., a sample from a healthy subject not having the marker associated disease). A reference sample expression may be comprised of an expression level of one or more markers from a reference database. Alternatively, a "normal" level of expression of a marker is the level of expression of the marker in non-tumor cells in a similar environment or response situation from the same patient that the tumor is derived from.

As used herein, the terms "gene-expression profile," "GEP," or "gene-expression profile signature" refer to any combination of genes, the measured messenger RNA transcript expression levels, cDNA levels, or direct DNA/RNA expression levels, or immunohistochemistry levels of which can be used to distinguish between two biologically different corporal tissues and/or cells and/or cellular changes. In certain embodiments, a gene-expression profile is comprised of the gene-expression levels of 34 discriminant genes of ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839. In some embodiments, the gene set further comprises 6 control genes or normalization genes selected from: BAG6 (probe ID: Hs00190383), KMT2D/MLL2 (probe ID: Hs00912419_m1), MDM2 (probe ID: Hs00540450_s1), FXR1 (probe ID: Hs01096876_g1), KMT2C (probe ID: Hs01005521_m1), MDM4 (probe ID: Hs00967238_m1), VIM, and NF1B. In certain embodiments of the methods disclosed herein, the 6 control genes are BAG6 (probe ID: Hs00190383), KMT2D/MLL2 (probe ID: Hs00912419_m1), MDM2 (probe ID: Hs00540450_s1), FXR1 (probe ID: Hs01096876_g1), KMT2C (probe ID: Hs01005521_m1), and MDM4 (probe ID: Hs00967238_m1).

In certain embodiments, a gene-expression profile is comprised of the gene-expression levels of at least 140, 139, 138, 137, 136, 135, 134, 133, 132,131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 genes, or less than 10 genes. In one embodiment, the gene-expression profile is comprised of 56 genes. In another embodiment, the gene-expression profile is comprised of 40 genes. In another embodiment, the gene-expression profile is comprised of 30 genes. In another embodiment, the gene-expression profile is comprised of 20 genes. In certain embodiments, the genes selected are: ACSBG1, AIM2, ALOX12, ANXA9, APOBEC3G, ARPC2, ATP6AP1, ATP6V0E2, BBC, BHLHB9, BLOC1 S1, ClQL4, C21orf59, C3orf70, CCL27, CD163, CEP76, CHI3L1, CHMP2B, CXCL10, CXCR4, CYP2D6 (LOC101929829), DARS, DCT, DDAH1, DSS1, DUXAP8, EGFR, EphB2, FCHSD1, FDFT1, FLG, FN1, GTPBP2, HDDC3, HNRNPL, HOXA10 (HOXA9, MIR196B), HPGD, ID2, IL24, IL2RB, IL7R, INHBA, IPO5P1, KIT, KLK5, KRT17, KRT18, KRT19, KRT6B, LAMC2, LCE2B, LIME1 (ZGPAT), LOC100287896, LOC101927502, LOR, LRRC47, MIER2, MIR129-1, MIR3916, MKLN1, MMP1, MMP10, MMP12, MMP13, MMP3, MMP7, MMP9, MRC1, MRPL21, MSANTD4, MYC, NEB, NEFL, NFASC, NFIA, NFIB, NFIC, NOA1, PD1, PDL1, PDPN, PI3, PIG3, PIGBOS1, PIM2, PLAU, PLS3, PTHLH, PTRHD1, RBM33, RCHY1, RNF135, RPL26L1, RPP38, RUNX3, S100A8, S100A9, SEPT3, SERPINB2, SERPINB4, SLC1A3, SLC25A11, SNORD124, SPATA41, SPP1, TAF6L, TFAP2B, THYN1, TMEM41B, TNNC1, TUBB3, TUFM (MIR4721), TYRP1, UGP2, USP7, VIM, YKT6, ZNF48, ZNF496, ZNF839, and/or ZSCAN31. In other embodiments, the gene set comprises 20 genes, 30 genes, or 40 genes selected from the genes listed above. In some embodiments, the gene set further comprises control genes or normalization genes selected from: BAG6 (probe ID: Hs00190383), KMT2D/MLL2 (probe ID: Hs00912419_m1), MDM2 (probe ID: Hs00540450_s1), FXR1 (probe ID: Hs01096876_g1), KMT2C (probe ID: Hs01005521_m1), MDM4 (probe ID: Hs00967238_m1), VIM, and NF1B.

As used herein, the term "predictive training set" refers to a cohort of cSCC tumors with known clinical outcome for metastasis (i.e., local recurrence, regional metastasis, distant metastasis, or any combination) and known genetic expression profile, used to define or establish all other cSCC tumors, based upon the genetic expression profile of each, as a low-risk, Class 1 tumor type or a high-risk, Class 2 tumor type. Additionally, included in the predictive training set is the definition of "threshold points," which are points at which a classification of metastatic risk is determined, specific to each individual gene expression level.

As used herein, the term "altered in a predictive manner" refers to changes in genetic expression profile that predict metastasis (i.e., local recurrence, regional metastasis, distant metastasis, or any combination), or predict overall survival. Predictive modeling risk assessment can be measured as: 1) a binary outcome having risk of metastasis or overall survival that is classified as low risk (e.g., termed Class 1 herein) vs. high risk (e.g., termed Class 2 herein; wherein Class 2A is a high risk/moderate risk, and Class 2B is the highest risk); and/or 2) a linear outcome based upon a probability score from 0 to 1 that reflects the correlation of the genetic expression profile of a cSCC tumor with the genetic expression profile of the samples that comprise the training set used to predict risk outcome. Within the probability score range from 0 to 1, a probability score, for example, of less than 0.5 reflects a tumor sample with a low risk of metastasis (i.e., local recurrence, regional metastasis, distant metastasis, or any combination), or death from disease, while a probability score, for example, of greater than 0.5 reflects a tumor sample with a high risk of metastasis (i.e., local recurrence, regional metastasis, distant metastasis, or any combination), or death from disease. The increasing probability score from 0 to 1 reflects incrementally declining metastasis free survival. In one embodiment, the probability score is a bimodal, two-Class analysis, wherein a patient having a value of between 0 and 0.499 is designated as Class 1 (low risk; for example, having a 3-year relapse-free survival rate, a 3-year metastasis free survival rate, or a 3-year disease specific survival rate of greater than 50%, 55%, 60%, 65%, 70%, 75%, 80%, 85%, 90%, 95%, or more than 95%) and a patient having a value of between 0.500 and 1.00 is designated as Class 2 (high risk; for example, having a 3-year metastasis free survival rate, or a 3-year disease specific survival rate of less than 50%, 45%, 40%, 35%, 30%, 25%, 20%, 15%, 10%, 5%, or less than 5%).

In certain embodiments, the probability score is a trimodal, three-Class analysis, wherein patients are designated as Class 1 (low risk; for example having a recurrence risk of less than 25%, 20%, 15%, 10%, 5%, or less than 5%), Class 2A (moderate risk; for example having a recurrence risk of 75%, 70%, 65%, 60%, 55%, 50%, 45%, 40%, 35%, 30%, 25%, or any number in between), or Class 2B (high risk; for example, having a recurrence risk of 75%, 80%, 85%, 90%, 95%, or higher than 95%). To develop a ternary, or three-Class system of risk assessment, with Class 1 having a low risk of metastasis (i.e., local recurrence, regional metastasis, distant metastasis, or any combination) or death from disease, Class 2A having an moderate risk, and Class 2B having a high risk, the median probability score value for all low risk or high risk tumor samples in the training set was determined, and one standard deviation from the median was established as a numerical boundary to define low or high risk. For example, low risk cSCC tumors within the ternary classification system can have a 3-year metastasis free survival of 100% (e.g., Class 1; with a probability score of 0-0.337), compared to high risk (e.g., Class 2B; with a probability score of 0.673-1) cSCC tumors which can have a 20% 3-year metastasis free survival. Cases falling outside of one standard deviation from the median low or high risk probability scores have an moderate risk, and moderate risk (Class 2A; with a probability score of 0.338-0.672) cSCC tumors can have a 55% 3-year metastasis free survival rate.

The TNM (Tumor-Node-Metastasis) status system is the most widely used cancer staging system among clinicians and is maintained by the American Joint Committee on Cancer (AJCC) and the International Union for Cancer Control (UICC). Cancer staging systems codify the extent of cancer to provide clinicians and patients with the means to quantify prognosis for individual patients and to compare groups of patients in clinical trials and who receive standard care around the world.

Local recurrence rates for cSCC have been reported to be 1-10%, but can be as high as 47% in patients who have cSCCs with high-risk clinical features. While the overall rate of metastasis is ~5%, this rate increases up to ~45% in patients with high-risk clinical features or who have already experienced a recurrence. After regional or distant metastasis occurs, prognosis is usually poor, with 5-year survival rates ranging from 26-34% and 10-year survival rates of 16%. Although the overall percentages of patients who die from cSCC (~1%) are low, the absolute number of deaths are estimated to be equal to or greater than those attributed to melanoma, due to the large number of yearly cSCC diagnoses (400,000-700,000 patients), and account for the majority of NMSC-related deaths. In effect, local and regional recurrence from primary cSCC tumors remains a significant health burden.

Cutaneous squamous cell carcinoma stems from interfollicular epidermal keratinocytes and can arise from precancerous lesions, the most common of which are actinic keratoses. Once the malignant cells enter the dermis, the cSCC becomes invasive. Squamous cell carcinoma can present as smooth or hyperkeratinized lesions that are pink or skin-colored. They can exhibit ulceration and bleed when traumatized. Risk factors that contribute to the development of cSCC include exposures to ultraviolet radiation, ionizing radiation, and chemicals, as well as increased age and male gender. Immunosuppressed individuals, those with a history of non-Hodgkin lymphoma, including chronic lymphocytic leukemia, those with certain genetic skin conditions, and those who have had organ transplants are at a significantly increased risk for developing cSCC. In fact, the latter group has risk up to 100 times that of the normal population. Some drugs used to treat other types of skin cancer (e.g., basal cell carcinoma (BCC), melanoma), including hedgehog, BRAF, and MET inhibitors, can also increase the propensity for cSCC. Small, low-risk lesions can be treated with cryosurgery, curettage and electrodessication, or surgery, while larger, higher risk lesions are generally treated with surgical excision or Mohs surgery. Radiotherapy can be used in conjunction with surgery if margins are not cleared surgically or if there is perineural invasion. If regional recurrence occurs, the lymph nodes are the primary site of involvement, accounting for ~80-85% of cSCC recurrences, while distant metastasis occurs in ~15-20% of patients.

Because the development of regional or distant metastasis leads to an increase death from cSCC and because there are effective adjuvant interventions, there has been an increased interest in more accurately identifying such lesions beyond clinical and pathologic features alone. As such, the National Comprehensive Cancer Network (NCCN) and American Joint Committee on Cancer (AJCC) have recently proposed parameters to distinguish high risk lesions and follow-up measures for these lesions. These high-risk features include tumor size and location ("mask" areas of the face and/or ear and non-glabrous lip), increased thickness or Clark's level, immunosuppression, recurrent lesions, sites of chronic inflammation or previous radiation, poor differentiation, and perineural invasion. However, high-risk cSCC definitions from different groups are discordant, with the AJCC classifying a majority of lesions as low-risk and NCCN classifying a majority as high-risk. Such discrepancies, especially in the T2a and T2b groups, have led to the proposal of alternative staging criteria that can better elucidate high risk cSCC cases. However, in an attempt to improve the positive predictive values, these alternative approaches have a lower sensitivity and categorize many patients who will metastasize as low risk. In effect, there is a clinically unmet need for better markers to identify high-risk lesions, particularly molecular biomarkers that can be objectively evaluated. The validated prognostic gene expression profiles disclosed herein could inform clinical decision-making on, for example: (1) preoperative surgical staging, based on shave biopsy; (2) adjuvant radiation, nodal staging, adjuvant systemic therapy to reduce regional/distant metastasis; and (3) improving identification of patients with cSCC who can benefit from surgical, radiation and immunotherapy interventions.

Squamous cell carcinoma that is predicted to have an increased risk of recurrence, progression, or metastasis can be treated with an aggressive cancer treatment regimen (see NCCN Guidelines® v1. 2020-October 2019). Advanced cSCC may be defined under two headings: (1) local disease; and/or (2) regional nodal/distant metastases. Local disease can be difficult to control and/or treat if: (1) the primary cSCC has invaded into neuronal or vascular structures; (2)

there is presence of lymph node metastases, which indicate advanced disease; or (3) distant metastases have been detected.

In an embodiment, a method for predicting risk of metastasis (i.e., recurrence, regional metastasis, distant metastasis, or any combination), in a patient with a cutaneous squamous cell carcinoma (cSCC) tumor is disclosed herein, the method comprising: (a) obtaining a cSCC tumor sample from the patient and isolating mRNA from the sample; (b) determining the expression level of 34 genes in a gene set; wherein the 34 genes in the gene set are selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839; (c) comparing the expression levels of the 34 genes in the gene set from the cSCC tumor sample to the expression levels of the 34 genes in the gene set from a predictive training set to generate a probability score of the risk of metastasis (local recurrence, regional metastasis, distant metastasis, or any combination); and (d) providing an indication as to whether the cSCC tumor has a low risk to a high risk of local metastasis (recurrence, regional metastasis, distant metastasis, or any combination), based on the probability score generated in step (c).

In some embodiments, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR). In certain embodiments, the cSCC tumor sample is obtained from formalin-fixed, paraffin embedded sample. In one embodiment, the method further comprises identifying the cSCC tumor as having a high risk of metastasis (i.e., local recurrence, regional metastasis, distant metastasis, or any combination), based on the probability score, and administering to the patient an aggressive tumor treatment.

In another embodiment, the gene set comprises at least one additional gene selected from the genes AIM2, ANXA9, ARPC2, ATP6AP1, BLOC1S1, ClQL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

In an embodiment, a method for predicting risk of metastasis (i.e., recurrence, metastasis, or both), in a patient with a cutaneous squamous cell carcinoma (cSCC) tumor is disclosed herein, the method comprising: (a) obtaining a cSCC tumor sample from the patient and isolating mRNA from the sample; (b) determining the expression level of 34 genes in a gene set; wherein the 34 genes in the gene set are selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839; and (c) providing an indication as to whether the cSCC tumor has a low risk to a high risk of metastasis (i.e., local recurrence, regional metastasis, distant metastasis, or any combination), based on the expression level of 34 genes generated in step (b).

In some embodiments, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR). In certain embodiments, the cSCC tumor sample is obtained from formalin-fixed, paraffin embedded sample.

In another embodiment, the gene set comprises at least one additional gene selected from the genes AIM2, ANXA9, ARPC2, ATP6AP1, BLOC1S1, ClQL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

In certain embodiments, the expression level of: ACSBG1 is decreased, AIM2 is increased, ALOX12 is decreased, ANXA9 is decreased, APOBEC3G is increased, ARPC2 is decreased, ATP6AP1 is decreased, ATP6V0E2 is increased, BBC is increased, BHLHB9 is decreased, BLOC1S1 is decreased, C1QL4 is increased, C21orf59 is increased, C3orf70 is increased, CCL27 is decreased, CD163 is increased, CEP76 is decreased, CHI3L1 is increased, CHMP2B is decreased, CXCL10 is decreased, CXCR4 is increased, CYP2D6 (LOC101929829) is decreased, DARS is decreased, DCT is decreased, DDAH1 is decreased, DSS1 is decreased, DUXAP8 is increased, EGFR is increased, EphB2 is increased, FCHSD1 is decreased, FDFT1 is decreased, FLG is decreased, FN1 is increased, GTPBP2 is decreased, HDDC3 is increased, HNRNPL is decreased, HOXA10 (HOXA9, MIR196B) is decreased, HPGD is decreased, ID2 is decreased, IL24 is increased, IL2RB is decreased, IL7R is increased, INHBA is increased, IPO5P1 is increased, KIT is increased, KLK5 is decreased, KRT17 is decreased, KRT18 is increased, KRT19 is decreased, KRT6B is decreased, LAMC2 is decreased, LCE2B is decreased, LIME1 (ZGPAT) is increased, LOC100287896 is increased, LOC101927502 is decreased, LOR is decreased, LRRC47 is increased, MIER2 is increased, MIR129-1 is increased, MIR3916 is increased, MKLN1 is increased, MMP1 is increased, MMP10 is decreased, MMP12 is increased, MMP13 is increased, MMP3 is increased, MMP1 is increased, MMP9 is decreased, MRC1 is increased, MRPL21 is increased, MSANTD4 is decreased, MYC is decreased, NEB is decreased, NEFL is decreased, NFASC is decreased, NFIA is decreased, NFIB is decreased, NFIC is decreased, NOA1 is increased, PD1 is decreased, PDL1 is increased, PDPN is increased, PI3 is decreased, PIG3 is decreased, PIGBOS1 is increased, PIM2 is increased, PLAU is increased, PLS3 is decreased, PTHLH is decreased, PTRHD1 is decreased, RBM33 is increased, RCHY1 is increased, RNF135 is increased, RPL26L1 is increased, RPP38 is decreased, RUNX3 is increased, S100A8 is decreased, S100A9 is decreased, SEPT3 is decreased, SERPINB2 is decreased, SERPINB4 is decreased, SLC1A3 is increased, SLC25A11 is increased, SNORD124 is increased, SPATA41 is increased, SPP1 is increased, TAF6L is increased, TFAP2B is decreased, THYN1 is increased, TMEM41B is decreased, TNNC1 is decreased, TUBB3 is decreased, TUFM (MIR4721) is increased, TYRP1 is decreased, UGP2 is decreased, USP7 is decreased, VIM is increased, YKT6 is increased, ZNF48 is increased, ZNF496 is increased, ZNF839 is increased, and/or ZSCAN31 is decreased. In certain embodiments, the increase or decrease in the expression level is the gene level from a recurrent tumor sample versus a non-recurrent tumor sample.

In an embodiment, a method for treating a patient with cutaneous squamous cell carcinoma (cSCC) tumor is disclosed herein, the method comprising: (a) obtaining a cSCC tumor sample from the patient and isolating mRNA from the sample; (b) determining the expression level of 34 genes in a gene set; wherein the 34 genes in the gene set are selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839; (c) providing an indication as to whether the cSCC tumor has a low risk to a high risk of local metastasis (i.e., recurrence, regional metastasis, distant metastasis, or any combination), based on the expression level of 34 genes generated in step (b); and (d) administering to the patient an aggressive treatment when the determination is made in the affirmative that the patient has a cSCC tumor with a high risk of metastasis (i.e., local recurrence, regional metastasis, distant metastasis, or any combination).

In some embodiments, the expression level of each gene in the gene set is determined by reverse transcribing the isolated mRNA into cDNA and measuring a level of fluorescence for each gene in the gene set by a nucleic acid sequence detection system following Real-Time Polymerase Chain Reaction (RT-PCR). In certain embodiments, the cSCC tumor sample is obtained from formalin-fixed, paraffin embedded sample.

In another embodiment, the gene set comprises at least one additional gene selected from the genes AIM2, ANXA9, ARPC2, ATP6AP1, BLOC1S1, C1QL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

As used herein, the terms "treatment," "treat," or "treating" refer to a method of reducing the effects of a disease or condition or symptom of the disease or condition. Thus, in the methods disclosed herein, treatment can refer to a 5%, 10%, 20%, 30%, 40%, 50%, 60%, 70%, 80%, 90%, or 100% reduction in the severity of an established disease or condition or symptom of the disease or condition. For example, a method of treating a disease is considered to be a treatment if there is a 5% reduction in one or more symptoms of the disease in a subject as compared to a control. Thus, the reduction can be a 5%, 10%, 20%, 30%, 40%, 50%, 60%, 70%, 80%, 90%, 100% or any percent reduction between 5% and 100% as compared to native or control levels. It is understood that treatment does not necessarily refer to a cure or complete ablation of the disease, condition, or symptoms of the disease or condition. After a cSCC is found and staged, a medical professional or team of medical professionals will recommend one or several treatment options. In determining a treatment plan, factors to consider include the type, location, and stage of the cancer, as well as the patient's overall physical health. Patients with cSCC typically are managed by a health care team made up of doctors from different specialties, such as: a dermatologist (in particular, a dermatologist who specializes in Mohs micrographic surgery), an orthopedic surgeon (in particular, a surgeon who specializes in diseases of the bones, muscles, and joints), a surgical oncologist, a thoracic surgeon, a medical oncologist, a radiation oncologist, and/or a physiatrist (or rehabilitation doctor). After a cSCC is found and staged, a medical professional or team of medical professionals will typically recommend one or several treatment options including one or more of surgery, radiation, chemotherapy, and targeted therapy.

The NCCN Guidelines® define low risk cSCC tumors as tumors that involve: (1) an area of less than 20 mm (for truck and extremities) or less than 10 mm for the cheeks, forehead, scalp, neck and pretibial; (2) well defined borders; (3) primary cSCC tumor; (4) not rapidly growing; (5) from a patient who has no neurologic symptoms and is not considered immunosuppressed; (6) from a site free of chronic inflammation; (7) well or moderately differentiated; (8) free of acantholytic, adenosquamous, desmoplastic, or metaplastic subtypes; (9) depths of less than 2 mm; and (10) free of perineural, lymphatic, or vascular involvement.

The NCCN Guidelines® define high risk cSCC tumors as tumors that involve: (1) an area of greater than 20 mm (for trunk and extremities), greater than 10 mm for the cheeks, forehead, scalp, neck and pretibial, or any cSCC involving the "mask areas" (such as central face, eyelids, eyebrows, periorbital, nose, lips, chin, mandible, temple or ear), genitalia, hands and feet; (2) poorly defined borders; (3) recurrent cSCC tumor; (4) rapidly growing; (5) from a patient who has neurologic symptoms or is considered immunosuppressed; (6) from a site with chronic inflammation; (7) poorly differentiated; (8) presence of acantholytic, adenosquamous, desmoplastic, or metaplastic subtypes; (9) depths of greater than or equal 2 mm; and (10) presence of perineural, lymphatic, or vascular involvement.

As used herein, the term "aggressive cancer treatment regimen" refers to a treatment regimen that is determined by a medical professional or team of medical professionals and can be specific to each patient. In certain embodiments, a cSCC tumor predicted to have a high-risk of recurrence or a high-risk of metastasis, or a decreased chance of survival using the methods and kits disclosed herein, would be treated using an aggressive cancer treatment regimen. Whether a treatment is considered to be aggressive will generally depend on the cancer-type, the age of the patient, and other factors known to those of skill in the art. For example, in breast cancer, adjuvant chemotherapy is a common aggressive treatment given to complement the less aggressive standards of surgery and hormonal therapy. Those skilled in the art are familiar with various other aggressive and less aggressive treatments for each type of cancer. An aggressive cancer treatment regimen is defined by the National Comprehensive Cancer Network (NCCN), and has been defined in the NCCN Guidelines® as including one or more of: 1) imaging (CT scan, PET/CT, MRI, chest X-ray), 2) discussion and/or offering of tumor resection if a tumor is determined to be resectable (e.g., by Mohs micrographic surgery or resection with complete circumferential margin assessment), 3) radiation therapy (RT), 4) chemoradiation, 5) chemotherapy, 6) regional limb therapy, 7) palliative surgery, 8) systemic therapy, 9) immunotherapy, and 10) inclusion in ongoing clinical trials. Guidelines for clinical practice are published in the National Comprehensive Cancer Network (NCCN Guidelines® Squamous Cell Skin Cancer Version 2.2018, updated Oct. 5, 2017, available on the World Wide Web at NCCN.org).

Additional therapeutic options may include, but are not limited to: 1) combination regimens such as: AD (doxorubicin, dacarbazine); AIM (doxorubicin, ifosfamide, mesna); MAID (mesna, doxorubicin, ifosfamide, dacarbazine); ifosfamide, epirubicin, mesna; gemcitabine and docetaxel; gemcitabine and vinorelbine; gemcitabine and dacarbazine; doxorubicin and olaratumab; methotrexate and vinblastine; tamoxifen and sulindac; vincristine, dactinomycin, cylclophosphamide; vincristine, doxorubicin, cyclophosphamide; vincristine, doxorubicin, cyclophosphamide with ifosfamide and etoposide; vincristine, doxorubicin, ifosfamide; cyclophosphamide topotecan; or ifosfamide, doxorubicin; and/or 2) single agents, such as: cisplatin or other metallic compounds, 5-FU/capecitabine (Xeloda®), cetuximab (Erbitux®), cemiplimab (Libtayo®), pembrolizumab (MK-3475), panitumumab (Vectibix®), dacomitinib (PF-00299804), gefitinib (ZD1839, Iressa), doxorubicin, ifosfamide, epirubicin, gemcitabine, dacarbazine, temozolomide, vinorelbine, eribulin, trabectedin, pazopanib, imatinib, sunitinib, regorafenib, sorafenib, nilotinib, dasatinib, interferon, toremifene, methotrexate, irinotecan, topotecan, paclitaxel, nab-paclitaxel (abraxane), docetaxel, bevacizumab, temozolomide, sirolimus (Rapamune®), everolimus, temsirolimus, crizotinib, ceritinib, or palbociclib.

While surgical excision remains the mainstay for treating operable (Stage I-III) cSCC patients, for Stage I patients, en bloc resection with negative margins is generally considered sufficient for long-term local control. For those with incomplete excision margins and/or other unfavorable pathologic features, pre- or post-operative chemotherapy and/or radiation treatment can be recommended. No therapy has shown consistent efficacy for the treatment of excised cSCC, and treatment options for unresectable or advanced cSCC are limited.

Immunotherapy using an anti-PD1 inhibitor has shown promising results in early phase studies with cSCC patients. Examples of immunotherapies (that can be used alone or in combination with any one or more of tumor resection if a tumor is determined to be resectable, radiation therapy, chemoradiation, chemotherapy, regional limb therapy, palliative surgery, systemic therapy, additional immunotherapeutic, or inclusion in ongoing clinical trials), can include, for example, pembrolizumab (Keytruda®) and nivolumab (Opdivo®), cemiplimab (Libtayo®; a fully human monoclonal antibody to Programmed Death-1). PD-1 is a protein on T-cells that normally help keep T-cells from attacking other cells in the body. By blocking PD-1, these drugs can boost the immune response against cancer cells. CTLA-4 inhibitors (for example, ipilimumab (Yervoy®)) are another class of drugs that can boost the immune response. In some instances, cytokine therapy (such as, interferon-alpha and interleukin-2) can be used to boost the immune system. Examples of interferon and interleukin-based treatments can include, but are not limited to, aldesleukin (Proleukin®), interferon alpha-2b (INTRON®), and pegylated interferon alpha-2b (Sylvatron®; PEG-INTRON®, PEGASYS). In another embodiment, oncolytic virus therapy can be used. Along with killing the cells directly, the oncolytic viruses can also alert the immune system to attack the cancer cells. For example, talimogene laherparepvec (Imlygic®), also known as T-VEC, is an oncolytic virus that can be used to treat melanomas. Additional immunotherapies may include CV8102.

Additionally, targeted therapies may be used to treat patients with cSCC. For example, targeted therapies can include, but are not limited to, vemurafenib (Zelboraf®), dabrafenib (Tafinlar®), trametinib (Mekinist®), CLL442, and cobimetinib (Cotellic®). These drugs target common genetic mutations, such as the BRAFV600 mutation, that may be found in a subset of cSCC patients.

In certain embodiments, the methods as disclosed herein can be used to determine a recommended risk-aligned management plan. For example, patients determined to have a low risk (Class 1) tumor can be managed under a low intensity management plan. A low intensity management plan can comprise minimal clinical follow-up (e.g., 1-2× per year), a reduced imaging (low frequency or no imaging performed), a reduced nodal assessment (palpation only), and/or an avoidance of adjuvant radiation or chemotherapy. For example, patients determined to have a moderate risk (Class 2A) tumor can be managed under a moderate intensity management plan. A moderate intensity management plan can comprise a high frequency of clinical follow-up (e.g., 2-4× per year for about 3 years), imaging (e.g., baseline and annual nodal US/CT for 2 years), consideration of nodal biopsy or elective neck dissection, and/or a consideration of adjuvant radiation or chemotherapy. For example, patients determined to have a high risk (Class 2B) tumor can be managed under a high intensity management plan. A high intensity management plan can comprise the highest frequency of clinical follow-up (e.g., 4-12× per year for about 3 years), imaging (e.g., baseline and 4× per year nodal US/CT for 2 years), recommendation of nodal biopsy or elective neck dissection, and/or a recommendation of adjuvant radiation, chemotherapy, and/or clinical trials. Importantly, these risk-stratified management plans fall within the current NCCN Guidelines® for patients identified as having a high risk cSCC tumor as defined by clinical and pathologic features only (see also FIG. 15).

As used herein, the term "adjuvant therapy" refers to additional cancer treatment given after a primary treatment to lower the risk that the cancer will recur. For example, adjuvant therapy is often used before and/or after a primary surgical treatment in order to decrease the chance of the primary cancer recurring. In surgery, where all detectable disease has been removed, there remains a statistical risk of relapse or recurrence due to the presence of undetected disease. Adjuvant therapy given before the primary treatment is called neoadjuvant therapy. Neoadjuvant therapy can also decrease the chance of the cancer recurring, and it's often used to make the primary treatment, such as an operation or radiation treatment more effective. Adjuvant therapy can include chemotherapy, radiation therapy, hormone therapy, targeted therapy, immunotherapies, or biological therapy.

In some embodiments, the cSCC tumor is a frozen sample. In another embodiment, the cSCC sample is formalin-fixed and paraffin embedded. In certain embodiments, the cSCC sample is taken from a formalin-fixed, paraffin embedded wide local excision sample. In another embodiment, the cSCC tumor is taken from a formalin-fixed, paraffin embedded primary biopsy sample. In some embodiments, the cSCC sample can be from image guided surgical biopsy, shave biopsy, wide excision, or a lymph node dissection.

In certain embodiments, analysis of genetic expression and determination of outcome is carried out using radial basis machine and/or partial least squares analysis (PLS), partition tree analysis, logistic regression analysis (LRA), K-nearest neighbor, neural networks, ensemble learners, voting algorithms, or other algorithmic approach. These analysis techniques take into account the large number of samples required to generate a training set that will enable accurate prediction of outcomes as a result of cut-points established with an in-process training set or cut-points defined for non-algorithmic analysis, but that any number of linear and nonlinear approaches can produce a statistically significant and clinically significant result. As used herein, the term "Kaplan-Meier survival analysis" is understood in the art to be also known as the product limit estimator, which is used to estimate the survival function from lifetime data. In medical research, it is often used to measure the fraction of patients living for a certain amount of time after treatment. IMP GENOMICS®, R, Python libraries including SciPy, SciKit, and numpy software or systems such as TensorFlow provides an interface for utilizing each of the predictive modeling methods disclosed herein, and should not limit the claims to methods performed only with IMP GENOMICS®, R, Python, or TensorFlow software.

In an embodiment, a kit comprising primer pairs suitable for the detection and quantification of nucleic acid expression of 34 genes is disclosed herein, wherein the 34 genes are selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839.

In some embodiments, the primer pairs suitable for the detection and quantification of nucleic acid expression of 34 genes are primer pairs for: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839. In other embodiments, the primer pairs comprise primer pairs for at least one additional gene selected from the genes AIM2, ANXA9, ARPC2, ATP6AP1, BLOC1S1, C1QL4, C21orf59, C3orf70, CCL27, CD163, CHI3L1, CHMP2B, CXCL10, CXCR4, CYP2D6 (LOC101929829), DARS, DCT, DDAH1, DSS1, EGFR, EphB2, FCHSD1, FDFT1, FLG, FN1, HNRNPL, HOXA10 (HOXA9, MIR196B), HPGD, IL24, IL2RB, IL7R, INHBA, IPO5P1, KIT, KLK5, KRT17, KRT18, KRT19, KRT6B, LAMC2, LOR, LRRC47, MIER2, MIR129-1, MIR3916, MKLN1, MMP1, MMP12, MMP13, MMP3, MMP7, MMP9, MRPL21, MYC, NEB, NEFL, NFIA, NFIB, NOA1, PD1, PDL1, PIG3, PIGBOS1, PIM2, PLAU, PTHLH, PTRHD1, RBM33, RPL26L1, S100A8, S100A9, SEPT3, SERPINB2, SERPINB4, SLC25A11, SNORD124, SPATA41, THYN1, TMEM41B, TNNC1, TUBB3, TUFM (MIR4721), TYRP1, UGP2, USP7, VIM, YKT6, and/or ZSCAN31. In other embodiments, the gene set comprises an additional 1, 2, 3, 4, 5, 6, 7, 8, 9, 10, 15, 20, 25, 30, 35, 40, or more than 40 genes selected from the genes listed above.

In another aspect, this disclosure relates to kits to be used in assessing the expression of a gene or set of genes in a cSCC sample or biological sample from a subject to assess the risk of developing recurrence, metastasis, or both. In one embodiment, the disclosure relates to a kit comprising primer pairs suitable for the detection and quantification of nucleic acid expression of 34 genes selected from: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839.

Kits can include any combination of components that facilitates the performance of an assay. A kit that facilitates assessing the expression of the gene or genes may include suitable nucleic acid-based and/or immunological reagents as well as suitable buffers, control reagents, and printed protocols. A "kit" is any article of manufacture (e.g., a package or container) comprising at least one reagent, e.g., a probe or primer set, for specifically detecting a marker or set of markers used in the methods disclosed herein. The article of manufacture may be promoted, distributed, sold, or offered for sale as a unit for performing the methods disclosed herein. The reagents included in such a kit comprise probes, primers, or antibodies for use in detecting one or more of the genes and/or gene sets disclosed herein and demonstrated to be useful for predicting recurrence, metastasis, or both, in patients with cSCC. Kits that facilitate nucleic acid based methods may further include one or more of the following: specific nucleic acids such as oligonucleotides, labeling reagents, enzymes including PCR amplification reagents such as Taq or Pfu, reverse transcriptase, or other, and/or reagents that facilitate hybridization. In addition, the kits disclosed herein may preferably contain instructions which describe a suitable detection assay. Such kits can be conveniently used, e.g., in clinical settings, to diagnose and evaluate patients exhibiting symptoms of cancer, in particular patients exhibiting the possible presence of a cutaneous squamous cell carcinoma.

EXAMPLES

The Examples that follow are illustrative of specific embodiments of the claimed invention, and various uses thereof. They are set forth for explanatory purposes only, and should not be construed as limiting the scope of the claimed invention in any way.

Example 1: cSSC Tumor Sample Preparation and Expression Analysis a. cSCC Tumor Sample Preparation and RNA Isolation Formalin-fixed paraffin embedded (FFPE) primary squamous cell carcinoma tumor specimens arranged in 5 µm sections on microscope slides were acquired from multiple institutions under Institutional Review Board (IRB) approved protocols. All tissue was reviewed by a pathologist. Tissue was marked and tumor tissue was dissected from the slide using a sterile disposable scalpel, collected into a microcentrifuge tube, and deparaffinized using xylene. RNA was isolated from each specimen using the QIAGEN QIAsymphony RNA kit (Hilden, Germany) on the QIAGEN QIAsymphony SP sample preparation automated extractor. RNA quantity was assessed using the NanoDrop™ 8000 system.

b. cDNA Generation and RT-PCR Analysis

RNA isolated from FFPE samples was converted to cDNA using the Applied Biosystems High Capacity cDNA Reverse Transcription Kit (Life Technologies Corporation, Grand Island, NY). Prior to performing the RT-PCR assay, each cDNA sample underwent a 14-cycle pre-amplification step. Pre-amplified cDNA samples were diluted 20-fold in TE buffer. 7.5 µL of each diluted sample was mixed with 7.5 µL of TaqMan OpenArray Real-Time Mastermix, and the solution was loaded to a custom high throughput microfluidics OpenArray card containing primers specific for the genes. Each sample was run in triplicate. The gene expression profile test was performed on a ThermoFisher QuantStudio12k Flex Real-Time PCR system (Life Technologies Corporation, Grand Island, NY).

prognostication, cases with annotated clinical data and sufficient follow-up were used as a development set. Pre-specified bins of patients within the recurrent and non-recurrent group were created, including immunocompromised, immunocompetent, those with a certain number of high risk features and low risk cases. The goal was to satisfy the pre-specified number of cases in each bin for development. Predictive modeling was performed on gene expression data from the development cohort. The predictive model was then validated. 221 cases were included in the development set (see Table 1). Table 1 shows the demographics for the cohort of 221 cases used in this study. They are also stratified by non-recurrence or recurrence. Recurrence is defined as any recurrence—local nodal (satellitosis through regional nodes and distant metastasis). Note that cases with R1 or R2 and local recurrence in the scar or contiguous to the scar were embargoed from this analysis. Characteristics that are associated with higher risk tumors (such as male sex, compromised immune system, head and neck primary tumor, poor differentiation or undifferentiated, higher Clark Level, perineural invasion, and invasion into subcutaneous fat) are features included. This is after embargoing cases that have not yet had data monitoring and did not meet very stringent gene expression data requirements.

TABLE 1

Demographics for the cohort of 221 cases used in Examples 2 and 3

| Feature | All (n = 221) | Non-Recurrence (n = 196) | With Recurrence (n = 25) | p-value |
|---|---|---|---|---|
| Age: Median years (range) | 74 (43-97) | 74 (45-97) | 69 (43-91) | n.s. |
| Mean +/− SD | 72.8 +/− 11.2 | 73.3 +/− 10.8 | 68.6 +/− 13.2 | |
| Definitive surgery: Mohs | 181 (82%) | 161 (82%) | 20 (80%) | n.s. |
| WLE | 39 (18%) | 34 (17%) | 5 (20%) | |
| Male sex | 164 (74%) | 143 (73%) | 21 (84%) | n.s. |
| Patient immunocompromised | 30 (14%) | 20 (10%) | 10 (40%) | p < 0.001 |
| Located on head or neck | 146 (66%) | 129 (66%) | 17 (68%) | n.s. |
| Tumor diameter: | | | | |
| Median cm (range) | 1.4 (0-28) | 1.15 (0-8.8) | 2.9 (0.25-28) | p < 0.001 |
| Mean +/− SD | 1.88 +/− 2.34 | 1.62 +/− 1.47 | 3.89 +/− 5.27 | |
| Differentiation Status: | | | | |
| Poor/Undifferentiated | 12 (5%) | 9 (5%) | 3 (12%) | p < 0.001 |
| Clark Level IV/V | 73 (33%) | 67 (34%) | 6 (24%) | p < 0.001 |
| Perineural invasion present | 12 (5%) | 9 (5%) | 3 (12%) | p < 0.001 |
| Invasion into subcutaneous fat | 22 (10%) | 19 (10%) | 3 (12%) | P = 0.015 | c. Expression Analysis and Class Assignment

Mean $C_t$ values were calculated for triplicate sample sets, and $\Delta C_t$ values were calculated by subtracting the mean $C_t$ of each discriminating gene from the geometric mean of the mean $C_t$ values of all endogenous control genes. $\Delta C_t$ values were standardized according to the mean of the expression of all discriminant genes with a scale equivalent to the standard deviation. Various predictive modeling methods, including radial basis machine, k-nearest neighbor, partition tree, logistic regression, discriminant analysis and distance scoring, and neural network analysis were performed using R version 3.3.2.

Example 2: cSCC Metastatic Risk Genetic Signature and Biomarker Expression

Figure 2:
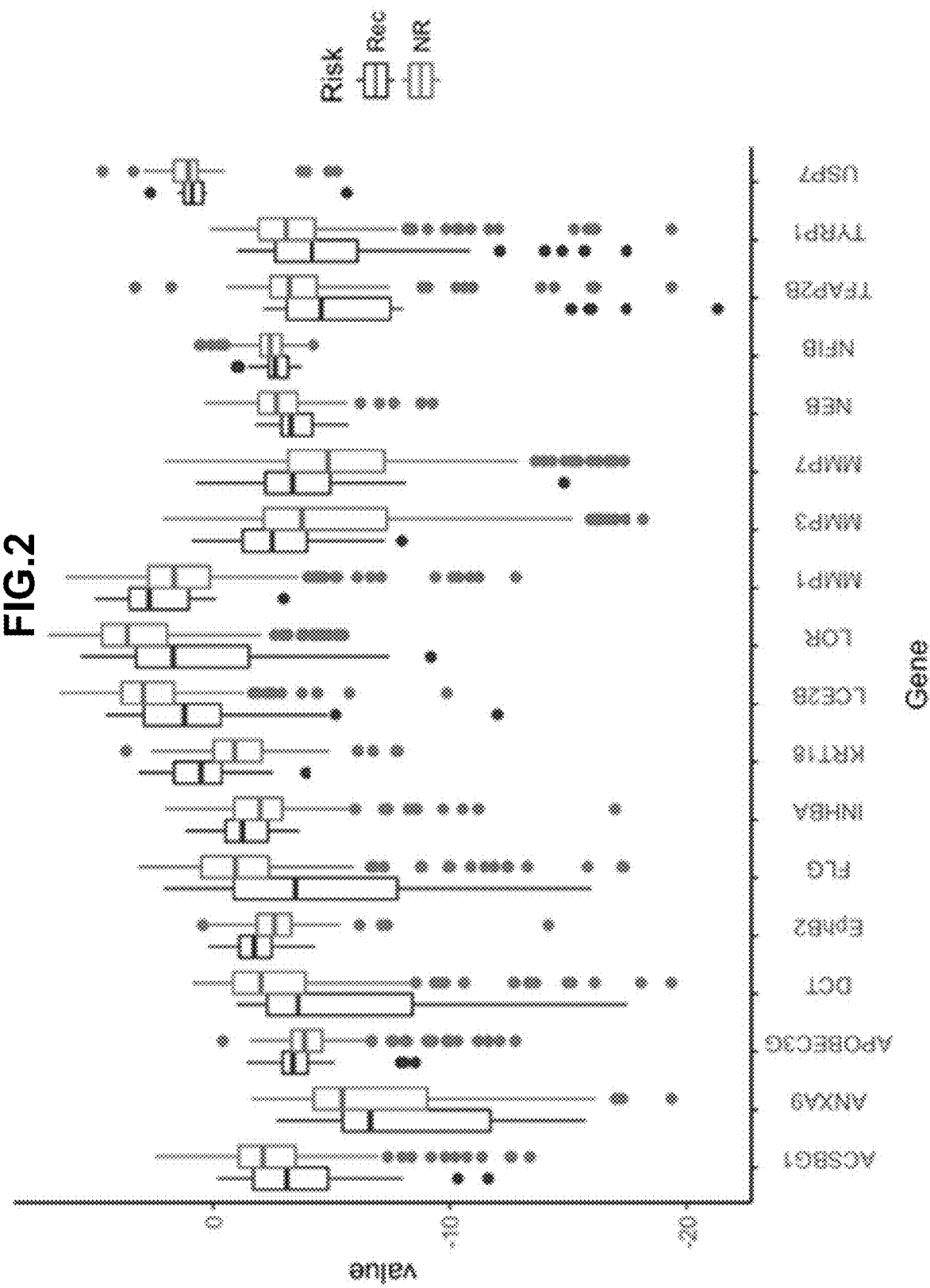
FIG. 2 shows the differential expression of 18 genes found to be significantly differentially expressed between recurrent (Rec) and non-recurrent (NR) cSCC cases
Figure 3:
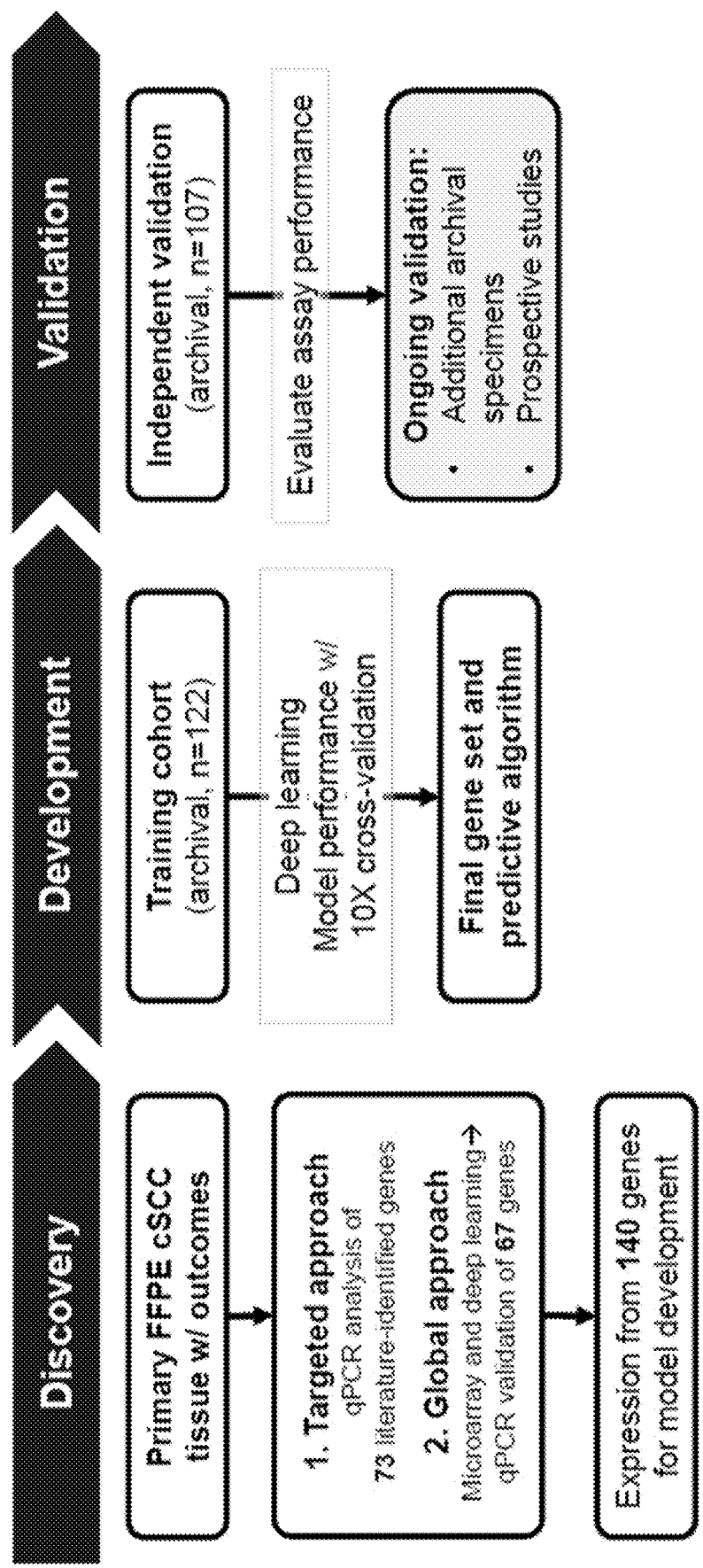
FIG. 3 shows another exemplary study design workflow.

The study design workflow is shown in FIG. 1. First, in order to develop the gene expression profile for cSCC Gene expression differences (RT-PCR data from 73 genes) between recurrent and non-recurrent cSCC cases were evaluated. Using the gene expression data, several control genes were identified that had stable expression across all of the samples. These control genes were then used to normalize the expression of the remaining genes. Gene expression differences between recurrent and non-recurrent cases were investigated to find the genes that are significant. Significant gene expression differences that were associated with local recurrences, regional metastases, and distant metastases were also evaluated. Table 2 below shows genes associated with regional/distant metastases. Genetic expression of the discriminant genes in the signature (Table 2) was assessed in a cohort of 240 cSCC samples using RT-PCR, 18 of these were independently significant to a p-value of p<0.05 (see FIG. 2). As shown in Table 3 below, of the 63 discriminating genes, 18 were altered in metastatic cSCC tumors compared to nonmetastatic tumors with a p-value of p<0.05.

TABLE 2

63 candidate genes for the GEP signature to predict metastatic risk and/recurrence in cSCC tumors

| Gene symbol | p-value | mean-Recurrence | mean-Non-Recurrence |
|---|---|---|---|
| LOR | 0.000 | 0.310 | 2.935 |
| KRT18 | 0.000 | 0.454 | -1.081 |
| LCE2B | 0.000 | 0.447 | 2.490 |
| EphB2 | 0.001 | -1.846 | -2.648 |
| FLG | 0.001 | -4.104 | -1.594 |
| DCT | 0.001 | -5.696 | -3.003 |
| TFAP2B | 0.001 | -6.571 | -3.836 |
| NEB | 0.002 | -3.495 | -2.807 |
| TYRP1 | 0.006 | -5.869 | -3.709 |
| MMP3 | 0.006 | -2.887 | -5.159 |
| MMP7 | 0.010 | -3.915 | -5.568 |
| MMP1 | 0.014 | 2.290 | 0.970 |
| INHBA | 0.016 | -1.203 | -2.222 |
| ACSBG1 | 0.024 | -3.613 | -2.489 |
| USP7 | 0.029 | 0.689 | 1.076 |
| APOBEC3G | 0.035 | -3.800 | -4.260 |
| NFIB | 0.036 | -2.623 | -2.385 |
| ANXA9 | 0.050 | -8.007 | -7.059 |
| RCHY1 | 0.055 | -2.418 | -2.665 |
| PDPN | 0.056 | 1.672 | 1.251 |
| ALOX12 | 0.066 | -4.112 | -3.688 |
| YKT6 | 0.070 | 1.449 | 1.140 |
| PLAU | 0.091 | 1.873 | 1.913 |
| ID2 | 0.110 | -0.921 | -0.550 |
| MMP10 | 0.119 | -0.067 | -1.164 |
| HPGD | 0.141 | -6.830 | -5.781 |
| FN1 | 0.147 | 1.594 | 1.186 |
| HNRNPL | 0.156 | -0.036 | 0.085 |
| AIM2 | 0.159 | -4.093 | -4.610 |
| MMP13 | 0.178 | -7.096 | -8.365 |
| BBC | 0.179 | -7.464 | -7.738 |
| EGFR | 0.189 | 0.908 | 0.705 |
| SPP1 | 0.200 | -0.144 | -1.332 |
| SERPINB4 | 0.251 | -11.815 | -10.852 |
| NEFL | 0.292 | -2.876 | -1.321 |
| NFASC | 0.301 | -3.832 | -3.738 |
| PI3 | 0.324 | 4.686 | 4.847 |
| PIG3 | 0.333 | -3.420 | -3.698 |
| LAMC2 | 0.350 | 0.480 | 0.196 |
| ARPC2 | 0.353 | -0.053 | -0.006 |
| AADAC | 0.379 | -16.094 | -15.629 |
| IL24 | 0.387 | -3.969 | -4.629 |
| S100A8 | 0.388 | 3.838 | 3.936 |
| CCL27 | 0.398 | -12.922 | -13.230 |
| PTHLH | 0.401 | 0.777 | 0.907 |
| S100A9 | 0.457 | 7.525 | 7.534 |
| DDAH1 | 0.461 | -5.660 | -5.216 |
| PDL1 | 0.471 | -3.067 | -3.124 |
| DSS1 | 0.477 | -5.722 | -5.442 |
| KRT19 | 0.486 | -2.982 | -3.853 |
| KIT | 0.529 | -2.391 | -2.415 |
| TUBB3 | 0.599 | -4.541 | -5.167 |
| MYC | 0.631 | -3.816 | -3.749 |
| CHI3L1 | 0.653 | -0.029 | 0.025 |
| MMP9 | 0.684 | 1.649 | 1.733 |
| CXCR4 | 0.742 | -8.733 | -8.858 |
| ATP6V0E2 | 0.750 | -8.562 | -8.519 |
| CXCL10 | 0.785 | -3.039 | -3.184 |
| PD1 | 0.825 | -1.878 | -1.870 |
| IL7R | 0.872 | -8.524 | -8.094 |
| MMP12 | 0.919 | -2.958 | -3.225 |
| CEP76 | 0.981 | -4.361 | -4.656 |

TABLE 3

18 Genes included in a GEP signature able to predict recurrence in cSCC

| Gene symbol | p-value | mean-Recurrence | mean-Non-Recurrence |
|---|---|---|---|
| ACSBG1 | 0.024 | -3.613 | -2.489 |
| ANXA9 | 0.050 | -8.007 | -7.059 |
| APOBEC3G | 0.035 | -3.800 | -4.260 |
| DCT | 0.001 | -5.696 | -3.003 |
| EphB2 | 0.001 | -1.846 | -2.648 |
| FLG | 0.001 | -4.104 | -1.594 |
| INHBA | 0.016 | -1.203 | -2.222 |
| KRT18 | 0.000 | 0.454 | -1.081 |
| LCE2B | 0.000 | 0.447 | 2.490 |
| LOR | 0.000 | 0.310 | 2.935 |
| MMP1 | 0.014 | 2.290 | 0.970 |
| MMP3 | 0.006 | -2.887 | -5.159 |
| MMP7 | 0.010 | -3.915 | -5.568 |
| NEB | 0.002 | -3.495 | -2.807 |
| NFIB | 0.036 | -2.623 | -2.385 |
| TFAP2B | 0.001 | -6.571 | -3.836 |
| TYRP1 | 0.006 | -5.869 | -3.709 |
| USP7 | 0.029 | 0.689 | 1.076 |

Example 3: Initial Training Set Development Studies and Comparison to Validation Cohort R version 3.3.2 was used to train multiple predictive models (e.g., multiple machine-learning methods such as, neural networks, gradient boosting machine, generalized linear model boost, radial basis function, rule-based classification, decision tree classification, and/or regularized linear discriminant analysis) against the normalized Ct values obtained from RT-PCR analysis in 181 cSCC cases selected at random from the 240 cases in the combined set. The average of the top predictive models was more sensitive than either the Brigham and Women's Hospital (BWH) or American Joint Committee on Cancer (AJCC) models with minimal loss of specificity. These results show that recurrent and non-recurrent cSCC can be identified through gene expression profiling and gene expression can be used to identify cSCC patients with a higher risk of recurrence. A validated prognostic test could inform clinical decision-making on preoperative surgical staging (for example, based on shave biopsy), surgical approach (SLNB) or adjuvant radiation to reduce local recurrence, and adjuvant radiation, nodal staging, adjuvant systemic therapy to reduce regional/distant metastasis. Such a test could improve such intervention decisions and help determine which patients may benefit from additional therapeutic modalities.

TABLE 4

Predictive modeling-local recurrence

| Local Recurrence | GEP Example 2 | BWH | AJCCv7 | AJCCv8 |
|---|---|---|---|---|
| Sensitivity | 75% | 17% | 0% | 39% |
| Specificity | 92% | 90% | 99.5% | 79% |
| negative predictive value (NPV) | 98% | 92% | 92% | 94% |
| positive predictive value (PPV) | 50% | 13% | 94% | 14% |

TABLE 5

Predictive modeling-metastasis

| Regional/Distant Metastasis | GEP Example 2 | BWH | AJCCv7 | AJCCv8 |
|---|---|---|---|---|
| Sensitivity | 83% | 23% | 0% | 46% |
| Specificity | 95% | 90% | 100% | 79% |
| negative predictive value (NPV) | 99% | 95% | 94% | 96% |
| positive predictive value (PPV) | 53% | 13% | 0% | 12% |

Figure 4:
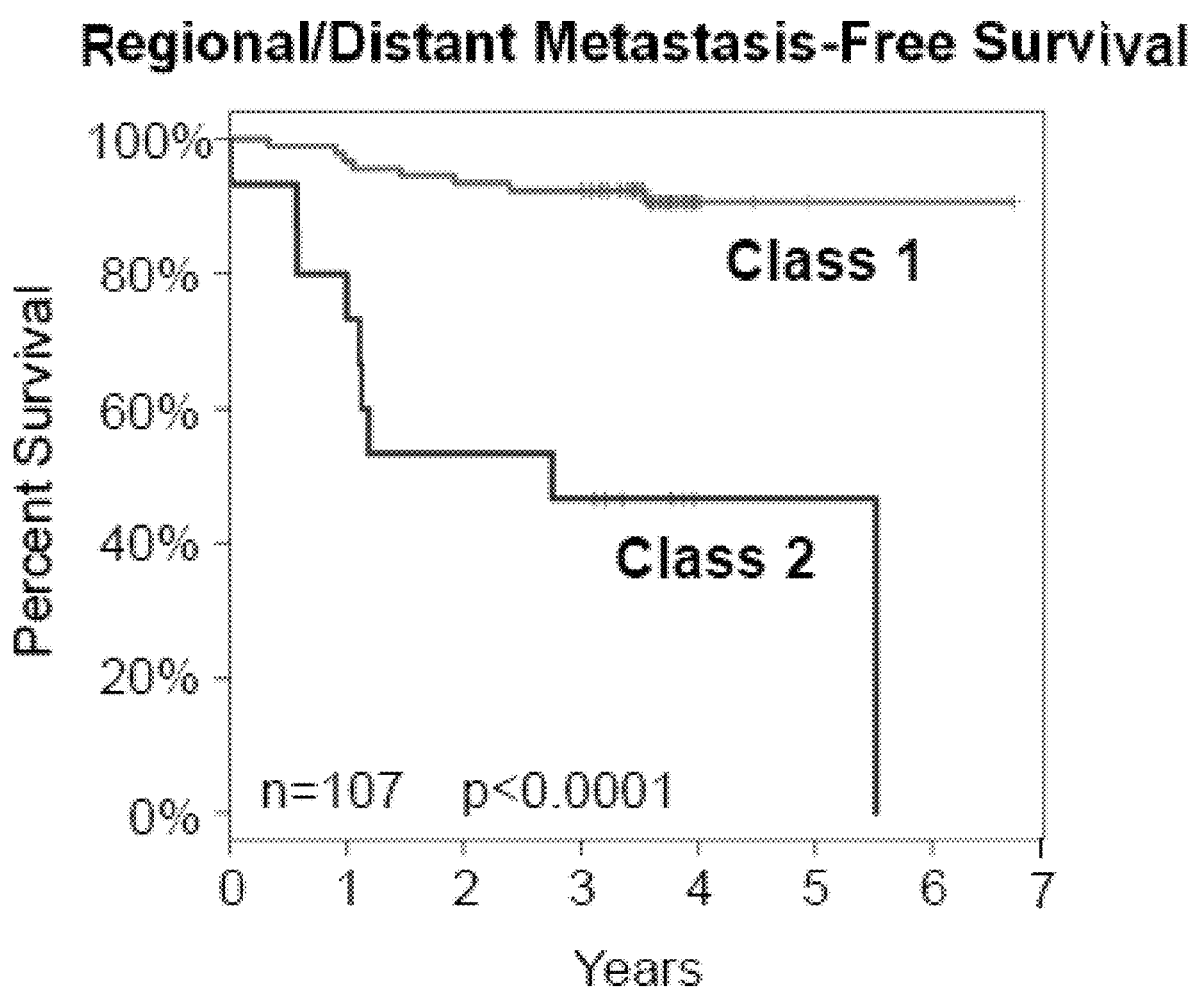
FIG. 4 shows a metastasis-free survival curve (regional and distant metastasis) for low risk, Class 1, and high-risk, Class 2, tumors using the 20-1 gene set.

Example 4: Prognostic Gene Expression Profile Test in cSCC in Patients with One or More High-Risk Features To identify a gene expression profile that accurately predicts: (1) primary cSCC with a high risk of regional nodal/distant metastasis; and (2) primary cSCC with high risk of local recurrence after complete surgical clearance, a multi-center study was performed using archived primary tissue samples with extensive capture of associated clinical data. The approach uses targeted candidate genes from the literature combined with genes from a global approach microarray screen. Samples are from subjects with pathologically confirmed cSCC diagnosed after 2006, minimum 3 years of follow-up or event (see Tables 6 and 7). Two separate outcomes were measured: (1) nodal/distant metastasis; and (2) local recurrence. Accuracy metrics demonstrate that the gene expression signature has prognostic value for in an independent cohort (see Table 8 and FIG. 4). The prognostic test could inform clinical decision-making on: (1) preoperative surgical staging, based on shave biopsy; and (2) adjuvant radiation, nodal staging, adjuvant systemic therapy to reduce regional/distant metastasis.

TABLE 6

Demographics for development stage of Example 4.

| Feature | All (n = 122) | Non-Metastatic (n = 108) | Regional/distant metastasis (n = 14) |
|---|---|---|---|
| Age: Median years (range) | 74 (49-97) | 74 (50-97) | 74.5 (49-91) |
| Definitive surgery: Mohs | 99 (82%)[#] | 88 (82%)[#] | 11 (79%) |
| Male sex | 94 (77%) | 81 (75%) | 13 (93%) |
| Patient immunocompromised | 17 (14%) | 13 (12%) | 4 (29%) |
| Located on head or neck | 87 (71%) | 77 (71%) | 10 (71%) |
| Tumor diameter: Mean +/− SD | 2.0 +/− 2.9 | 1.5 +/− 1.3 | 5.8 +/− 6.7*** |
| Differentiation Status: | | | |
| Poorly differentiated | 5 (4%) | 4 (4%) | 1 (7%) |
| Clark Level IV/V | 45 (37%) | 40 (37%) | 5 (36%) |
| Perineural invasion present | 7 (6%) | 6 (6%) | 1 (7%) |
| Invasion into subcutaneous fat | 7 (6%) | 4 (4%) | 3 (21%)** |

[#]1 case with unknown surgery type;
Wilcoxon F or Chi-square test p < 0.01 *< 0.001

TABLE 7

Demographics for validation stage of Example 4.

| Feature | All (n = 107) | Non-Met (n = 90) | Regional/ distant met (n = 17) |
|---|---|---|---|
| Age: Median years (range) | 72 (30-93) | 72.5 (45-93) | 72 (30-88) |
| Definitive surgery: Mohs | 86 (81%)[#] | 76 (84%) | 10 (63%)[#]* |
| Male sex | 78 (73%) | 64 (71%) | 14 (82%) |
| Patient immunocompromised | 12 (11%) | 10 (11%) | 2 (12%) |
| Located on head or neck | 76 (71%) | 62 (69%) | 14 (82%) |
| Tumor diameter: Mean +/− SD | 1.9 +/− 1.7 | 1.9 +/− 1.2 | 3.3 +/− 2.6** |
| Differentiation Status: | | | |
| Poorly differentiated | 13 (12%) | 6 (7%) | 7 (42%)*** |
| Clark Level IV/V | 32 (30%) | 25 (28%) | 7 (41%) |
| Perineural invasion present | 9 (8%) | 3 (3%) | 6 (35%)*** |
| Invasion into subcutaneous fat | 17 (16%) | 11 (12%) | 6 (35%)* |

[#]1 case with unknown surgery type;
Wilcoxon F or Chi-square test p *< 0.05 < 0.01 *< 0.001

TABLE 8

Predictive modeling

| Metric | GEP Example 4 | AJCC 8 | BWH |
|---|---|---|---|
| Sensitivity | 53% | 53% | 41% |
| Specificity | 93% | 87% | 88% |
| negative predictive value (NPV) | 91% | 91% | 89% |
| positive predictive value (PPV) | 60% | 43% | 39% |

Example 5: Prognostic Gene Expression Signature for Risk Assessment in cSCC with a Subanalysis in the Head and Neck Region To identify a gene expression profile that accurately predicts: (1) primary cSCC with a high risk of metastasis (regional nodal/distant metastasis); and (2) primary cSCC with high risk of local recurrence after complete surgical clearance, a multi-center study was performed using archived primary tissue samples with extensive capture of associated clinical data. The approach uses targeted candidate genes from the literature combined with genes from a global approach microarray screen. Samples are from subjects with pathologically confirmed cSCC diagnosed after 2006, minimum 3 years of follow-up or event (see Table 9). Two separate outcomes were measured: (1) nodal/distant metastasis; and (2) local recurrence. Accuracy metrics accuracy metrics for all and head and neck cSCC cases suggest that gene expression signature has prognostic value in an independent cohort (see Table 10). The prognostic signature with a robust PPV for high-risk disease will improve identification of patients with cSCC who can benefit from surgical, radiation and immunotherapy interventions.

TABLE 9

Demographics-head and neck subanalysis

| Feature of head and neck case | Non-Metastatic (n = 34) | Metastasis (n = 9) |
|---|---|---|
| Age: Median years (range) | 75 (49-89) | 77 (49-89) |
| Definitive surgery: Mohs | 33 (97%) | 8 (89%) |
| Male sex | 31 (91%) | 8 (89%) |
| Tumor diameter: Mean cm +/− SD | 2.52 +/− 1.35 | 5.89 +/− 8.36 |
| Differentiation Status: | | |
| Poor/Undifferentiated | 2 (6%) | 2 (22%) |
| Clark Level IV/V | 4 (12%) | 1 (11%) |
| Perineural invasion present | 4 (12%) | 0 (0%) |
| Invasion into subcutaneous fat | 7 (21%) | 1 (11%) |

TABLE 10

Predictive modeling-head and neck subanalysis

| | All (n = 107) | | H&N (n = 76) | |
|---|---|---|---|---|
| Metric | GEP Example 5 | BWH | GEP this study | BWH |
| Sensitivity | 53% | 41% | 43% | 43% |
| Specificity | 93% | 88% | 94% | 89% |
| negative predictive value (NPV) | 91% | 89% | 88% | 87% |
| positive predictive value (PPV) | 60% | 39% | 60% | 46% |

TABLE 11

Genes included in the gene sets that are able to predict risk of recurrence and/or metastasis

| Gene name | Probe Identifier (ThermoFisher) | median Recurrent | median Non-Recurrent | delta median * | p-value |
|---|---|---|---|---|---|
| KRT6B | Hs00745492_s1 | 5.522 | 7.091 | −1.569 | 0.000070 |
| LOR | Hs01894962_s1 | 1.970 | 4.492 | −2.522 | 0.000265 |
| FLG | Hs00856927_g1 | −2.724 | 0.303 | −3.027 | 0.000291 |
| LCE2B | Hs04194422_s1 | 1.153 | 3.665 | −2.512 | 0.000809 |
| PLS3 | Hs00543973_m1 | −0.416 | 0.080 | −0.497 | 0.001048 |
| SERPINB2 | Hs01010736_m1 | 0.304 | 1.455 | −1.150 | 0.001277 |
| KLK5 | Hs00202752_m1 | 1.170 | 3.239 | −2.069 | 0.001468 |
| KRT18 | Hs01920599_gH | 0.975 | −0.238 | 1.213 | 0.002094 |
| BBC | Hs00248075_m1 | −4.614 | −5.334 | 0.720 | 0.002663 |
| MIR3916 | Hs04232205_s1 | −0.709 | −1.334 | 0.625 | 0.002734 |
| LOC100287896 | Hs01931732_s1 | −2.224 | −2.796 | 0.572 | 0.003547 |
| TFAP2B | Hs01560931_m1 | −4.288 | −2.456 | −1.832 | 0.004135 |
| HPGD | Hs00960591_m1 | −5.491 | −3.113 | −2.378 | 0.007656 |
| CHMP2B | Hs00387770_m1 | −3.117 | −2.591 | −0.526 | 0.008827 |
| ANXA9 | Hs01070154_m1 | −5.583 | −4.284 | −1.299 | 0.009038 |
| ID2 | Hs00747379_m1 | −0.345 | 0.493 | −0.838 | 0.009695 |
| EphB2 | Hs00362096_m1 | −1.124 | −1.614 | 0.491 | 0.012203 |
| NEB | Hs00189880_m1 | −2.611 | −1.904 | −0.706 | 0.014937 |
| FDFT1 | Hs00926053_m1 | −1.589 | −0.657 | −0.932 | 0.017046 |
| USP7 | Hs00931763_m1 | 1.509 | 1.960 | −0.452 | 0.017046 |
| TAF6L | Hs01008033_m1 | −0.699 | −0.961 | 0.262 | 0.018195 |
| ACSBG1 | Hs01025572_m1 | −2.992 | −1.336 | −1.657 | 0.026077 |
| HNRNPL | Hs00704853_s1 | 0.776 | 0.980 | −0.204 | 0.031337 |
| ARPC2 | Hs01031740_m1 | 0.715 | 1.147 | −0.432 | 0.031337 |
| DUXAP8 | Hs04942686_m1 | −6.816 | −9.507 | 2.691 | 0.039746 |
| PIM2 | Hs01546752_g1 | −1.160 | −1.752 | 0.592 | 0.050944 |
| KRT17 | Hs00356958_m1 | 6.944 | 7.254 | −0.310 | 0.053874 |
| APOBEC3G | Hs00222415_m1 | −2.574 | −3.024 | 0.450 | 0.056942 |
| DSS1 | Hs00428732_m1 | −4.131 | −3.182 | −0.949 | 0.056942 |
| EGFR | Hs01076090_m1 | 1.598 | 1.332 | 0.266 | 0.069464 |
| SERPINB4 | Hs01691258_g1 | −12.838 | −8.116 | −4.722 | 0.070706 |
| UGP2 | Hs00900510_m1 | −1.783 | −1.437 | −0.346 | 0.073246 |
| SPATA41 | Hs03028557_s1 | −12.073 | −13.333 | 1.261 | 0.077195 |
| SNORD124 | Hs03464469_s1 | −2.848 | −2.958 | 0.110 | 0.082729 |
| PI3 | Hs00964384_g1 | 5.550 | 6.140 | −0.589 | 0.085614 |
| LIME1-ZGPAT | Hs00738791_g1 | −4.044 | −4.312 | 0.267 | 0.090094 |
| MMP3 | Hs00968305_m1 | −1.478 | −2.397 | 0.919 | 0.099619 |
| S100A8 | Hs00374264_g1 | 4.237 | 5.014 | −0.777 | 0.104673 |
| PTRHD1 | Hs00415546_m1 | −1.338 | −1.216 | −0.122 | 0.109930 |
| MMP7 | Hs01042796_m1 | −2.399 | −3.937 | 1.538 | 0.115392 |
| TMEM41B | Hs01379134_m1 | −1.979 | −1.562 | −0.417 | 0.119151 |
| SPP1 | Hs00959010_m1 | 1.650 | 0.427 | 1.224 | 0.121066 |
| RBM33 | Hs00997579_m1 | 1.600 | 1.349 | 0.251 | 0.152768 |
| NFIB | Hs01029174_m1 | −1.757 | −1.633 | −0.124 | 0.159806 |
| NEFL | Hs00196245_m1 | −0.069 | 0.561 | −0.631 | 0.162206 |
| NFIC | Hs00232157_m1 | −0.500 | −0.300 | −0.200 | 0.167086 |
| DCT | Hs01098278_m1 | −3.033 | −1.300 | −1.733 | 0.174613 |
| RCHY1 | Hs00996236_m1 | −1.807 | −2.038 | 0.231 | 0.177178 |
| ZSCAN31 | Hs00372831_g1 | −3.639 | −2.926 | −0.713 | 0.179770 |
| IPO5P1 | Hs05052601_s1 | −2.927 | −3.231 | 0.303 | 0.179770 |
| RUNX3 | Hs00231709_m1 | −0.927 | −1.342 | 0.415 | 0.204381 |

TABLE 11-continued

Genes included in the gene sets that are able to predict risk of recurrence and/or metastasis

| Gene name | Probe Identifier (ThermoFisher) | median Recurrent | median Non-Recurrent | delta median * | p-value |
|---|---|---|---|---|---|
| MKLN1 | Hs00992679_m1 | −0.787 | −0.930 | 0.144 | 0.204381 |
| ATP6V0E2 | Hs04189864_m1 | −5.596 | −6.247 | 0.651 | 0.207260 |
| YKT6 | Hs00559914_m1 | 2.007 | 1.788 | 0.220 | 0.210168 |
| FCHSD1 | Hs00703025_s1 | −6.048 | −5.195 | −0.854 | 0.216073 |
| MMP1 | Hs00899658_m1 | 3.156 | 2.381 | 0.774 | 0.225153 |
| CEP76 | Hs00950371_m1 | −3.743 | −3.455 | −0.288 | 0.225153 |
| TUFM-MIR4721 | Hs00944507_g1 | 2.465 | 2.281 | 0.184 | 0.228239 |
| AIM2 | Hs00915710_m1 | −2.525 | −2.720 | 0.195 | 0.244123 |
| PTHLH | Hs00174969_m1 | 0.986 | 1.833 | −0.848 | 0.264188 |
| BHLHB9 | Hs01089557_s1 | −14.090 | −12.657 | −1.433 | 0.264188 |
| CD163 | Hs00174705_m1 | −0.829 | −1.156 | 0.327 | 0.307655 |
| ZNF839 | Hs00901350_g1 | −1.060 | −1.316 | 0.256 | 0.307655 |
| BLOC1S1 | Hs00155241_m1 | −1.061 | −0.787 | −0.273 | 0.311480 |
| HDDC3 | Hs00826827_g1 | −1.299 | −1.567 | 0.267 | 0.319223 |
| TNNC1 | Hs00896999_g1 | −7.015 | −5.911 | −1.105 | 0.323141 |
| S100A9 | Hs00610058_m1 | 8.071 | 8.385 | −0.314 | 0.327091 |
| TUBB3 | Hs00801390_m1 | −3.190 | −2.711 | −0.479 | 0.331071 |
| KIT | Hs00174029_m1 | −1.168 | −1.574 | 0.406 | 0.351443 |
| FN1 | Hs01549976_m1 | 2.302 | 1.859 | 0.443 | 0.364039 |
| INHBA | Hs01081598_m1 | −1.107 | −1.166 | 0.060 | 0.368299 |
| PIGBOS1 | Hs05036222_s1 | −0.970 | −1.132 | 0.162 | 0.372591 |
| THYN1 | Hs01553775_g1 | 0.011 | −0.219 | 0.230 | 0.376913 |
| HOXA10-HOXA9-MIR196B | Hs00365956_m1 | −3.574 | −2.521 | −1.053 | 0.412594 |
| MYC | Hs00153408_m1 | −2.553 | −2.337 | −0.215 | 0.440624 |
| IL24 | Hs01114274_m1 | −3.039 | −3.394 | 0.355 | 0.455038 |
| NFIA | Hs00379134_m1 | −0.852 | −0.709 | −0.143 | 0.499836 |
| RPL26L1 | Hs01631495_s1 | −6.405 | −6.603 | 0.198 | 0.504954 |
| ZNF48 | Hs00399035_m1 | −3.340 | −3.577 | 0.237 | 0.520473 |
| MIER2 | Hs00380101_m1 | −0.275 | −0.382 | 0.108 | 0.530953 |
| MMP13 | Hs00942584_m1 | −4.547 | −5.058 | 0.511 | 0.536233 |
| TYRP1 | Hs00167051_m1 | −2.547 | −2.510 | −0.037 | 0.546872 |
| VIM | Hs00958111_m1 | 4.763 | 4.373 | 0.390 | 0.552231 |
| LRRC47 | Hs00975850_m1 | 0.130 | 0.070 | 0.060 | 0.552231 |
| ALOX12 | Hs00167524_m1 | −3.032 | −2.563 | −0.469 | 0.590445 |
| PLAU | Hs01547054_m1 | 3.212 | 2.870 | 0.342 | 0.612814 |
| IL7R | Hs00902334_m1 | −4.480 | −4.820 | 0.340 | 0.624137 |
| DARS | Hs00962398_m1 | 2.314 | 2.486 | −0.172 | 0.624137 |
| LOC101927502 | Hs05033260_s1 | −8.529 | −8.227 | −0.302 | 0.624137 |
| MIR129-1 | Hs03302824_pri | −12.122 | −13.033 | 0.910 | 0.647050 |
| PD1 | Hs00240906_m1 | −1.233 | −1.099 | −0.134 | 0.652832 |
| CYP2D6-LOC101929829 | Hs03043789_g1 | −5.343 | −5.128 | −0.215 | 0.676166 |
| GTPBP2 | Hs01051445_g1 | −2.289 | −2.127 | −0.163 | 0.687952 |
| CXCL10 | Hs00171042_m1 | −1.850 | −1.595 | −0.255 | 0.693874 |
| SLC1A3 | Hs00904817_m1 | −2.518 | −2.534 | 0.016 | 0.699815 |
| RNF135 | Hs00260480_m1 | −0.694 | −0.725 | 0.030 | 0.711752 |
| NOA1 | Hs00260452_m1 | −2.426 | −2.528 | 0.102 | 0.747977 |
| ZNF496 | Hs00262107_m1 | −1.484 | −1.549 | 0.065 | 0.760181 |
| MMP12 | Hs00159178_m1 | −2.301 | −2.567 | 0.266 | 0.772445 |
| C3orf70 | Hs01395177_m1 | −4.175 | −4.227 | 0.052 | 0.784767 |
| LAMC2 | Hs01043717_m1 | 0.874 | 1.000 | −0.126 | 0.797143 |
| MMP10 | Hs00233987_m1 | −0.255 | 0.441 | −0.696 | 0.803350 |
| C1QL4 | Hs00884853_s1 | −10.397 | −10.511 | 0.113 | 0.822045 |
| C21orf59 | Hs00937509_m1 | 0.903 | 0.829 | 0.074 | 0.822045 |
| KRT19 | Hs01051611_gH | −3.414 | −2.626 | −0.788 | 0.828299 |
| PDL1 | Hs00204257_m1 | −2.051 | −2.218 | 0.166 | 0.847127 |
| SLC25A11 | Hs01087946_g1 | 0.664 | 0.641 | 0.024 | 0.847127 |
| MRC1 | Hs00267207_m1 | −5.005 | −5.020 | 0.015 | 0.853423 |
| PIG3 | Hs00936519_m1 | −3.104 | −2.896 | −0.207 | 0.853423 |
| IL2RB | Hs00386692_m1 | −1.702 | −1.592 | −0.110 | 0.878697 |
| ATP6AP1 | Hs05016463_s1 | 0.173 | 0.183 | −0.011 | 0.878697 |
| MSANTD4 | Hs00411188_g1 | −3.627 | −3.612 | −0.015 | 0.929591 |
| MRPL21 | Hs00698959_m1 | 0.665 | 0.664 | 0.002 | 0.929591 |
| CXCR4 | Hs00607978_s1 | −5.555 | −5.868 | 0.313 | 0.935977 |
| RPP38 | Hs00705626_s1 | −4.839 | −4.719 | −0.120 | 0.935977 |
| SEPT3 | Hs00251883_m1 | −5.165 | −5.094 | −0.071 | 0.942368 |
| PDPN | Hs00366766_m1 | 1.995 | 1.893 | 0.102 | 0.948762 |

TABLE 11-continued

Genes included in the gene sets that are able to predict risk of recurrence and/or metastasis

| Gene name | Probe Identifier (ThermoFisher) | median Recurrent | median Non-Recurrent | delta median * | p-value |
|---|---|---|---|---|---|
| CCL27 | Hs00171157_m1 | −12.962 | −11.407 | −1.555 | 0.967963 |
| CHI3L1 | Hs01072228_m1 | 0.794 | 0.689 | 0.105 | 0.974368 |
| DDAH1 | Hs00201707_m1 | −3.775 | −3.568 | −0.207 | 0.980774 |
| MMP9 | Hs00957562_m1 | 2.233 | 2.368 | −0.135 | 0.987182 |
| NFASC | Hs00978280_m1 | −2.781 | −2.716 | −0.066 | 0.993591 |

*Positive values indicate an INCREASE in gene expression in recurrent cancer when compared to non-recurrent control; and negative values indicate a DECREASE in gene expression in recurrent cancer when compared to non-recurrent control.

TABLE 12

Accuracy of gene sets used to predict risk of recurrence and/or metastasis

| Gene set | Sensitivity | Specificity | PPV | NPV | AUC | Kappa |
|---|---|---|---|---|---|---|
| 20-1 | 0.4958 | 0.9481 | 0.5931 | 0.9370 | 0.8604 | 0.4537 |
| 20-2 | 0.5208 | 0.9333 | 0.5869 | 0.9385 | 0.8101 | 0.4524 |
| 20-3 | 0.4438 | 0.9472 | 0.5829 | 0.9292 | 0.8131 | 0.4147 |
| 20-4 | 0.4708 | 0.9324 | 0.5688 | 0.9318 | 0.8766 | 0.4084 |
| 20-5 | 0.4833 | 0.9324 | 0.4990 | 0.9335 | 0.8242 | 0.4033 |
| 20-6 | 0.4542 | 0.9389 | 0.5722 | 0.9306 | 0.8275 | 0.3991 |
| 20-7 | 0.5396 | 0.9065 | 0.4634 | 0.9395 | 0.8384 | 0.3934 |
| 20-8 | 0.3917 | 0.9537 | 0.5922 | 0.9238 | 0.7275 | 0.3783 |
| 20-9 | 0.4396 | 0.9259 | 0.5132 | 0.9274 | 0.8220 | 0.3673 |
| 20-10 | 0.3708 | 0.9556 | 0.5888 | 0.9228 | 0.7970 | 0.3621 |
| 20-11 | 0.4542 | 0.9241 | 0.4625 | 0.9299 | 0.7701 | 0.3615 |
| 20-12 | 0.4292 | 0.9324 | 0.4984 | 0.9280 | 0.7876 | 0.3613 |
| 20-13 | 0.3896 | 0.9472 | 0.5367 | 0.9234 | 0.8228 | 0.3605 |
| 20-14 | 0.4146 | 0.9343 | 0.5150 | 0.9254 | 0.7698 | 0.3600 |
| 20-15 | 0.4417 | 0.9278 | 0.4798 | 0.9299 | 0.7799 | 0.3553 |
| 20-16 | 0.4271 | 0.9278 | 0.4667 | 0.9262 | 0.7650 | 0.3506 |
| 20-17 | 0.4146 | 0.9287 | 0.4673 | 0.9248 | 0.7613 | 0.3506 |
| 20-18 | 0.4563 | 0.9139 | 0.4518 | 0.9297 | 0.8198 | 0.3491 |
| 20-19 | 0.4188 | 0.9315 | 0.5352 | 0.9270 | 0.8132 | 0.3489 |
| 20-20 | 0.4229 | 0.9296 | 0.4484 | 0.9264 | 0.7674 | 0.3438 |
| 20-21 | 0.4396 | 0.9231 | 0.4449 | 0.9290 | 0.8336 | 0.3420 |
| 20-22 | 0.4354 | 0.9194 | 0.4282 | 0.9268 | 0.8127 | 0.3418 |
| 20-23 | 0.3563 | 0.9537 | 0.5608 | 0.9213 | 0.7605 | 0.3379 |
| 20-24 | 0.3896 | 0.9296 | 0.4846 | 0.9221 | 0.7662 | 0.3357 |
| 20-25 | 0.3896 | 0.9370 | 0.4919 | 0.9218 | 0.8326 | 0.3354 |
| 30-1 | 0.4021 | 0.9648 | 0.6285 | 0.9275 | 0.8091 | 0.3893 |
| 30-2 | 0.4771 | 0.9204 | 0.4672 | 0.9335 | 0.8005 | 0.3739 |
| 30-3 | 0.4438 | 0.9287 | 0.4984 | 0.9287 | 0.8083 | 0.3685 |
| 30-4 | 0.4208 | 0.9306 | 0.5525 | 0.9270 | 0.8064 | 0.3613 |
| 30-5 | 0.4000 | 0.9407 | 0.5432 | 0.9255 | 0.7804 | 0.3513 |
| 30-6 | 0.4542 | 0.9167 | 0.4574 | 0.9288 | 0.7920 | 0.3480 |
| 30-7 | 0.3875 | 0.9407 | 0.5049 | 0.9240 | 0.8209 | 0.3378 |
| 30-8 | 0.3792 | 0.9454 | 0.5218 | 0.9225 | 0.7739 | 0.3375 |
| 30-9 | 0.3542 | 0.9593 | 0.5714 | 0.9207 | 0.6822 | 0.3347 |
| 30-10 | 0.4458 | 0.9157 | 0.4271 | 0.9281 | 0.7544 | 0.3339 |
| 30-11 | 0.4167 | 0.9213 | 0.4288 | 0.9245 | 0.7915 | 0.3329 |
| 30-12 | 0.3813 | 0.9380 | 0.4732 | 0.9216 | 0.7236 | 0.3318 |
| 30-13 | 0.3229 | 0.9565 | 0.6146 | 0.9170 | 0.7093 | 0.3243 |
| 30-14 | 0.3729 | 0.9361 | 0.4768 | 0.9222 | 0.7127 | 0.3187 |
| 30-15 | 0.4042 | 0.9176 | 0.3988 | 0.9225 | 0.7716 | 0.3103 |
| 30-16 | 0.3667 | 0.9306 | 0.4688 | 0.9195 | 0.7127 | 0.3052 |
| 30-17 | 0.3375 | 0.9426 | 0.4744 | 0.9178 | 0.6708 | 0.3025 |
| 30-18 | 0.3813 | 0.9213 | 0.4323 | 0.9205 | 0.8029 | 0.2996 |
| 30-19 | 0.4146 | 0.9102 | 0.3787 | 0.9241 | 0.7652 | 0.2984 |
| 30-20 | 0.3667 | 0.9296 | 0.4427 | 0.9199 | 0.7452 | 0.2954 |
| 30-21 | 0.3583 | 0.9306 | 0.4480 | 0.9197 | 0.7475 | 0.2900 |
| 30-22 | 0.3625 | 0.9241 | 0.4685 | 0.9181 | 0.7671 | 0.2897 |
| 30-23 | 0.3833 | 0.9194 | 0.3956 | 0.9199 | 0.7480 | 0.2891 |
| 30-24 | 0.3417 | 0.9380 | 0.4473 | 0.9187 | 0.7222 | 0.2885 |
| 30-25 | 0.3979 | 0.9120 | 0.3898 | 0.9221 | 0.7419 | 0.2868 |
| 40-1 | 0.4688 | 0.9481 | 0.6105 | 0.9334 | 0.8198 | 0.4340 |
| 40-2 | 0.4021 | 0.9435 | 0.5360 | 0.9242 | 0.7960 | 0.3565 |
| 40-3 | 0.3792 | 0.9426 | 0.5311 | 0.9230 | 0.7486 | 0.3354 |
| 40-4 | 0.3563 | 0.9509 | 0.5030 | 0.9200 | 0.7427 | 0.3325 |
| 40-5 | 0.4125 | 0.9278 | 0.4898 | 0.9257 | 0.8127 | 0.3300 |
| 40-6 | 0.3896 | 0.9361 | 0.4924 | 0.9235 | 0.7824 | 0.3294 |
| 40-7 | 0.3854 | 0.9324 | 0.4662 | 0.9219 | 0.7421 | 0.3248 |
| 40-8 | 0.3646 | 0.9398 | 0.5220 | 0.9212 | 0.7262 | 0.3228 |
| 40-9 | 0.3583 | 0.9380 | 0.5303 | 0.9199 | 0.7621 | 0.3189 |
| 40-10 | 0.3500 | 0.9472 | 0.4906 | 0.9201 | 0.7059 | 0.3161 |
| 40-11 | 0.3938 | 0.9222 | 0.4707 | 0.9225 | 0.7623 | 0.3143 |
| 40-12 | 0.3417 | 0.9500 | 0.5070 | 0.9188 | 0.7769 | 0.3115 |
| 40-13 | 0.3896 | 0.9296 | 0.4195 | 0.9233 | 0.7851 | 0.3047 |
| 40-14 | 0.3479 | 0.9407 | 0.4750 | 0.9178 | 0.8177 | 0.3036 |
| 40-15 | 0.3729 | 0.9269 | 0.4124 | 0.9206 | 0.6769 | 0.3034 |
| 40-16 | 0.3646 | 0.9343 | 0.4224 | 0.9200 | 0.7467 | 0.2989 |
| 40-17 | 0.3792 | 0.9222 | 0.4296 | 0.9204 | 0.7539 | 0.2983 |
| 40-18 | 0.3208 | 0.9435 | 0.5381 | 0.9152 | 0.6774 | 0.2980 |
| 40-19 | 0.3688 | 0.9194 | 0.4660 | 0.9192 | 0.6873 | 0.2940 |
| 40-20 | 0.3854 | 0.9204 | 0.4162 | 0.9224 | 0.8275 | 0.2939 |
| 40-21 | 0.3833 | 0.9167 | 0.3896 | 0.9215 | 0.7007 | 0.2904 |
| 40-22 | 0.3625 | 0.9185 | 0.4270 | 0.9177 | 0.6769 | 0.2904 |
| 40-23 | 0.3313 | 0.9343 | 0.4227 | 0.9160 | 0.6716 | 0.2836 |
| 40-24 | 0.3438 | 0.9407 | 0.4236 | 0.9193 | 0.6736 | 0.2799 |
| 40-25 | 0.3250 | 0.9389 | 0.4582 | 0.9160 | 0.6687 | 0.2774 |

TABLE 13

Exemplary gene sets used to predict risk of recurrence and/or metastasis

| Gene set | Probe identifiers used for each gene set (probe identifiers from ThermoFisher Scientific). |
|---|---|
| 20-1 | "Hs00705626_s1" "Hs00248075_m1" "Hs01560931_m1" "Hs00167524_m1" "Hs00366766_m1" "Hs01051445_g1" "Hs00996236_m1" "Hs01089557_s1" "Hs00262107_m1" "Hs01931732_s1" "Hs00399035_m1" "Hs00231709_m1" "Hs00411188_g1" "Hs00978280_m1" "Hs00826827_g1" "Hs00232157_m1" "Hs00747379_m1" "Hs00233987_m1" "Hs01008033_m1" "Hs04194422_s1" |
| 20-2 | "Hs00884853_s1" "Hs01920599_gH" "Hs00996236_m1" "Hs00248075_m1" "Hs00167524_m1" "Hs00747379_m1" "Hs00942584_m1" "Hs01042796_m1" "Hs00964384_g1" "Hs05052601_s1" "Hs00356958_m1" "Hs00901350_g1" "Hs01691258_g1" "Hs00992679_m1" "Hs01051611_gH" "Hs04194422_s1" "Hs01089557_s1" "Hs01087946_g1" "Hs05036222_s1" "Hs00856927_g1" |
| 20-3 | "Hs00248075_m1" "Hs00251883_m1" "Hs01089557_s1" "Hs00356958_m1" "Hs00856927_g1" "Hs00202752_m1" "Hs00950371_m1" "Hs00899658_m1" "Hs00362096_m1" "Hs01043717_m1" "Hs01560931_m1" "Hs00826827_g1" "Hs01010736_m1" "Hs00167524_m1" "Hs01031740_m1" "Hs01920599_gH" "Hs00201707_m1" "Hs00738791_g1" "Hs00962398_m1" "Hs00543973_m1" |
| 20-4 | "Hs00962398_m1" "Hs01920599_gH" "Hs01025572_m1" "Hs00159178_m1" "Hs01089557_s1" "Hs00167524_m1" "Hs00248075_m1" "Hs00386692_m1" "Hs00856927_g1" "Hs00996236_m1" "Hs01031740_m1" "Hs01010736_m1" |

TABLE 13-continued

Exemplary gene sets used to predict risk of recurrence and/or metastasis

| Gene set | Probe identifiers used for each gene set (probe identifiers from ThermoFisher Scientific). |
|---|---|
| | "Hs00900510_m1" "Hs00826827_g1" "Hs01008033_m1" "Hs00415546_m1" "Hs04942686_m1" "Hs00801390_s1" "Hs01072228_m1" "Hs01547054_m1" |
| 20-5 | "Hs00411188_g1" "Hs00248075_m1" "Hs00202752_m1" "Hs00747379_m1" "Hs01042796_m1" "Hs01920599_gH" "Hs01114274_m1" "Hs00942584_m1" "Hs00996236_m1" "Hs00167524_m1" "Hs00978280_m1" "Hs00543973_m1" "Hs00826827_g1" "Hs01560931_m1" "Hs00931763_m1" "Hs01089557_s1" "Hs00174029_m1" "Hs01029174_m1" "Hs00415546_m1" "Hs00964384_g1" |
| 20-6 | "Hs00975850_m1" "Hs04942686_m1" "Hs00202752_m1" "Hs00233987_m1" "Hs00926053_m1" "Hs00856927_g1" "Hs00992679_m1" "Hs00251883_m1" "Hs00415546_m1" "Hs00960591_m1" "Hs00901350_g1" "Hs00747379_m1" "Hs01089557_s1" "Hs00936519_m1" "Hs03043789_g1" "Hs01560931_m1" "Hs00232157_m1" "Hs00957562_m1" "Hs00248075_m1" "Hs01549976_m1" |
| 20-7 | "Hs04194422_s1" "Hs00262107_m1" "Hs01546752_g1" "Hs01920599_gH" "Hs04189864_m1" "Hs01089557_s1" "Hs01560931_m1" "Hs00705626_s1" "Hs01043717_m1" "Hs00747379_m1" "Hs00248075_m1" "Hs00856927_g1" "Hs01029174_m1" "Hs00543973_m1" "Hs01395177_m1" "Hs00260480_m1" "Hs00174029_m1" "Hs00387770_m1" "Hs01894962_s1" "Hs00745492_s1" |
| 20-8 | "Hs01560931_m1" "Hs00738791_g1" "Hs00856927_g1" "Hs00362096_m1" "Hs00826827_g1" "Hs01098278_m1" "Hs00975850_m1" "Hs00167524_m1" "Hs00260452_m1" "Hs04194422_s1" "Hs01043717_m1" "Hs00233987_m1" "Hs00703025_s1" "Hs00896999_g1" "Hs00167051_m1" "Hs00942584_m1" "Hs01087946_g1" "Hs00411188_g1" "Hs00747379_m1" "Hs05016463_s1" |
| 20-9 | "Hs00362096_m1" "Hs00942584_m1" "Hs01560931_m1" "Hs00167524_m1" "Hs00884853_s1" "Hs00248075_m1" "Hs01920599_gH" "Hs00996236_m1" "Hs00747379_m1" "Hs01089557_s1" "Hs00959010_m1" "Hs00372831_g1" "Hs04194422_s1" "Hs01043717_m1" "Hs00399035_m1" "Hs01051611_gH" "Hs01042796_m1" "Hs00968305_m1" "Hs00260452_m1" "Hs01031740_m1" |
| 20-10 | "Hs05033260_s1" "Hs00233987_m1" "Hs04194422_s1" "Hs00992679_m1" "Hs00926053_m1" "Hs00167524_m1" "Hs00202752_m1" "Hs01549976_m1" "Hs00415546_m1" "Hs01072228_m1" "Hs01691258_g1" "Hs00387770_m1" "Hs00380101_m1" "Hs00231709_m1" "Hs01920599_gH" "Hs00543973_m1" "Hs00386692_m1" "Hs00705626_s1" "Hs00196245_m1" "Hs01081598_m1" |
| 20-11 | "Hs01114274_m1" "Hs01560931_m1" "Hs00738791_g1" "Hs00931763_m1" "Hs00996236_m1" "Hs00362096_m1" "Hs00747379_m1" "Hs00411188_g1" "Hs00900510_m1" "Hs01098278_m1" "Hs00233987_m1" "Hs04194422_s1" "Hs00826827_g1" "Hs00856927_g1" "Hs00232157_m1" "Hs01010736_m1" "Hs00704853_s1" "Hs00959010_m1" "Hs00260480_m1" "Hs00915710_m1" |
| 20-12 | "Hs00992679_m1" "Hs00159178_m1" "Hs00167524_m1" "Hs00958111_m1" "Hs00901350_g1" "Hs00931763_m1" "Hs00233987_m1" "Hs01549976_m1" "Hs01894962_s1" "Hs01089557_s1" "Hs00171157_m1" "Hs00153408_m1" "Hs00248075_m1" "Hs03464469_s1" "Hs04194422_s1" "Hs00745492_s1" "Hs00366766_m1" "Hs00856927_g1" "Hs00957562_m1" "Hs01025572_m1" |
| 20-13 | "Hs01379134_m1" "Hs00362096_m1" "Hs05052601_s1" "Hs00959010_m1" "Hs00251883_m1" "Hs01089557_s1" "Hs00856927_g1" "Hs00167524_m1" "Hs00159178_m1" "Hs04942686_m1" "Hs00356958_m1" "Hs01042796_m1" "Hs03464469_s1" "Hs01029174_m1" "Hs00248075_m1" "Hs00610058_m1" "Hs01070154_m1" "Hs00703025_s1" "Hs00964384_g1" "Hs00705626_s1" |
| 20-14 | "Hs00362096_m1" "Hs00996236_m1" "Hs00931763_m1" "Hs01081598_m1" "Hs01560931_m1" "Hs00167524_m1" "Hs00543973_m1" "Hs01098278_m1" "Hs00856927_g1" "Hs03043789_g1" "Hs01089557_s1" "Hs01051445_g1" "Hs00747379_m1" "Hs01114274_m1" "Hs00826827_g1" "Hs00936519_m1" "Hs00960591_m1" "Hs00201707_m1" "Hs00899658_m1" "Hs04189864_m1" |
| 20-15 | "Hs00856927_g1" "Hs04942686_m1" "Hs00248075_m1" "Hs01029174_m1" "Hs00992679_m1" "Hs00975850_m1" "Hs03464469_s1" "Hs00167524_m1" "Hs01691258_g1" "Hs00960591_m1" "Hs01089557_s1" "Hs04194422_s1" "Hs01114274_m1" "Hs00901350_g1" "Hs00936519_m1" "Hs00233987_m1" "Hs00411188_g1" "Hs00900510_m1" "Hs00174969_m1" "Hs01070154_m1" |
| 20-16 | "Hs00826827_g1" "Hs00738791_g1" "Hs00698959_m1" "Hs00153408_m1" "Hs00167051_m1" "Hs00365956_m1" "Hs04194422_s1" "Hs00167524_m1" "Hs01560931_m1" "Hs00610058_m1" "Hs00232157_m1" "Hs00996236_m1" "Hs00705626_s1" "Hs00362096_m1" "Hs01098278_m1" "Hs00997579_m1" "Hs00559914_m1" "Hs00856927_g1" "Hs00944507_g1" "Hs00379134_m1" |
| 20-17 | "Hs00232157_m1" "Hs00543973_m1" "Hs05052601_s1" "Hs00196245_m1" "Hs01042796_m1" "Hs00411188_g1" "Hs00899658_m1" "Hs00374264_g1" "Hs01894962_s1" "Hs04194422_s1" "Hs03464469_s1" "Hs00992679_m1" "Hs00901350_g1" "Hs00362096_m1" "Hs00856927_g1" "Hs00167524_m1" "Hs01089557_s1" "Hs01931732_s1" "Hs01549976_m1" "Hs01395177_m1" |
| 20-18 | "Hs00884853_s1" "Hs00167524_m1" "Hs00978280_m1" "Hs00747379_m1" "Hs01931732_s1" "Hs00931763_m1" "Hs04942686_m1" "Hs04194422_s1" "Hs00856927_g1" "Hs00248075_m1" "Hs00901350_g1" "Hs00415546_m1" "Hs01089557_s1" "Hs01025572_m1" "Hs00231709_m1" "Hs00386692_m1" "Hs01920599_gH" "Hs00202752_m1" "Hs01029174_m1" "Hs00942584_m1" |
| 20-19 | "Hs01547054_m1" "Hs00960591_m1" "Hs03464469_s1" "Hs01560931_m1" "Hs00153408_m1" "Hs00233987_m1" "Hs01089557_s1" "Hs00366766_m1" "Hs00248075_m1" "Hs01010736_m1" "Hs00251883_m1" "Hs00996236_m1" "Hs00610058_m1" "Hs00900510_m1" "Hs01008033_m1" "Hs00978280_m1" "Hs00260452_m1" "Hs04194422_s1" "Hs00196245_m1" "Hs05052601_s1" |
| 20-20 | "Hs01098278_m1" "Hs01072228_m1" "Hs01691258_g1" "Hs00387770_m1" "Hs00543973_m1" "Hs01920599_gH" "Hs04189864_m1" "Hs05033260_s1" "Hs00856927_g1" "Hs00366766_m1" "Hs03043789_g1" "Hs04194422_s1" "Hs00202752_m1" "Hs00936519_m1" "Hs01560931_m1" "Hs00958111_m1" "Hs00251883_m1" "Hs00704853_s1" "Hs00738791_g1" "Hs00962398_m1" |
| 20-21 | "Hs01042796_m1" "Hs01560931_m1" "Hs00884853_s1" "Hs00958111_m1" "Hs00411188_g1" "Hs05052601_s1" "Hs01920599_gH" "Hs00248075_m1" "Hs00747379_m1" "Hs00996236_m1" "Hs00251883_m1" "Hs00202752_m1" "Hs01008033_m1" "Hs00201707_m1" "Hs01051445_g1" "Hs00950371_m1" "Hs01029174_m1" "Hs00232157_m1" "Hs01087946_g1" "Hs00267207_m1" |
| 20-22 | "Hs00559914_m1" "Hs00856927_g1" "Hs00978280_m1" "Hs01920599_gH" "Hs01560931_m1" "Hs00365956_m1" "Hs00610058_m1" "Hs01008033_m1" "Hs04194422_s1" "Hs00975850_m1" "Hs00204257_m1" "Hs00950371_m1" "Hs00705626_s1" "Hs01089557_s1" "Hs00196245_m1" "Hs01042796_m1" "Hs00174029_m1" "Hs01546752_g1" "Hs01098278_m1" "Hs00231709_m1" |
| 20-23 | "Hs04194422_s1" "Hs01089557_s1" "Hs00155241_m1" "Hs00942584_m1" "Hs05033260_s1" "Hs01546752_g1" "Hs01920599_gH" "Hs01560931_m1" "Hs00387770_m1" "Hs00399035_m1" "Hs00232157_m1" "Hs00931763_m1" "Hs00231709_m1" "Hs00856927_g1" "Hs00233987_m1" "Hs01098278_m1" "Hs00978280_m1" "Hs04942686_m1" "Hs00411188_g1" "Hs00201707_m1" |
| 20-24 | "Hs00232157_m1" "Hs01010736_m1" "Hs00704853_s1" "Hs00167051_m1" "Hs00738791_g1" "Hs00975850_m1" "Hs00362096_m1" "Hs00826827_g1" "Hs00233987_m1" "Hs00950371_m1" "Hs00204257_m1" "Hs01560931_m1" "Hs00196245_m1" "Hs01042796_m1" "Hs00174029_m1" "Hs00705626_s1" "Hs00856927_g1" "Hs01051445_g1" "Hs00399035_m1" "Hs05036222_s1" |
| 20-25 | "Hs00233987_m1" "Hs00380101_m1" "Hs00167524_m1" "Hs04189864_m1" "Hs00543973_m1" "Hs01920599_gH" "Hs00856927_g1" "Hs00155241_m1" "Hs01098278_m1" "Hs00703025_s1" "Hs00231709_m1" "Hs00365956_m1" "Hs00204257_m1" "Hs01395177_m1" "Hs00968305_m1" "Hs00374264_g1" "Hs00248075_m1" "Hs00202752_m1" "Hs00801390_s1" "Hs03464469_s1" |

TABLE 13-continued

Exemplary gene sets used to predict risk of recurrence and/or metastasis

| Gene set | Probe identifiers used for each gene set (probe identifiers from ThermoFisher Scientific). |
|---|---|
| 30-1 | "Hs00387770_m1" "Hs00155241_m1" "Hs00251883_m1" "Hs01560931_m1" "Hs00428732_m1" "Hs00992679_m1" "Hs00705626_s1" "Hs00356958_m1" "Hs00960591_m1" "Hs00171157_m1" "Hs01072228_m1" "Hs01051445_g1" "Hs00232157_m1" "Hs00233987_m1" "Hs04232205_s1" "Hs00559914_m1" "Hs00931763_m1" "Hs00167524_m1" "Hs00171042_m1" "Hs01089557_s1" "Hs04194422_s1" "Hs03464469_s1" "Hs00944507_g1" "Hs00196245_m1" "Hs00950371_m1" "Hs01395177_m1" "Hs01070154_m1" "Hs01051611_gH" "Hs00399035_m1" "Hs00703025_s1" |
| 30-2 | "Hs00937509_m1" "Hs00379134_m1" "Hs00899658_m1" "Hs00248075_m1" "Hs01920599_gH" "Hs04194422_s1" "Hs03043789_g1" "Hs00610058_m1" "Hs01089557_s1" "Hs00705626_s1" "Hs00362096_m1" "Hs01560931_m1" "Hs00233987_m1" "Hs00372831_g1" "Hs01072228_m1" "Hs01379134_m1" "Hs01076090_m1" "Hs04189864_m1" "Hs00957562_m1" "Hs01931732_s1" "Hs00856927_g1" "Hs01546752_g1" "Hs00171157_m1" "Hs00992679_m1" "Hs00931763_m1" "Hs00411188_g1" "Hs01008033_m1" "Hs00387770_m1" "Hs00996236_m1" "Hs00231709_m1" |
| 30-3 | "Hs00411188_g1" "Hs01395177_m1" "Hs01560931_m1" "Hs00379134_m1" "Hs00960591_m1" "Hs00745492_s1" "Hs00232157_m1" "Hs00899658_m1" "Hs00248075_m1" "Hs01010736_m1" "Hs00167524_m1" "Hs01691258_g1" "Hs00260452_m1" "Hs01070154_m1" "Hs00196245_m1" "Hs00747379_m1" "Hs01547054_m1" "Hs00950371_m1" "Hs00962398_m1" "Hs01087946_g1" "Hs00262107_m1" "Hs00260480_m1" "Hs00978280_m1" "Hs00428732_m1" "Hs00944507_g1" "Hs00387770_m1" "Hs00399035_m1" "Hs00738791_g1" "Hs00698959_m1" "Hs01549976_m1" |
| 30-4 | "Hs00415546_m1" "Hs00705626_s1" "Hs00204257_m1" "Hs00174969_m1" "Hs00745492_s1" "Hs01920599_gH" "Hs00387770_m1" "Hs01560931_m1" "Hs00958111_m1" "Hs01076090_m1" "Hs00379134_m1" "Hs00196245_m1" "Hs00232157_m1" "Hs01549976_m1" "Hs00801390_s1" "Hs00399035_m1" "Hs01089557_s1" "Hs00607978_s1" "Hs00960591_m1" "Hs00171157_m1" "Hs05033260_s1" "Hs00233987_m1" "Hs00904817_m1" "Hs01031740_m1" "Hs05016463_s1" "Hs00153408_m1" "Hs00968305_m1" "Hs00174029_m1" "Hs00944507_g1" "Hs00248075_m1" |
| 30-5 | "Hs05033260_s1" "Hs00362096_m1" "Hs00559914_m1" "Hs01560931_m1" "Hs00968305_m1" "Hs00931763_m1" "Hs04942686_m1" "Hs01920599_gH" "Hs00899658_m1" "Hs00248075_m1" "Hs00958111_m1" "Hs05016463_s1" "Hs03464469_s1" "Hs01931732_s1" "Hs01076090_m1" "Hs00992679_m1" "Hs00901350_g1" "Hs00937509_m1" "Hs00960591_m1" "Hs01114274_m1" "Hs01043717_m1" "Hs00167524_m1" "Hs01089557_s1" "Hs00204257_m1" "Hs00703025_s1" "Hs01549976_m1" "Hs01031740_m1" ""Hs00262107_m1" Hs00957562_m1" "Hs01029174_m1" |
| 30-6 | "Hs00958111_m1" "Hs00411188_g1" "Hs05036222_s1" "Hs00386692_m1" "Hs00745492_s1" "Hs01010736_m1" "Hs00997579_m1" "Hs00222415_m1" "Hs03464469_s1" "Hs00233987_m1" "Hs01547054_m1" "Hs00202752_m1" "Hs01025572_m1" "Hs00379134_m1" "Hs04194422_s1" "Hs00926053_m1" "Hs01560931_m1" "Hs00705626_s1" "Hs01920599_gH" "Hs00171042_m1" "Hs03043789_g1" "Hs00610058_m1" "Hs01089557_s1" "Hs00362096_m1" "Hs00380101_m1" "Hs00899658_m1" "Hs00801390_s1" "Hs00374264_g1" "Hs00964384_g1" "Hs00240906_m1" |
| 30-7 | "Hs00704853_s1" "Hs01560931_m1" "Hs01379134_m1" "Hs00958111_m1" "Hs00386692_m1" "Hs04942686_m1" "Hs00747379_m1" "Hs00167524_m1" "Hs03302824_pri" "Hs00248075_m1" "Hs00387770_m1" "Hs00978280_m1" "Hs00379134_m1" "Hs00233987_m1" "Hs00992679_m1" "Hs01931732_s1" "Hs00380101_m1" "Hs00705626_s1" "Hs00155241_m1" "Hs05033260_s1" "Hs01089557_s1" "Hs00171157_m1" "Hs00745492_s1" "Hs00937509_m1" "Hs00374264_g1" "Hs00240906_m1" "Hs01098278_m1" "Hs00174705_m1" "Hs00260480_m1" "Hs00372831_g1" |
| 30-8 | "Hs00202752_m1" "Hs00231709_m1" "Hs00366766_m1" "Hs00201707_m1" "Hs00826827_g1" "Hs00856927_g1" "Hs00174969_m1" "Hs00387770_m1" "Hs00167524_m1" "Hs01031740_m1" "Hs03464469_s1" "Hs01025572_m1" "Hs00996236_m1" "Hs00950371_m1" "Hs00610058_m1" "Hs01920599_gH" "Hs01051445_g1" "Hs00975850_m1" "Hs00978280_m1" "Hs00167051_m1" "Hs01560931_m1" "Hs00704853_s1" "Hs00902334_m1" "Hs01553775_g1" "Hs00962398_m1" "Hs01098278_m1" "Hs00356958_m1" "Hs01087946_g1" "Hs01029174_m1" "Hs00747379_m1" |
| 30-9 | "Hs00362096_m1" "Hs01560931_m1" "Hs04942686_m1" "Hs05033260_s1" "Hs00958111_m1" "Hs00232157_m1" "Hs00899658_m1" "Hs00607978_s1" "Hs01549976_m1" "Hs00262107_m1" "Hs00968305_m1" "Hs00233987_m1" "Hs00904817_m1" "Hs00356958_m1" "Hs00900510_m1" "Hs00174969_m1" "Hs04194422_s1" "Hs01043717_m1" "Hs00745492_s1" "Hs00171042_m1" "Hs00379134_m1" "Hs00559914_m1" "Hs04232205_s1" "Hs00957562_m1" "Hs00167051_m1" "Hs05052601_s1" "Hs00380101_m1" "Hs01546752_g1" "Hs00801390_s1" "Hs01070154_m1" |
| 30-10 | "Hs00380101_m1" "Hs03464469_s1" "Hs00372831_g1" "Hs05052601_s1" "Hs04189864_m1" "Hs00248075_m1" "Hs00968305_m1" "Hs04942686_m1" "Hs00159178_m1" "Hs00386692_m1" "Hs00937509_m1" "Hs00960591_m1" "Hs00543973_m1" "Hs01894962_s1" "Hs00233987_m1" "Hs01051445_g1" "Hs01560931_m1" "Hs01089557_s1" "Hs00232157_m1" "Hs00387770_m1" "Hs01025572_m1" "Hs01395177_m1" "Hs00801390_s1" "Hs00884853_s1" "Hs01072228_m1" "Hs00201707_m1" "Hs00996236_m1" "Hs01114274_m1" "Hs00747379_m1" "Hs00167051_m1" |
| 30-11 | "Hs00801390_s1" "Hs01920599_gH" "Hs00931763_m1" "Hs00262107_m1" "Hs04942686_m1" "Hs00233987_m1" "Hs00399035_m1" "Hs00248075_m1" "Hs00171157_m1" "Hs00167524_m1" "Hs00899658_m1" "Hs00232157_m1" "Hs00362096_m1" "Hs00915710_m1" "Hs00174969_m1" "Hs00900510_m1" "Hs00387770_m1" "Hs00428732_m1" "Hs00607978_s1" "Hs00380101_m1" "Hs00260480_m1" "Hs00996236_m1" "Hs00958111_m1" "Hs01070154_m1" "Hs00543973_m1" "Hs00937509_m1" "Hs01089557_s1" "Hs00968305_m1" "Hs01072228_m1" "Hs01042796_m1" |
| 30-12 | "Hs00745492_s1" "Hs00950371_m1" "Hs00233987_m1" "Hs01560931_m1" "Hs00379134_m1" "Hs00167524_m1" "Hs00826827_g1" "Hs00978280_m1" "Hs00904817_m1" "Hs00856927_g1" "Hs00899658_m1" "Hs01008033_m1" "Hs00931763_m1" "Hs00365956_m1" "Hs03302824_pri" "Hs00428732_m1" "Hs00975850_m1" "Hs01894962_s1" "Hs00703025_s1" "Hs01072228_m1" "Hs01098278_m1" "Hs00958111_m1" "Hs00944507_g1" "Hs01010736_m1" "Hs00996236_m1" "Hs01920599_gH" "Hs00387770_m1" "Hs01547054_m1" "Hs00610058_m1" "Hs01087946_g1" |
| 30-13 | "Hs00856927_g1" "Hs00915710_m1" "Hs00379134_m1" "Hs00233987_m1" "Hs01008033_m1" "Hs00167524_m1" "Hs00899658_m1" "Hs00559914_m1" "Hs00904817_m1" "Hs04942686_m1" "Hs00386692_m1" "Hs00704853_s1" "Hs00978280_m1" "Hs00415546_m1" "Hs00399035_m1" "Hs00374264_g1" "Hs01560931_m1" "Hs01546752_g1" "Hs00231709_m1" "Hs00387770_m1" "Hs00964384_g1" "Hs00698959_m1" "Hs00196245_m1" "Hs01395177_m1" "Hs01076090_m1" "Hs00201707_m1" "Hs03302824_pri" "Hs00703025_s1" "Hs01114274_m1" "Hs01631495_s1" |
| 30-14 | "Hs00380101_m1" "Hs00232157_m1" "Hs00428732_m1" "Hs03302824_pri" "Hs01031740_m1" "Hs00171042_m1" "Hs01549976_m1" "Hs00260452_m1" "Hs00745492_s1" "Hs00411188_g1" "Hs00167524_m1" "Hs01560931_m1" "Hs00356958_m1" "Hs00559914_m1" "Hs00262107_m1" "Hs03464469_s1" "Hs00801390_s1" "Hs00202752_m1" "Hs00233987_m1" "Hs00196245_m1" "Hs00960591_m1" "Hs01546752_g1" "Hs01087946_g1" "Hs01547054_m1" "Hs00260480_m1" "Hs01070154_m1" "Hs00267207_m1" "Hs00174705_m1" "Hs00747379_m1" "Hs00387770_m1" |
| 30-15 | "Hs00960591_m1" "Hs00231709_m1" "Hs00251883_m1" "Hs00387770_m1" "Hs00356958_m1" "Hs00196245_m1" "Hs00174969_m1" "Hs00996236_m1" "Hs00559914_m1" "Hs00962398_m1" "Hs00856927_g1" "Hs00826827_g1" "Hs01025572_m1" "Hs00801390_s1" "Hs03043789_g1" "Hs00950371_m1" "Hs00233987_m1" "Hs00202752_m1" "Hs00260480_m1" "Hs00944507_g1" "Hs00978280_m1" "Hs01894962_s1" "Hs00204257_m1" "Hs00174029_m1" "Hs00703025_s1" "Hs01051611_gH" "Hs00958111_m1" "Hs00262107_m1" "Hs00167524_m1" "Hs01098278_m1" |

TABLE 13-continued

Exemplary gene sets used to predict risk of recurrence and/or metastasis

| Gene set | Probe identifiers used for each gene set (probe identifiers from ThermoFisher Scientific). |
|---|---|
| 30-16 | "Hs00944507_g1" "Hs05016463_s1" "Hs03464469_s1" "Hs00167051_m1" "Hs00900510_m1" "Hs00904817_m1" "Hs04232205_s1" "Hs00356958_m1" "Hs00957562_m1" "Hs00745492_s1" "Hs00931763_m1" "Hs01043717_m1" "Hs00167524_m1" "Hs00856927_g1" "Hs00992679_m1" "Hs00380101_m1" "Hs01549976_m1" "Hs00559914_m1" "Hs01560931_m1" "Hs01098278_m1" "Hs00703025_s1" "Hs00248075_m1" "Hs01081598_m1" "Hs00428732_m1" "Hs00968305_m1" "Hs00705626_s1" "Hs00386692_m1" "Hs00174705_m1" "Hs00251883_m1" "Hs00415546_m1" |
| 30-17 | "Hs00543973_m1" "Hs00159178_m1" "Hs01098278_m1" "Hs00399035_m1" "Hs01029174_m1" "Hs00705626_s1" "Hs03302824_pri" "Hs01051611_gH" "Hs05033260_s1" "Hs01560931_m1" "Hs00167524_m1" "Hs01042796_m1" "Hs05052601_s1" "Hs00944507_g1" "Hs00978280_m1" "Hs00747379_m1" "Hs01071042_m1" "Hs00251883_m1" "Hs00960591_m1" "Hs01072228_m1" "Hs03043789_g1" "Hs00233987_m1" "Hs04942686_m1" "Hs00801390_s1" "Hs00992679_m1" "Hs01010736_m1" "Hs00232157_m1" "Hs00896999_g1" "Hs00826827_g1" "Hs00231709_m1" |
| 30-18 | "Hs01920599_gH" "Hs00248075_m1" "Hs00411188_g1" "Hs01560931_m1" "Hs00900510_m1" "Hs00996236_m1" "Hs00745492_s1" "Hs00202752_m1" "Hs00233987_m1" "Hs00222415_m1" "Hs01089557_s1" "Hs05052601_s1" "Hs00960591_m1" "Hs00958111_m1" "Hs01379134_m1" "Hs00380101_m1" "Hs00856927_g1" "Hs04189864_m1" "Hs01031740_m1" "Hs01042796_m1" "Hs01098278_m1" "Hs01395177_m1" "Hs00950371_m1" "Hs01691258_g1" "Hs00899658_m1" "Hs00962398_m1" "Hs00240906_m1" "Hs00399035_m1" "Hs00428732_m1" "Hs04942686_m1" |
| 30-19 | "Hs00428732_m1" "Hs01560931_m1" "Hs01025572_m1" "Hs00232157_m1" "Hs01089557_s1" "Hs01043717_m1" "Hs00705626_s1" "Hs00884853_s1" "Hs00543973_m1" "Hs00992679_m1" "Hs00899658_m1" "Hs00233987_m1" "Hs00745492_s1" "Hs01031740_m1" "Hs01076090_m1" "Hs00260480_m1" "Hs00856927_g1" "Hs00189880_m1" "Hs00231709_m1" "Hs01920599_gH" "Hs00171042_m1" "Hs00415546_m1" "Hs01894962_s1" "Hs04189864_m1" "Hs00174969_m1" "Hs00610058_m1" "Hs00153408_m1" "Hs01379134_m1" "Hs00915710_m1" "Hs01395177_m1" |
| 30-20 | "Hs00267207_m1" "Hs00366766_m1" "Hs04942686_m1" "Hs00231709_m1" "Hs01098278_m1" "Hs05016463_s1" "Hs00155241_m1" "Hs00900510_m1" "Hs00975850_m1" "Hs04194422_s1" "Hs01114274_m1" "Hs01072228_m1" "Hs01089557_s1" "Hs00747379_m1" "Hs00944507_g1" "Hs00705626_s1" "Hs00202752_m1" "Hs00978280_m1" "Hs01920599_gH" "Hs00196245_m1" "Hs04189864_m1" "Hs01025572_m1" "Hs05052601_s1" "Hs00380101_m1" "Hs01081598_m1" "Hs00372831_g1" "Hs00167051_m1" "Hs00232157_m1" "Hs01553775_g1" "Hs00738791_g1" |
| 30-21 | "Hs00174705_m1" "Hs01042796_m1" "Hs00856927_g1" "Hs00372831_g1" "Hs03302824_pri" "Hs05033260_s1" "Hs04189864_m1" "Hs00992679_m1" "Hs01560931_m1" "Hs00159178_m1" "Hs00196245_m1" "Hs05052601_s1" "Hs01031740_m1" "Hs00233987_m1" "Hs00975850_m1" "Hs01098278_m1" "Hs00248075_m1" "Hs00167524_m1" "Hs00171042_m1" "Hs01920599_gH" "Hs00380101_m1" "Hs00559914_m1" "Hs04942686_m1" "Hs00202752_m1" "Hs00937509_m1" "Hs00978280_m1" "Hs00936519_m1" "Hs00222415_m1" "Hs00365956_m1" "Hs00379134_m1" |
| 30-22 | "Hs00380101_m1" "Hs00233987_m1" "Hs00171042_m1" "Hs00411188_g1" "Hs00248075_m1" "Hs00559914_m1" "Hs00826827_g1" "Hs01894962_s1" "Hs01098278_m1" "Hs00232157_m1" "Hs01920599_gH" "Hs00975850_m1" "Hs00356958_m1" "Hs00543973_m1" "Hs01029174_m1" "Hs00159178_m1" "Hs05052601_s1" "Hs04194422_s1" "Hs01025572_m1" "Hs00950371_m1" "Hs00167524_m1" "Hs01072228_m1" "Hs00900510_m1" "Hs00705626_s1" "Hs01114274_m1" "Hs00904817_m1" "Hs00231709_m1" "Hs00745492_s1" "Hs00155241_m1" "Hs01081598_m1" |
| 30-23 | "Hs00964384_g1" "Hs00899658_m1" "Hs00374264_g1" "Hs00399035_m1" "Hs00703025_s1" "Hs00415546_m1" "Hs00232157_m1" "Hs00387770_m1" "Hs00826827_g1" "Hs01395177_m1" "Hs00202752_m1" "Hs00171042_m1" "Hs00996236_m1" "Hs00937509_m1" "Hs05016463_s1" "Hs00233987_m1" "Hs01114274_m1" "Hs01042796_m1" "Hs00248075_m1" "Hs00957562_m1" "Hs00196245_m1" "Hs01560931_m1" "Hs01089557_s1" "Hs00222415_m1" "Hs04194422_s1" "Hs01931732_s1" "Hs00884853_s1" "Hs00978280_m1" "Hs00959010_m1" "Hs00559914_m1" |
| 30-24 | "Hs01042796_m1" "Hs00801390_s1" "Hs00960591_m1" "Hs00992679_m1" "Hs00978280_m1" "Hs00937509_m1" "Hs01931732_s1" "Hs01560931_m1" "Hs05016463_s1" "Hs00171157_m1" "Hs00167524_m1" "Hs00260452_m1" "Hs01089557_s1" "Hs00232157_m1" "Hs00899658_m1" "Hs00904817_m1" "Hs00202752_m1" "Hs00958111_m1" "Hs00968305_m1" "Hs00248075_m1" "Hs00607978_s1" "Hs04942686_m1" "Hs01920599_gH" "Hs00365956_m1" "Hs00944507_g1" "Hs01043717_m1" "Hs00745492_s1" "Hs00704853_s1" "Hs00610058_m1" "Hs04194422_s1" |
| 30-25 | "Hs00738791_g1" "Hs04232205_s1" "Hs00362096_m1" "Hs00260452_m1" "Hs01547054_m1" "Hs00196245_m1" "Hs01560931_m1" "Hs00964384_g1" "Hs00415546_m1" "Hs00202752_m1" "Hs03043789_g1" "Hs00997579_m1" "Hs00745492_s1" "Hs00174029_m1" "Hs04194422_s1" "Hs00899658_m1" "Hs00251883_m1" "Hs00915710_m1" "Hs01042796_m1" "Hs04942686_m1" "Hs00248075_m1" "Hs00222415_m1" "Hs01081598_m1" "Hs01089557_s1" "Hs00705626_s1" "Hs00356958_m1" "Hs00204257_m1" "Hs00926053_m1" "Hs05052601_s1" "Hs00372831_g1" |
| 40-1 | "Hs00262107_m1" "Hs01560931_m1" "Hs00159178_m1" "Hs00975850_m1" "Hs00366766_m1" "Hs00543973_m1" "Hs00231709_m1" "Hs00372831_g1" "Hs00745492_s1" "Hs01072228_m1" "Hs04194422_s1" "Hs00174029_m1" "Hs00171157_m1" "Hs01029174_m1" "Hs01089557_s1" "Hs00801390_s1" "Hs00958111_m1" "Hs01098278_m1" "Hs01920599_gH" "Hs00233987_m1" "Hs00374264_g1" "Hs04189864_m1" "Hs00155241_m1" "Hs00610058_m1" "Hs03464469_s1" "Hs00386692_m1" "Hs00964384_g1" "Hs01025572_m1" "Hs01546752_g1" "Hs01395177_m1" "Hs00248075_m1" "Hs00937509_m1" "Hs00704853_s1" "Hs03028557_s1" "Hs00747379_m1" "Hs00904817_m1" "Hs00362096_m1" "Hs01087946_g1" "Hs01031740_m1" "Hs00978280_m1" |
| 40-2 | "Hs00231709_m1" "Hs01098278_m1" "Hs00174969_m1" "Hs01029174_m1" "Hs05036222_s1" "Hs00262107_m1" "Hs00856927_g1" "Hs05052601_s1" "Hs00233987_m1" "Hs00559914_m1" "Hs01931732_s1" "Hs01560931_m1" "Hs00167524_m1" "Hs00543973_m1" "Hs01010736_m1" "Hs00174029_m1" "Hs00260480_m1" "Hs00996236_m1" "Hs00745492_s1" "Hs00204257_m1" "Hs00374264_g1" "Hs04942686_m1" "Hs00411188_g1" "Hs00380101_m1" "Hs01051611_gH" "Hs01089557_s1" "Hs00901350_g1" "Hs01081598_m1" "Hs00738791_g1" "Hs01025572_m1" "Hs00248075_m1" "Hs01894962_s1" "Hs00957562_m1" "Hs00189880_m1" "Hs00937509_m1" "Hs00362096_m1" "Hs00962398_m1" "Hs00171042_m1" "Hs01076090_m1" "Hs00801390_s1" |
| 40-3 | "Hs00978280_m1" "Hs00900510_m1" "Hs00411188_g1" "Hs00174969_m1" "Hs00171157_m1" "Hs01546752_g1" "Hs04194422_s1" "Hs00826827_g1" "Hs01010736_m1" "Hs01043717_m1" "Hs00931763_m1" "Hs01089557_s1" "Hs00703025_s1" "Hs00559914_m1" "Hs03302824_pri" "Hs01087946_g1" "Hs00950371_m1" "Hs01051445_g1" "Hs00202752_m1" "Hs00380101_m1" "Hs01553775_g1" "Hs00232157_m1" "Hs00698959_m1" "Hs01098278_m1" "Hs03464469_s1" "Hs00884853_s1" "Hs00926053_m1" "Hs00936519_m1" "Hs00745492_s1" "Hs01560931_m1" "Hs00362096_m1" "Hs00204257_m1" "Hs00240906_m1" "Hs00366766_m1" "Hs00260480_m1" "Hs01549976_m1" "Hs00997579_m1" "Hs00738791_g1" "Hs01114274_m1" "Hs03043789_g1" |
| 40-4 | "Hs00899658_m1" "Hs00543973_m1" "Hs00260452_m1" "Hs00233987_m1" "Hs03302824_pri" "Hs04189864_m1" "Hs01089557_s1" "Hs05036222_s1" "Hs00428732_m1" "Hs00374264_g1" "Hs00958111_m1" "Hs00167524_m1" "Hs00856927_g1" "Hs00964384_g1" "Hs00900510_m1" "Hs00747379_m1" "Hs01087946_g1" "Hs05033260_s1" "Hs00607978_s1" "Hs04942686_m1" "Hs00937509_m1" "Hs00380101_m1" "Hs00386692_m1" "Hs00155241_m1" |

TABLE 13-continued

Exemplary gene sets used to predict risk of recurrence and/or metastasis

| Gene set | Probe identifiers used for each gene set (probe identifiers from ThermoFisher Scientific). |
|---|---|
|  | "Hs01114274_m1" "Hs03028557_s1" "Hs00240906_m1" "Hs01546752_g1" "Hs00975850_m1" "Hs00610058_m1" "Hs01631495_s1" "Hs00174029_m1" "Hs00411188_g1" "Hs00559914_m1" "Hs03043789_g1" "Hs00698959_m1" "Hs00703025_s1" "Hs00745492_s1" "Hs00387770_m1" "Hs01008033_m1" |
| 40-5 | "Hs00607978_s1" "Hs01031740_m1" "Hs00174969_m1" "Hs01114274_m1" "Hs04942686_m1" "Hs00931763_m1" "Hs00996236_m1" "Hs01395177_m1" "Hs01098278_m1" "Hs00387770_m1" "Hs04194422_s1" "Hs00248075_m1" "Hs01546752_g1" "Hs00705626_s1" "Hs01920599_gH" "Hs00801390_s1" "Hs05052601_s1" "Hs00960591_m1" "Hs01076090_m1" "Hs00232157_m1" "Hs00262107_m1" "Hs00944507_g1" "Hs00174705_m1" "Hs01089557_s1" "Hs01029174_m1" "Hs01051445_g1" "Hs00362096_m1" "Hs00399035_m1" "Hs00745492_s1" "Hs00978280_m1" "Hs01043717_m1" "Hs03028557_s1" "Hs00233987_m1" "Hs00704853_s1" "Hs01008033_m1" "Hs00543973_m1" "Hs00251883_m1" "Hs01691258_g1" "Hs00155241_m1" "Hs01042796_m1" |
| 40-6 | "Hs01931732_s1" "Hs00174705_m1" "Hs00248075_m1" "Hs00174969_m1" "Hs00950371_m1" "Hs00374264_g1" "Hs00232157_m1" "Hs00747379_m1" "Hs00884853_s1" "Hs00411188_g1" "Hs01089557_s1" "Hs00196245_m1" "Hs01029174_m1" "Hs01560931_m1" "Hs00379134_m1" "Hs04942686_m1" "Hs00738791_g1" "Hs00960591_m1" "Hs00171042_m1" "Hs05016463_s1" "Hs01025572_m1" "Hs00260480_m1" "Hs00428732_m1" "Hs00705626_s1" "Hs01114274_m1" "Hs00153408_m1" "Hs00944507_g1" "Hs00171157_m1" "Hs00962398_m1" "Hs00975850_m1" "Hs00997579_m1" "Hs00931763_m1" "Hs01379134_m1" "Hs04194422_s1" "Hs00703025_s1" "Hs01553775_g1" "Hs00365956_m1" "Hs01098278_m1" "Hs00559914_m1" "Hs00992679_m1" |
| 40-7 | "Hs00387770_m1" "Hs01031740_m1" "Hs00356958_m1" "Hs00959010_m1" "Hs01395177_m1" "Hs00705626_s1" "Hs01010736_m1" "Hs00703025_s1" "Hs00801390_s1" "Hs01894962_s1" "Hs00233987_m1" "Hs00174029_m1" "Hs00196245_m1" "Hs01051445_g1" "Hs00153408_m1" "Hs01081598_m1" "Hs00411188_g1" "Hs01089557_s1" "Hs01920599_gH" "Hs00901350_g1" "Hs00950371_m1" "Hs00997579_m1" "Hs00415546_m1" "Hs00884853_s1" "Hs00155241_m1" "Hs00915710_m1" "Hs03302824_pri" "Hs01025572_m1" "Hs00698959_m1" "Hs00167524_m1" "Hs00936519_m1" "Hs00992679_m1" "Hs00704853_s1" "Hs00960591_m1" "Hs00968305_m1" "Hs00380101_m1" "Hs00745492_s1" "Hs00201707_m1" "Hs00996236_m1" "Hs00366766_m1" |
| 40-8 | "Hs00155241_m1" "Hs01025572_m1" "Hs01087946_g1" "Hs00204257_m1" "Hs01395177_m1" "Hs05052601_s1" "Hs00962398_m1" "Hs03028557_s1" "Hs05033260_s1" "Hs00610058_m1" "Hs00174029_m1" "Hs05036222_s1" "Hs04189864_m1" "Hs00543973_m1" "Hs01081598_m1" "Hs01894962_s1" "Hs00738791_g1" "Hs00171042_m1" "Hs00957562_m1" "Hs01560931_m1" "Hs00231709_m1" "Hs01098278_m1" "Hs00703025_s1" "Hs01089557_s1" "Hs00374264_g1" "Hs01010736_m1" "Hs00901350_g1" "Hs00174969_m1" "Hs00260480_m1" "Hs00996236_m1" "Hs05016463_s1" "Hs00415546_m1" "Hs00362096_m1" "Hs00704853_s1" "Hs00975850_m1" "Hs00174705_m1" "Hs00251883_m1" "Hs00196245_m1" "Hs00222415_m1" "Hs01931732_s1" |
| 40-9 | "Hs00267207_m1" "Hs00904817_m1" "Hs01087946_g1" "Hs00233987_m1" "Hs04194422_s1" "Hs00196245_m1" "Hs03302824_pri" "Hs01089557_s1" "Hs00936519_m1" "Hs01560931_m1" "Hs00559914_m1" "Hs00171157_m1" "Hs00900510_m1" "Hs00174705_m1" "Hs00856927_g1" "Hs00950371_m1" "Hs01043717_m1" "Hs00960591_m1" "Hs01546752_g1" "Hs00957562_m1" "Hs00372831_g1" "Hs01029174_m1" "Hs00937509_m1" "Hs00411188_g1" "Hs05016463_s1" "Hs00705626_s1" "Hs00232157_m1" "Hs00174029_m1" "Hs00978280_m1" "Hs05052601_s1" "Hs05033260_s1" "Hs01920599_gH" "Hs00231709_m1" "Hs01098278_m1" "Hs01081598_m1" "Hs00997579_m1" "Hs01051445_g1" "Hs04232205_s1" "Hs00884853_s1" "Hs00738791_g1" |
| 40-10 | "Hs01076090_m1" "Hs00387770_m1" "Hs01031740_m1" "Hs00196245_m1" "Hs03464469_s1" "Hs04232205_s1" "Hs00884853_s1" "Hs00174969_m1" "Hs00607978_s1" "Hs04942686_m1" "Hs00931763_m1" "Hs01098278_m1" "Hs00996236_m1" "Hs00960591_m1" "Hs01920599_gH" "Hs01546752_g1" "Hs00997579_m1" "Hs01087946_g1" "Hs01560931_m1" "Hs00950371_m1" "Hs01549976_m1" "Hs00747379_m1" "Hs01081598_m1" "Hs01691258_g1" "Hs00231709_m1" "Hs00399035_m1" "Hs00428732_m1" "Hs00543973_m1" "Hs00240906_m1" "Hs00372831_g1" "Hs00703025_s1" "Hs00171042_m1" "Hs01043717_m1" "Hs01025572_m1" "Hs00222415_m1" "Hs00937509_m1" "Hs00267207_m1" "Hs00915710_m1" "Hs00366766_m1" "Hs00610058_m1" |
| 40-11 | "Hs00610058_m1" "Hs00745492_s1" "Hs00901350_g1" "Hs01051611_gH" "Hs01087946_g1" "Hs05052601_s1" "Hs03028557_s1" "Hs00248075_m1" "Hs01089557_s1" "Hs00738791_g1" "Hs00374264_g1" "Hs00543973_m1" "Hs04189864_m1" "Hs00698959_m1" "Hs05036222_s1" "Hs00962398_m1" "Hs00362096_m1" "Hs03043789_g1" "Hs03302824_pri" "Hs00380101_m1" "Hs00232157_m1" "Hs01553775_g1" "Hs01547054_m1" "Hs00174705_m1" "Hs00936519_m1" "Hs00386692_m1" "Hs00926053_m1" "Hs00996236_m1" "Hs00960591_m1" "Hs01098278_m1" "Hs01560931_m1" "Hs00202752_m1" "Hs04942686_m1" "Hs00428732_m1" "Hs01072228_m1" "Hs00884853_s1" "Hs00931763_m1" "Hs00964384_g1" "Hs00826827_g1" "Hs00155241_m1" |
| 40-12 | "Hs00174705_m1" "Hs00698959_m1" "Hs01546752_g1" "Hs00262107_m1" "Hs03464469_s1" "Hs00996236_m1" "Hs00960591_m1" "Hs00387770_m1" "Hs00204257_m1" "Hs00801390_s1" "Hs00610058_m1" "Hs01631495_s1" "Hs01081598_m1" "Hs00240906_m1" "Hs01553775_g1" "Hs00362096_m1" "Hs00899658_m1" "Hs00248075_m1" "Hs01894962_s1" "Hs01089557_s1" "Hs00747379_m1" "Hs01560931_m1" "Hs00267207_m1" "Hs01010736_m1" "Hs00901350_g1" "Hs03302824_pri" "Hs01547054_m1" "Hs00386692_m1" "Hs01098278_m1" "Hs00399035_m1" "Hs00189880_m1" "Hs00232157_m1" "Hs00356958_m1" "Hs00167524_m1" "Hs00380101_m1" "Hs04942686_m1" "Hs00174969_m1" "Hs00968305_m1" "Hs00745492_s1" "Hs00366766_m1" |
| 40-13 | "Hs01546752_g1" "Hs01920599_gH" "Hs00801390_s1" "Hs01560931_m1" "Hs04194422_s1" "Hs01081598_m1" "Hs00251883_m1" "Hs00559914_m1" "Hs00262107_m1" "Hs00374264_g1" "Hs00543973_m1" "Hs00171157_m1" "Hs00937509_m1" "Hs01029174_m1" "Hs00174969_m1" "Hs00232157_m1" "Hs00705626_s1" "Hs05016463_s1" "Hs01553775_g1" "Hs00704853_s1" "Hs01691258_g1" "Hs00167524_m1" "Hs00962398_m1" "Hs00978280_m1" "Hs00248075_m1" "Hs00386692_m1" "Hs00959010_m1" "Hs01098278_m1" "Hs00884853_s1" "Hs00174705_m1" "Hs00996236_m1" "Hs00379134_m1" "Hs04942686_m1" "Hs00202752_m1" "Hs00189880_m1" "Hs00365956_m1" "Hs03302824_pri" "Hs00926053_m1" "Hs01395177_m1" "Hs04189864_m1" |
| 40-14 | "Hs00747379_m1" "Hs00362096_m1" "Hs00386692_m1" "Hs01089557_s1" "Hs01029174_m1" "Hs00960591_m1" "Hs00248075_m1" "Hs01547054_m1" "Hs01631495_s1" "Hs00189880_m1" "Hs00167524_m1" "Hs01098278_m1" "Hs00996236_m1" "Hs00240906_m1" "Hs01087946_g1" "Hs00884853_s1" "Hs00899658_m1" "Hs00380101_m1" "Hs04942686_m1" "Hs00936519_m1" "Hs00856927_g1" "Hs01043717_m1" "Hs00915710_m1" "Hs00231709_m1" "Hs00964384_g1" "Hs00387770_m1" "Hs00155241_m1" "Hs01081598_m1" "Hs00926053_m1" "Hs00366766_m1" "Hs00171042_m1" "Hs01031740_m1" "Hs00959010_m1" "Hs01546752_g1" "Hs00233987_m1" "Hs01042796_m1" "Hs00896999_g1" "Hs00374264_g1" "Hs04232205_s1" "Hs00201707_m1" |

TABLE 13-continued

Exemplary gene sets used to predict risk of recurrence and/or metastasis

| Gene set | Probe identifiers used for each gene set (probe identifiers from ThermoFisher Scientific). |
|---|---|
| 40-15 | "Hs00703025_s1" "Hs01087946_g1" "Hs05016463_s1" "Hs00167524_m1" "Hs00543973_m1" "Hs01010736_m1" "Hs05052601_s1" "Hs00957562_m1" "Hs00856927_g1" "Hs04232205_s1" "Hs01029174_m1" "Hs00251883_m1" "Hs01931732_s1" "Hs00262107_m1" "Hs00374264_g1" "Hs01560931_m1" "Hs00174969_m1" "Hs00937509_m1" "Hs00222415_m1" "Hs00801390_s1" "Hs00959010_m1" "Hs00231709_m1" "Hs00747379_m1" "Hs00411188_g1" "Hs01051445_g1" "Hs00174029_m1" "Hs01553775_g1" "Hs01072228_m1" "Hs01089557_s1" "Hs00415546_m1" "Hs00705626_s1" "Hs00387770_m1" "Hs00745492_s1" "Hs00153408_m1" "Hs00196245_m1" "Hs00884853_s1" "Hs04189864_m1" "Hs00936519_m1" "Hs00958111_m1" "Hs00607978_s1" |
| 40-16 | "Hs01920599_gH" "Hs04189864_m1" "Hs01114274_m1" "Hs01395177_m1" "Hs00374264_g1" "Hs00174029_m1" "Hs00958111_m1" "Hs03028557_s1" "Hs00856927_g1" "Hs00153408_m1" "Hs01089557_s1" "Hs00607978_s1" "Hs00201707_m1" "Hs00155241_m1" "Hs00233987_m1" "Hs00745492_s1" "Hs00610058_m1" "Hs00964384_g1" "Hs04942686_m1" "Hs00996236_m1" "Hs00174969_m1" "Hs00944507_g1" "Hs00248075_m1" "Hs00362096_m1" "Hs00174705_m1" "Hs01043717_m1" "Hs00260452_m1" "Hs00167524_m1" "Hs00380101_m1" "Hs00559914_m1" "Hs00159178_m1" "Hs04194422_s1" "Hs00399035_m1" "Hs01931732_s1" "Hs00703025_s1" "Hs00738791_g1" "Hs00826827_g1" "Hs00997579_m1" "Hs00204257_m1" "Hs01070154_m1" |
| 40-17 | "Hs00978280_m1" "Hs01553775_g1" "Hs01029174_m1" "Hs00996236_m1" "Hs00386692_m1" "Hs00738791_g1" "Hs01089557_s1" "Hs00365956_m1" "Hs00607978_s1" "Hs00248075_m1" "Hs01098278_m1" "Hs00962398_m1" "Hs00196245_m1" "Hs00232157_m1" "Hs00167524_m1" "Hs04942686_m1" "Hs00201707_m1" "Hs00915710_m1" "Hs01549976_m1" "Hs00901350_g1" "Hs04194422_s1" "Hs00997579_m1" "Hs01031740_m1" "Hs00904817_m1" "Hs01631495_s1" "Hs00153408_m1" "Hs00975850_m1" "Hs00428732_m1" "Hs00366766_m1" "Hs04232205_s1" "Hs01547054_m1" "Hs00900510_m1" "Hs01560931_m1" "Hs00747379_m1" "Hs00356958_m1" "Hs00899658_m1" "Hs00415546_m1" "Hs00362096_m1" "Hs00937509_m1" "Hs00958111_m1" |
| 40-18 | "Hs00201707_m1" "Hs04942686_m1" "Hs04194422_s1" "Hs00899658_m1" "Hs00260452_m1" "Hs01043717_m1" "Hs00262107_m1" "Hs01070154_m1" "Hs01029174_m1" "Hs00856927_g1" "Hs01098278_m1" "Hs00996236_m1" "Hs00944507_g1" "Hs00372831_g1" "Hs00356958_m1" "Hs01051611_gH" "Hs00380101_m1" "Hs01076090_m1" "Hs00703025_s1" "Hs00251883_m1" "Hs01560931_m1" "Hs00171157_m1" "Hs00386692_m1" "Hs05016463_s1" "Hs00167524_m1" "Hs01089557_s1" "Hs00171042_m1" "Hs00745492_s1" "Hs00610058_m1" "Hs00884853_s1" "Hs00958111_m1" "Hs04189864_m1" "Hs00704853_s1" "Hs00543973_m1" "Hs00374264_g1" "Hs01087946_g1" "Hs00415546_m1" "Hs05036222_s1" "Hs00904817_m1" "Hs01072228_m1" |
| 40-19 | "Hs01072228_m1" "Hs00915710_m1" "Hs00174705_m1" "Hs00356958_m1" "Hs00174029_m1" "Hs00958111_m1" "Hs00248075_m1" "Hs01553775_g1" "Hs01098278_m1" "Hs00957562_m1" "Hs00937509_m1" "Hs00960591_m1" "Hs00747379_m1" "Hs00387770_m1" "Hs01547054_m1" "Hs00696959_m1" "Hs00399035_m1" "Hs00607978_s1" "Hs04942686_m1" "Hs00240906_m1" "Hs00962398_m1" "Hs00232157_m1" "Hs00267207_m1" "Hs00996236_m1" "Hs00704853_s1" "Hs00365956_m1" "Hs00196245_m1" "Hs00959010_m1" "Hs00884853_s1" "Hs01691258_g1" "Hs00950371_m1" "Hs00260480_m1" "Hs00174969_m1" "Hs01560931_m1" "Hs00964384_g1" "Hs00738791_g1" "Hs00543973_m1" "Hs00171042_m1" "Hs04189864_m1" "Hs00415546_m1" |
| 40-20 | "Hs00559914_m1" "Hs00856927_g1" "Hs00232157_m1" "Hs01029174_m1" "Hs00978280_m1" "Hs01051445_g1" "Hs01031740_m1" "Hs00899658_m1" "Hs00174705_m1" "Hs00153408_m1" "Hs00362096_m1" "Hs00944507_g1" "Hs00260452_m1" "Hs00937509_m1" "Hs00826827_g1" "Hs00248075_m1" "Hs01043717_m1" "Hs01070154_m1" "Hs01076090_m1" "Hs01560931_m1" "Hs01920599_gH" "Hs00543973_m1" "Hs00380101_m1" "Hs00997579_m1" "Hs03043789_g1" "Hs00901350_g1" "Hs03302824_pri" "Hs00399035_m1" "Hs00747379_m1" "Hs01114274_m1" "Hs04232205_s1" "Hs05016463_s1" "Hs00387770_m1" "Hs00366766_m1" "Hs04194422_s1" "Hs01008033_m1" "Hs01395177_m1" "Hs00904817_m1" "Hs03464469_s1" "Hs01894962_s1" |
| 40-21 | "Hs00826827_g1" "Hs00899658_m1" "Hs01076090_m1" "Hs00411188_g1" "Hs05036222_s1" "Hs00171042_m1" "Hs00926053_m1" "Hs00233987_m1" "Hs00174029_m1" "Hs00902334_m1" "Hs00958111_m1" "Hs00153408_m1" "Hs01081598_m1" "Hs01051445_g1" "Hs04189864_m1" "Hs00962398_m1" "Hs00155241_m1" "Hs00380101_m1" "Hs01560931_m1" "Hs00167524_m1" "Hs00171157_m1" "Hs00260480_m1" "Hs00174969_m1" "Hs01114274_m1" "Hs00705626_s1" "Hs01920599_gH" "Hs00428732_m1" "Hs01031740_m1" "Hs05016463_s1" "Hs01549976_m1" "Hs00931763_m1" "Hs00703025_s1" "Hs00960591_m1" "Hs05052601_s1" "Hs00937509_m1" "Hs01098278_m1" "Hs00968305_m1" "Hs01087946_g1" "Hs00959010_m1" "Hs01089557_s1" |
| 40-22 | "Hs00904817_m1" "Hs00260480_m1" "Hs00856927_g1" "Hs01894962_s1" "Hs00171042_m1" "Hs00171157_m1" "Hs01098278_m1" "Hs00202752_m1" "Hs01076090_m1" "Hs00964384_g1" "Hs00155241_m1" "Hs00950371_m1" "Hs01042796_m1" "Hs00826827_g1" "Hs00958111_m1" "Hs00899658_m1" "Hs00233987_m1" "Hs00926053_m1" "Hs01029174_m1" "Hs00174029_m1" "Hs01081598_m1" "Hs00159178_m1" "Hs00975850_m1" "Hs00232157_m1" "Hs00251883_m1" "Hs00372831_g1" "Hs00957562_m1" "Hs00610058_m1" "Hs01043717_m1" "Hs05033260_s1" "Hs01920599_gH" "Hs00543973_m1" "Hs01560931_m1" "Hs00901350_g1" "Hs00705626_s1" "Hs05016463_s1" "Hs00260452_m1" "Hs01553775_g1" "Hs00153408_m1" "Hs00962398_m1" |
| 40-23 | "Hs00801390_s1" "Hs00174969_m1" "Hs00959010_m1" "Hs00968305_m1" "Hs01547054_m1" "Hs01072228_m1" "Hs00262107_m1" "Hs01114274_m1" "Hs00937509_m1" "Hs01051611_gH" "Hs01920599_gH" "Hs01031740_m1" "Hs00399035_m1" "Hs00962398_m1" "Hs00233987_m1" "Hs00167524_m1" "Hs00826827_g1" "Hs01010736_m1" "Hs03302824_pri" "Hs01549976_m1" "Hs00901350_g1" "Hs00975850_m1" "Hs00904817_m1" "Hs00380101_m1" "Hs00387770_m1" "Hs04232205_s1" "Hs00240906_m1" "Hs00997579_m1" "Hs01560931_m1" "Hs01631495_s1" "Hs05052601_s1" "Hs00738791_g1" "Hs00171157_m1" "Hs00232157_m1" "Hs00978280_m1" "Hs00372831_g1" "Hs00704853_s1" "Hs00745492_s1" "Hs00936519_m1" "Hs00204257_m1" |
| 40-24 | "Hs01549976_m1" "Hs00260480_m1" "Hs01031740_m1" "Hs05052601_s1" "Hs05016463_s1" "Hs00196245_m1" "Hs01025572_m1" "Hs01042796_m1" "Hs00944507_g1" "Hs00171157_m1" "Hs00167524_m1" "Hs00962398_m1" "Hs00428732_m1" "Hs00543973_m1" "Hs01560931_m1" "Hs01087946_g1" "Hs00960591_m1" "Hs04189864_m1" "Hs00826827_g1" "Hs00380101_m1" "Hs01691258_g1" "Hs00386692_m1" "Hs00374264_g1" "Hs00745492_s1" "Hs00884853_s1" "Hs00411188_g1" "Hs00936519_m1" "Hs00240906_m1" "Hs00232157_m1" "Hs01098278_m1" "Hs03302824_pri" "Hs00248075_m1" "Hs00801390_s1" "Hs01553775_g1" "Hs03464469_s1" "Hs00738791_g1" "Hs01631495_s1" "Hs00703025_s1" "Hs00896999_g1" "Hs01010736_m1" |
| 40-25 | "Hs04189864_m1" "Hs00386692_m1" "Hs00926053_m1" "Hs00260452_m1" "Hs00610058_m1" "Hs00958111_m1" "Hs00704853_s1" "Hs00380101_m1" "Hs00543973_m1" "Hs00167524_m1" "Hs00747379_m1" "Hs00428732_m1" "Hs00559914_m1" "Hs00738791_g1" "Hs00260480_m1" "Hs00703025_s1" "Hs00975850_m1" "Hs01025572_m1" "Hs01098278_m1" "Hs01560931_m1" "Hs00745492_s1" "Hs00233987_m1" "Hs00232157_m1" "Hs05016463_s1" "Hs00607978_s1" "Hs00171042_m1" "Hs00884853_s1" "Hs01691258_g1" "Hs00196245_m1" "Hs01081598_m1" |

TABLE 13-continued

Exemplary gene sets used to predict risk of recurrence and/or metastasis

| Gene set | Probe identifiers used for each gene set (probe identifiers from ThermoFisher Scientific). |
|---|---|
| | "Hs00251883_m1" "Hs00904817_m1" "Hs01114274_m1" "Hs00222415_m1" "Hs01051445_g1" "Hs01042796_m1" "Hs00356958_m1" "Hs00944507_g1" "Hs00379134_m1" "Hs00705626_s1" |

See Table 11 for gene name associated with each probe ID.

Example 6: 40-GEP to Predict Metastatic Risk in Cutaneous SCC

Study Design—Development and Validation

Figure 5:
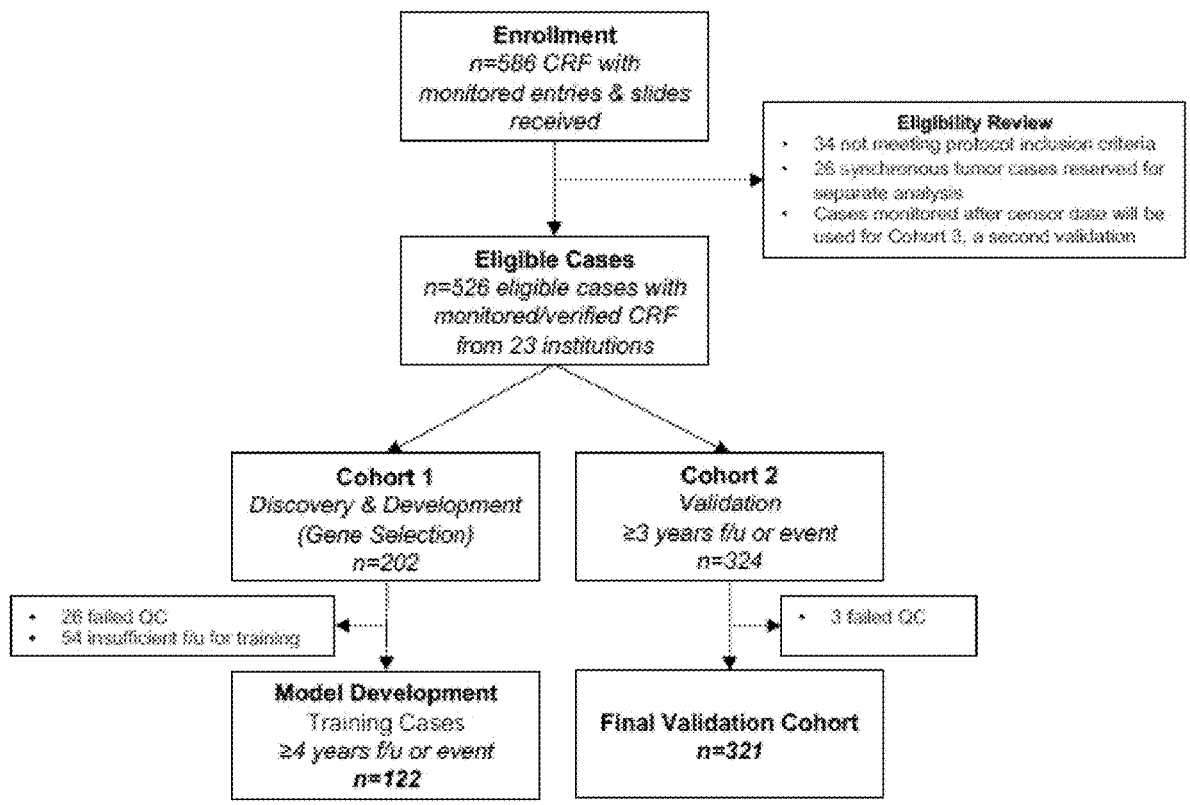
FIG. 5 shows the study cohorts: tissue samples and associated data acquisition. Abbreviations: CRF, case report form; f/u, follow up; event, regional or distant metastasis; QC, quality control.

To develop and validate a gene expression signature capable of stratifying patient risk of regional or distant metastasis, a prospectively-designed biomarker study was conducted on archival primary SCC formalin-fixed paraffin-embedded (FFPE) tissue (FIG. 5). The primary end point for this study was metastasis-free survival (MFS), including both regional and distant metastatic events. Regional metastasis was defined as a metastatic lesion within the regional nodal basin, including satellite or in-transit metastasis, but excluding local recurrence. Distant metastasis was defined as metastasis beyond the regional lymph node basin. Disease-specific death, a secondary end point, was defined as death from SCC documented in patient medical records.

Expression of 140 candidate genes was determined for all samples in the discovery and development cases (cohort 1, n=202). Deep learning was applied to expression data from 122 genes passing initial expression thresholds to select genes for further signature training. The prognostic algorithm encompassing the 40-GEP assay was selected based on performance in training and gene coefficients were locked prior to validation. Power calculations indicated that the validation cohort (cohort 2, n=321) could detect a hazard ratio of 2.1 for metastasis with 90% power, alpha=0.05. After validation of the algorithm using cohort 2, clinically-actionable cut-points for probability scores from the models were set to optimize negative predictive value (NPV), positive predictive value (PPV), and sensitivity for metastasis-risk groups (Class 1: low risk; Class 2A: high/moderate risk; Class 2B: highest risk).

Detailed Study Design—Discovery and Development

For model training (cohort 1, training set), probes were filtered based on the consistency of expression across preliminary runs across 140 probes. The initial set of probes was filtered for amplification and stability of gene expression, resulting in 122 discriminant probes and 6 control probes (MDM2 (Hs00540450_s1), KMT2D (Hs00912419_m1), BAG6 (Hs00190383_m1), FXR1 (Hs01096876_g1), MDM4 (Hs00967238_m1), and KMT2C (Hs01005521_m1). Cases were filtered based on detectable expression of at least 90% of the candidate discriminant probes. Deep learning techniques were applied to gene expression data from cohort 1 for gene selection and model identification. To ensure proper classification, the training set was restricted to cases with a documented metastatic event or at least 4 years of follow up. Gene expression using 140 candidate probes identified by literature review or through preliminary discovery efforts was determined for all samples in cohort 1. Triplicate gene expression data were aggregated and normalized using the control probes identified from the larger case set. Genetic algorithms combined with neural network models were used to generate two independent prediction algorithms from the 122 cases and 122 predictive probes passing initial expression thresholds. Genetic algorithms optimized neural network predictive algorithms across a range of target gene set sizes. Initial models were generated by training neural network models to a set of 100 randomly generated gene lists from the set of 122 without replacement. At each iteration of the genetic algorithm, the top 25% of models were retained and their gene lists mated by randomly selecting approximately 45% of the genes from each list, removing duplicates, and then filling the list to the target size by selecting genes from the remaining 122 gene set. This process provided a minimum 10% mutation rate at each iteration. Genetic improvement continued until the mean kappa value for the population improved by less than 0.01. Neural network hyperparameters were optimized using a training control of 10 times 4-fold repeated cross validation with hyperparameter selection based on the maximum kappa value. The final model was trained against all training data using the optimal hyperparameter set. Two models were developed, one using no weighting, and another weighting metastasis as twice that of nonmetastasis, which together generated the locked algorithm for the 40-GEP test.

Patient Enrollment, Specimen Acquisition, and Cohort Definitions

Archived FFPE primary cutaneous SCC tissue and associated de-identified clinical data were obtained from 23 independent centers following Institutional Review Board (IRB) approval. Associated clinical, pathological, and outcomes data were entered onto a secure case report form (CRF) and on-site data monitoring was performed for all cases. As part of the ongoing study protocol, 586 archival SCC cases with complete CRFs and FFPE tissue were received. The workflow diagram in FIG. 5 summarizes protocol inclusion/exclusion criteria. Briefly, inclusion criteria specified pathologically confirmed cutaneous SCC with available FFPE tissue from either the original biopsy or the definitive surgical excision. Subjects had a documented regional or distant metastasis, or a minimum of three years of clinical follow-up without evidence of metastasis. The protocol targeted enrollment of cases for the intent-to-treat patient population. The protocol targeted enrollment of with at least one high-risk feature as defined by guidelines or staging systems (features considered high-risk for targeted enrollment include, but are not limited to, any single clinicopathological feature by which a patient could be deemed NCCN-high risk or increase a patient's T-stage above T1), either at the patient or tumor level, to best model the intent-to-treat patient population. Centralized pathology review of a representative hematoxylin and eosin (H&E) stained tissue section was performed by a board-certified dermatopathologist to confirm diagnosis of SCC and assess for high-risk features. Per study design, the first ~200 cases received and monitored were selected for discovery and development (cohort 1 n=202) and the remaining cases for validation (cohort 2 n=324).

All CRFs were monitored, which included review of all available pathology reports and medical records associated with received lesions. For cohort 2, monitors reviewed 98.4% (314/319) of all pathology reports from definitive surgeries. Two cases did not receive definitive surgery. All cases were categorized as NCCN low or high risk and were restaged by AJCC 8th Edition and BWH criteria per features listed in the original pathology reports, available medical records, and independent dermatopathologist review. Consistent with College of American Pathology (CAP) reporting protocols, histopathological features not reported or not identified were considered negative for staging and analysis.

Assay Methods

FFPE tissue sections were freshly cut to 5 μm sections at the contributing institution and collected at a central CAP-accredited laboratory. Tumor tissue was macrodissected from slides, including tumor stroma and infiltrating immune cells, and processed to generate RNA and cDNA.

Each cDNA sample underwent a 14-cycle preamplification step prior to dilution, and then was mixed 1:1 with 2× TaqMan Gene Expression Master Mix. Quantitative polymerase chain reaction (qPCR) was then performed using high-throughput microfluidics gene cards containing primers specific to the genes of interest and the QuantStudio 12K Flex Real-Time PCR System (Life Technologies). Each sample was run in triplicate with samples randomized onto plates to distribute metastatic and nonmetastatic cases. Laboratory personnel and clinical monitoring staff were blinded to GEP results during data capture.

Statistical Analysis

Survival analyses using the Kaplan-Meier method were performed in R (version 2.44) with survival statistics calculated using either the log-rank test or multivariate Cox regression analysis when appropriate. For Cox regression, analysis assumptions of proportional hazards were confirmed using the zph test of the fitted model. In cases where proportional hazards assumptions were violated in Cox regression models, additional multivariate survival regression models were used to confirm the results. Binned 40-GEP results and risk according to established staging methods were included in regression models. Accuracy metrics were assessed for GEP Classes, both Class 2A and 2B as the high-risk group for completeness, and clinical risk staging parameters using functions in the caret package (version 6.0) in R (version 3.6.1).

Results

Development of the Prognostic Signature

To identify a prognostic signature capable of patient stratification by risk of regional or distant metastasis from primary SCC tumors, deep learning was applied to gene expression data from training cohort (n=122, 13 metastatic cases). Demographics of the training cohort are shown in FIG. 12. The algorithm selected for validation was comprised of two gene expression signatures, inclusive of 6 control and 34 discriminant genes in total, with risk modeling performed using neural networks. This 40-GEP algorithm generated linear scores for probability of metastasis from each predictive signature.

Independent Validation Cohort Demographics

The validation cohort of 321 primary SCC cases was comprised of 52 cases (16%) with documented metastasis, and 269 cases without a metastatic event. Baseline cohort characteristics are summarized in FIG. 7. Most of the patients were Caucasian (99.7%), non-Hispanic (97.2%), male (73.2%), and immunocompetent (76.3%) with tumors located on the head and neck (66.7%), consistent with typical SCC presentation. According to NCCN Guidelines® criteria, 93% were high risk. The surgical treatment modalities were Mohs surgery (79.8%) and wide local excision (19.6%). The following clinicopathologic features were statistically different between metastatic and nonmetastatic cases in univariate analysis: tumor differentiation, perineural invasion, invasion into subcutaneous fat, tumor thickness, tumor diameter, lymphovascular invasion, tumor located on head/neck, definitive surgery as Mohs micrographic surgery, Clark level, and patient sex.

Independent Validation of the 40-GEP Prognostic Signature

To validate the prognostic capability of the 40-GEP, the algorithm was applied to independent cohort 2. The algorithm demonstrated a statistically significant ability to stratify metastatic risk. The validated 40-GEP was then used to define risk groups with increasing metastasis risk: Class 1 (low risk, n=203), Class 2A (high risk, n=93), and Class 2B (highest risk, n=25). Significantly different 3-year MFS rates were observed for Class 1 (91.6%), Class 2A (80.6%), and Class 2B (44.0%) groups following Kaplan-Meier survival analysis (FIG. 6, log-rank test, p<0.0001). The overall rates of metastasis in each Class were 8.9%, 20.4%, and 60.0%, respectively. The final gene signature identified 64% (34 of 52) of the cases having metastasis as Class 2, with 15 cases identified as Class 2B. The 40-GEP Class was associated with disease-specific death resulting in a hazard ratio of 5.4 and 8.8 for Class 2A and Class 2B, respectively (univariate model; p<0.05, p<0.01). Of the 13 reported deaths due to SCC, 10 were classified as Class 2 (7 Class 2A and 3 Class 2B).

Prognostic Accuracy of the 40-GEP Test Compared to Staging Systems

The 40-GEP signature was an independent predictor of risk when analyzed in a multivariate model with AJCC (Class 2A HR=2.17, p=0.019; Class 2B HR=9.34, p<0.0001) or BWH (Class 2A HR=2.23, p=0.016; Class 2B HR=8.68, p<0.0001) staging systems (see FIG. 8 and FIG. 11). Multivariate analysis with individual clinicopathological features also demonstrates that the 40-GEP signature demonstrates independent prognostic value over these features (see FIG. 13). FIG. 9 reports the number of cases with or without metastasis in the validation cohort according to 40-GEP Class and with respect to NCCN risk group or T-stage.

Overall, accuracy metrics for AJCC (T1/T2 vs. T3/T4) and BWH staging (T1/T2a vs. T2b/T3) align with previously published data (FIG. 10; see Ruiz et al., JAMA Dermatol. 155: 819 (2019); Karia et al., JAMA Dermatol. 154: 175 (2018); Jambusaria-Pahlajani et al., JAMA Dermatol. 149: 402 (2013); and Karia et al., KO 32: 327-334 (2014)). The 40-GEP Class 2B group demonstrated a PPV of 60% compared to 16.7%, 22.0%, and 35.6% for NCCN, AJCC, and BWH high-risk groups, respectively (see FIG. 10). The Class 1 group was associated with a 91.1% NPV, exceeding the 87.6% and 87.0% NPV for AJCC and BWH staging, respectively, and matching the 90.5% NPV of NCCN. Importantly, 63% of the validation cohort overall and 67% of the high-risk NCCN cases were identified as low risk Class 1 by the 40-GEP with the highest NPV relative to NCCN, AJCC, and BWH.

TABLE 14

Discriminant genes (n = 34) included in the prognostic signature.

| GENE ID | GENE NAME |
| --- | --- |
| ACSBG1 | Long-chain-fatty-acid-CoA ligase ACSBG1 |
| ALOX12 | Arachidonate 12-Lipoxygenase, 12S Type |
| APOBEC3G | Apolipoprotein B MRNA Editing Enzyme Catalytic Subunit 3G |
| ATP6V0E2 | ATPase H+ Transporting V0 Subunit E2 |
| BBC3 | Bcl-2-binding component 3 |
| BHLHB9 | Basic Helix-Loop-Helix Family Member B9 |
| CEP76 | Centrosomal protein of 76 kDa |
| DUXAP8 | Double Homeobox A Pseudogene 8 |
| GTPBP2 | GTP Binding Protein 2 |

TABLE 14-continued

Discriminant genes (n = 34) included in the prognostic signature.

| GENE ID | GENE NAME |
|---|---|
| HDDC3 | Guanosine-3',5'-bis(diphosphate) 3'-pyrophosphohydrolase MESH1 |
| ID2 | Inhibitor Of DNA Binding 2 |
| LCE2B | Late Cornified Envelope 2B |
| LIME1 (ZGPAT) | Lck Interacting Transmembrane Adaptor 1 |
| LOC100287896 | Uncharacterized LOC100287896 |
| LOC101927502 | Uncharacterized LOC101927502 |
| MMP10 | Matrix Metalloproteinase 10 (Stromelysin 2) |
| MRC1 | Mannose Receptor C-Type 1 |
| MSANTD4 | Myb/SANT DNA Binding Domain Containing 4 With Coiled-Coils |
| NFASC | Neurofascin |
| NFIC | Nuclear Factor I C |
| PDPN | Podoplanin |
| PI3 | Peptidase Inhibitor 3 |
| PLS3 | Plastin 3 |
| RCHY1 | Ring Finger And CHY Zinc Finger Domain Containing 1 |
| RNF135 | Ring Finger Protein 135 |
| RPP38 | Ribonuclease P/MRP Subunit P38 |
| RUNX3 | Runt-Related Transcription Factor 3 |
| SLC1A3 | Solute Carrier Family 1 Member 3 |
| SPP1 | Osteopontin |
| TAF6L | TATA-Box Binding Protein Associated Factor 6 Like |
| TFAP2B | Transcription Factor AP-2 Beta |
| ZNF48 | Zinc Finger Protein 48 |
| ZNF496 | Zinc Finger Protein 496 |
| ZNF839 | Zinc Finger Protein 839 |

TABLE 15

34 discriminant genes included in GEP gene set able to predict risk of recurrence and/or metastasis

| Gene name | Probe Identifier (ThermoFisher) | Change in gene expression in recurrent cancer when compared to non-recurrent cancer. |
|---|---|---|
| ACSBG1 | Hs01025572_m1 | decrease |
| ALOX12 | Hs00167524_m1 | decrease |
| APOBEC3G | Hs00222415_m1 | increase |
| ATP6V0E2 | Hs04189864_m1 | increase |
| BBC3 | Hs00248075_m1 | increase |
| BHLHB9 | Hs01089557_s1 | decrease |
| CEP76 | Hs00950371_m1 | decrease |
| DUXAP8 | Hs04942686_m1 | increase |
| GTPBP2 | Hs01051445_g1 | decrease |
| HDDC3 | Hs00826827_g1 | increase |
| ID2 | Hs00747379_m1 | decrease |
| LCE2B | Hs04194422_s1 | decrease |
| LIME1 (ZGPAT) | Hs00738791_g1 | increase |
| LOC101927502 | Hs05033260_s1 | increase |
| LOC100287896 | Hs01931732_s1 | increase |
| MMP10 | Hs00233987_m1 | decrease |
| MRC1 | Hs00267207_m1 | decrease |
| MSANTD4 | Hs00411188_g1 | decrease |
| NFASC | Hs00978280_m1 | decrease |
| NFIC | Hs00232157_m1 | decrease |
| PDPN | Hs00366766_m1 | decrease |
| PI3 | Hs00964384_g1 | decrease |
| PLS3 | Hs00543973_m1 | decrease |
| RCHY1 | Hs00996236_m1 | increase |
| RNF135 | Hs00260480_m1 | increase |
| RPP38 | Hs00705626_s1 | decrease |
| RUNX3 | Hs00231709_m1 | increase |
| SLC1A3 | Hs00904817_m1 | increase |
| SPP1 | Hs00959010_m1 | increase |
| TAF6L | Hs01008033_m1 | increase |
| TFAP2B | Hs01560931_m1 | decrease |
| ZNF48 | Hs00399035_m1 | increase |
| ZNF496 | Hs00262107_m1 | increase |
| ZNF839 | Hs00901350_g1 | increase |

Control genes: MDM2 (Hs00540450_s1), KMT2D (Hs00912419_m1), BAG6 (Hs00190383_m1), FXR1 (Hs01096876_g1), MDM4 (Hs00967238_m1), and KMT2C (Hs01005521_m1).

Example 7: Integrating Gene Expression Profiling into NCCN High-Risk Cutaneous Squamous Cell Carcinoma Management Recommendations: Impact on Patient Management and Outcomes Cutaneous squamous cell carcinoma (cSCC) is the second most common form of skin cancer after basal cell carcinoma. It occurs in approximately one million people in the U.S. and the incidence is rising, partly due to enhanced detection methods and an aging population. Overall, approximately 6% of cSCC patients develop regional or distant metastatic lesions and survival rates are low for those who do develop metastasis. The number of deaths from cSCC, a large proportion of which are preceded by metastasis, has been estimated to rival that from melanoma. Therefore, accurate prediction of risk for metastasis is essential for optimal patient management and improving outcomes.

National Comprehensive Cancer Network (NCCN) Guidelines® outline broad approaches for management of cSCC patients considered high risk for developing recurrence and/or metastasis. Risk stratification and staging systems for cSCC include NCCN Guidelines Criteria®, the American Joint Committee on Cancer (AJCC) Cancer Staging Manual (8th Edition), and the Brigham and Women's Hospital (BWH) tumor classification system. These systems are based on clinical and pathological features; however, they are specifically limited in their ability to predict adverse outcomes (i.e., have low positive predictive value (PPV) for metastasis) and pose a challenge to implementing risk-directed patient management. Patients with cSCC would benefit from improved prognostic tools for determining which patients currently considered clinicopathologically "high risk" are truly at low risk, which patients should consider procedures to detect nodal/distant disease (e.g., node biopsy versus imaging versus clinical examination only), and which should consider therapeutic intervention to reduce risk for recurrence/metastasis (e.g., adjuvant radiation, chemotherapy, additional surgery, and clinical trial enrollment). Given that risk classifications guide treatment plans, improved prognostic tools would enhance shared decision-making between physicians and their patients. Ultimately, the goal is early intervention for individuals who are likely to develop metastasis and avoidance of unnecessary invasive or costly procedures for those who are at lower risk for developing metastasis.

The 40-gene expression profile (40-GEP) test using archival, formalin-fixed paraffin-embedded (FFPE), primary cSCC tissue as disclosed herein stratifies clinicopathologically identified high-risk cSCC tumors into three risk groups based on low (Class 1), high (Class 2A), and highest (Class 2B) risk for regional or distant metastasis at 3 years after diagnosis. A substantially higher PPV (60.0%) was found for the 40-GEP test for Class 2B relative to that found for the AJCC (22.0%) and BWH (35.6%) staging systems, while maintaining a negative predictive value (NPV) of approximately 90.0% (which is similar to that of the AJCC and BWH systems). The primary goal of developing and validating the 40-GEP test was to improve metastasis risk prediction.

Applying the 40-GEP test to risk-directed management recommendations from the NCCN Guidelines® for 300 NCCN-defined high-risk cSCC cases of the 40-GEP clinical validation cohort demonstrated that integration of a molecular prognostic tool with higher PPV, and similar NPV, relative to current staging systems can identify a subgroup (40-GEP Class 1 and low-risk T stage) of NCCN-defined high-risk patients with rates of metastasis similar to those in the clinicopathologic low-risk group, suggesting this subgroup could be managed less aggressively. By comparison, integration of the 40-GEP test also suggested that a patient with a Class 2B tumor with a high risk for metastasis would warrant intensified intervention, thereby achieving risk-appropriate allocation of surgical, imaging, and therapeutic resources. In all, integrating the 40-GEP test into risk-directed guidelines for patient management resulted in more personalized treatment recommendations and potential improvement of net health outcomes. This was accomplished by identifying both a low-risk subgroup (more than 50% of the cohort) that could be managed conservatively (low intensity management) and a smaller subgroup (8%) of patients who were at higher risk for metastasis and would require more aggressive intervention (high intensity management).

Materials and Methods

Integration of 40-GEP within High-Risk NCCN Patient Management Guidelines

For NCCN-defined high-risk patients from the 40-GEP clinical validation cohort, metastasis risk Class (40-GEP results), T stage, and known patient outcomes were extracted. This high-risk cohort (n=300) included only cases meeting study criteria and having one or more NCCN-defined high-risk feature, as noted in FIG. 16. Briefly, criteria for study inclusion were pathologically-confirmed cSCC diagnosed after Jan. 1, 2006; available archival, FFPE primary cSCC tumor tissue; complete case report forms; and documented metastasis or minimum follow-up period of 3 years without metastasis. Study cohort demographics and clinical characteristics were monitored and underwent centralized pathology review (FIG. 16).

Data Analysis and Risk-Aligned Management Recommendations

For the NCCN high-risk cohort (n=300), the cases stratified in each 40-GEP Class, along with corresponding metastasis rates and T stage, were analyzed to align each patient group (40-GEP Class/T stage) with risk-appropriate management recommendations. Within the framework of NCCN Guidelines® for management of high-risk cSCC patients with localized disease, risk-aligned management recommendations based on 40-GEP results and T stage were developed for low, moderate, and high intensity management to correspond with metastasis risk bins of <10%, 10-50%, and >50% risk, respectively. Risk-aligned management recommendations addressed follow-up, imaging, nodal assessment, adjuvant therapy, and clinical trials.

Results

Cohort Characteristics, 40-GEP Risk Classification, and Outcomes

A 300-case cohort of NCCN high-risk cSCC patients (FIG. 16) was used to integrate a recently validated 40-GEP test into NCCN Guidelines® and T stage criteria for patient management to develop risk-aligned management recommendations. The 40-GEP test classifies patients into three risk groups: Class 1, Class 2A, and Class 2B, having low, high, and highest risk for metastasis at 3 years post-diagnosis, respectively. Of the 300 cases, 189 (63.0%) were Class 1, 87 (29.0%) were Class 2A, and 24 (8.0%) were Class 2B with overall metastasis rates of 9%, 21%, and 63%, respectively (see FIG. 14A). More than 50% of the cases were Class 1 and AJCC T1-T2 (n=159, 53.0%) or BWH T1-T2a (n=173, 57.7%) with metastasis rates below 10% (AJCC, 7.5%; BWH, 8.1%) (see FIGS. 14A and 14B). Whereas, Class 1 cases that were also AJCC T3-T4 or BWH T2b-T3, as well as all Class 2A cases, had metastasis rates above 10%, but lower than 50%. All Class 2B cases (8.0% of the cohort) had metastasis rates that were greater than 50%.

Clinical Utility of Integrating the 40-GEP Test

Figure 15:
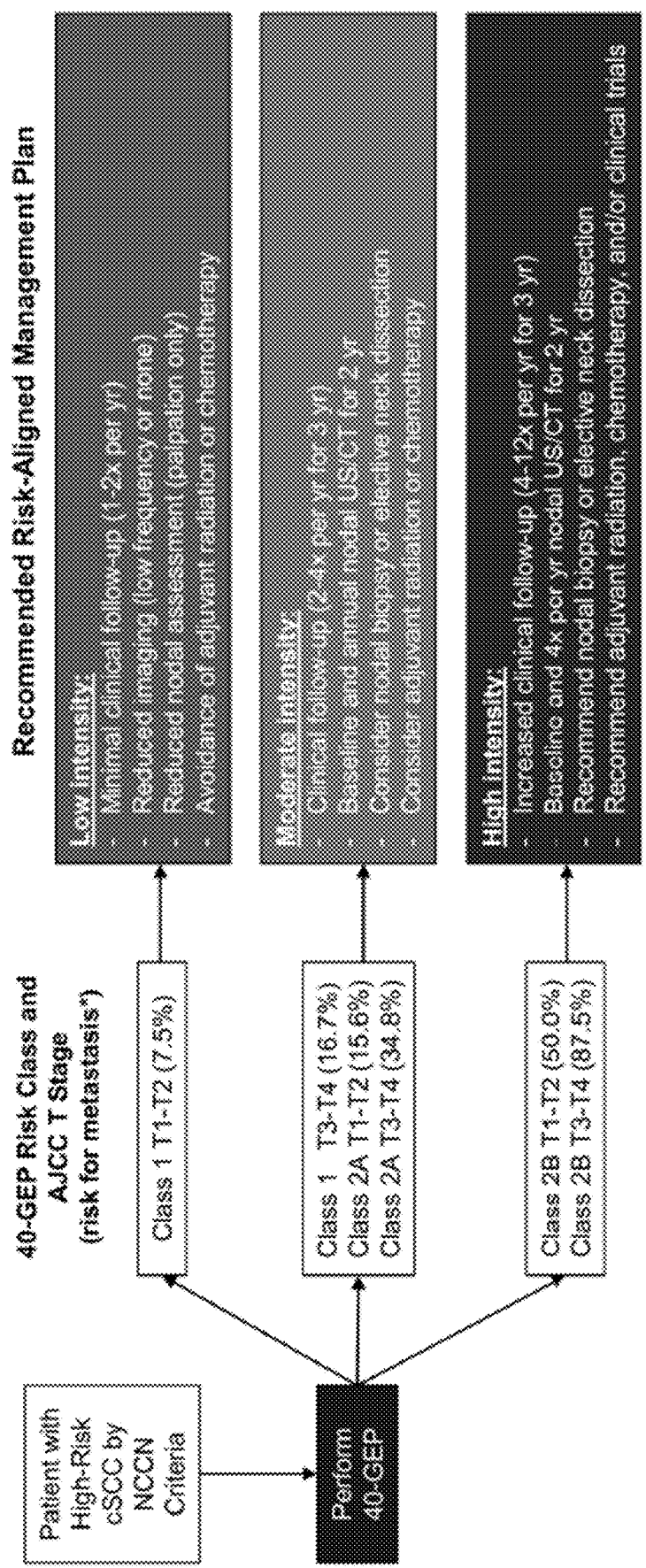
FIG. 15 shows an exemplary recommended risk-aligned cSCC patient management for prognostic groups based on 40-GEP and T stage. *Risk for metastasis is reported for 40-GEP Class and AJCC T stage.

By combining the low-risk Class 1 result with AJCC T1-T2 stage, a 3-year metastasis rate of 7.5% (NPV, 92.5%) was identified for this subgroup (see FIGS. 14 and 15). This metastasis rate for this subgroup within the NCCN high-risk cohort is approaching the rate reported for the general cSCC patient population (<6% metastasis). Of the Class 1 cases, 159 and 173 were AJCC T1-T2 and BWH T1-T2a, respectively, and were risk-aligned for receiving low intensity management (see FIGS. 14A and 14B). The 40-GEP identified a highest-risk (Class 2B) subpopulation (n=24, 8.0%) which was risk-aligned for receiving high intensity management, consisting of 16 and 8 patients who were AJCC T1-T2 and T3-T4, respectively, and 17 and 7 who were BWH T1-2a and T2b-T3, respectively. Of the remainder of the cohort, 64 were Class 2A/AJCC T1-T2 and 73 were Class 2A/BWH T1-T2a, with a risk for metastasis of 15.6% and 17.8%, respectively (FIG. 14A). These rates are lower than that for the overall cohort, but still more than twice that of the general cSCC patient population. Moderate intensity management was suggested for this group, as well as those patients who were Class 1 or 2A and AJCC T3-T4 or BWH T2b-T3 (see FIGS. 14A and 14B).

The 40-GEP test results, when adjusted for AJCC or BWH T stage in this study, suggest low management intensity for 53.0% or 57.7% of the 300-patient cohort, respectively (FIG. 14). As shown in FIG. 15, low intensity management for these types of Class 1 patients could involve low frequency follow-up visits (1-2 visits/year), low frequency or no imaging, and less intense or no nodal assessments (ultrasound (US) scans versus computed tomography (CT) or nodal palpation in lieu of US or CT). Integration of the 40-GEP test suggests moderate intensity for 39.0% (40-GEP+AJCC) or 34.3% (40-GEP+BWH) of the cohort, and high intensity patient management for 8.0% (FIG. 14). Moderate intensity management could allow for fewer follow-up visits relative to high intensity management (2-4 versus 4-12 visits/year for 3 years), fewer invasive procedures (fewer biopsies and lymph node dissections), and more sparing use of systemic and adjuvant therapy (immunotherapy, chemotherapy, or adjuvant radiation therapy) (FIG. 15). For those patients for whom these risk-aligned recommendations suggest high intensity management, more intensified surveillance and treatment modalities as shown in FIG. 15 would be risk-appropriate.

The 40-GEP test results for a cohort of 300 NCCN-defined high-risk patients were combined with T stage, and risk-aligned recommendations for patient management intensity were developed within the NCCN Guidelines® framework. This integration demonstrates the validated 40-GEP prognostic test has clinical utility for complementing current staging systems and national patient guidelines to refine management pathways for cSCC patients deemed high risk by clinicopathologic methods. The 40-GEP test provides more accurate prediction of risk for metastasis in NCCN-defined high-risk cSCC patients, enabling improved risk-directed management decisions for therapy and surveillance. The current study reports the value of the test to identify within an NCCN high-risk cSCC patient population: 1) low-risk patients, having metastasis rates similar to rates of the general cSCC patient population, and who could benefit from low intensity management; and 2) truly high-risk patients who may benefit from high intensity management. The value of more accurate prognosis would be an improvement in health outcomes through the delivery of risk-appropriate management. Collectively, the 40-GEP test provides independent probability for risk of metastasis that, in combination with AJCC or BWH T stage, could improve risk-directed management in patients diagnosed with NCCN-defined high-risk cSCC. In summary, integration of the 40-GEP test into management of high-risk cSCC could enable net health outcome improvements for the majority of patients tested. The 40-GEP test can be integrated within NCCN guideline recommendations and, in combination with T stage, may have clinical utility for impacting patient management decisions and outcomes.

Example 8: Incorporation of the 40-Gene Expression Profile Test into Clinicopathological Risk Factor Assessment for Metastasis Prediction in High-Risk Cutaneous Squamous Cell Carcinoma An estimated 2-6% of cutaneous squamous cell carcinoma (cSCC) patients develop regional or distant metastasis, and approximately 2% die from the disease annually in the U.S. Although the fatality rate is low, the incidence of cSCC is high and continues to grow (estimated at 1-2.5 million cases/year), resulting in a substantial number of patients with poor outcomes. As the distribution of nonmelanoma skin cancer is shifting from a historical 1:4 towards a 1:1 ratio for cSCC to basal cell carcinoma, the estimated mortality rate for cSCC is similar to and will likely surpass that for melanoma.

Development of metastatic disease has a profound impact on cSCC patient survival, underscoring the need for effective identification of patients at risk for metastasis. While the 5-year disease-specific survival rate is >90% for localized disease, those rates drop to 50-83% and below 40% for patients with regional and distant metastases, respectively. Thus, accurate identification of which cSCC tumors have higher metastatic potential is essential for optimizing management decisions, particularly given the effective interventions that are available for cSCC treatment.

Patients with cSCC are broadly classified as having high-risk disease based on clinicopathologic factors associated with increased risk for recurrence and/or metastasis. For example, tumors with diameter>2 cm have been reported to have 2- and 3-fold greater risk for recurrence and metastasis, respectively, relative to smaller tumors. Likewise, tumors invading beyond subcutaneous fat and those with perineural invasion (PNI) of large caliber nerves or poor histologic differentiation have been linked to a 2- to 23-fold increased risk for recurrence and metastasis in univariate analyses. At the patient level, immunosuppressed individuals are at greater risk for developing cSCC and often present with more aggressive cSCC tumors. While these and other factors are used to stratify patient risk, low accuracy, histopathologic discordance, and lack of reporting standardization limit clinical utility of this approach. Standardized methods for cSCC risk assessment are not universally adopted and continue to be refined. The National Comprehensive Cancer Network (NCCN) categorizes a patient as high risk for recurrence and/or metastasis by the presence of a single NCCN-defined high-risk factor, and provides a broad range of management guidelines based on this assessment. Current tumor staging systems, such as the American Joint Committee on Cancer (AJCC) Cancer Staging Manual, $8^{th}$ Edition (AJCC8), and Brigham and Women's Hospital (BWH) system, help determine recurrence and metastatic risk by incorporation of high-risk factors into tumor (T) stages. While all systems utilize clinicopathologic factors of the primary tumor to categorize risk, their clinical utility is limited, primarily by low positive predictive values (PPV), leading to overestimation of the number of patients at risk for metastasis. Due to these clinical limitations, physicians often rely on professional experience and institution-specific approaches to drive treatment decisions. Despite attempts to improve and implement risk assessment, a standardized and accurate stratification system remains a clinically unmet need in the care of cSCC patients.

The above Examples demonstrate validation of a gene expression profiling-based algorithm (40-GEP; see Table 15) that accurately identifies cSCC tumor risk for metastasis by classifying patients into three groups: Class 1 (low risk), Class 2A (moderate risk), and Class 2B (high risk). In an archival cohort of 321 cSCC patients, the Class 2B group demonstrated a PPV of 60% compared to 33%, 35%, and 17% for AJCC8, BWH, and NCCN systems, respectively. Observed 3-year metastasis-free survival (MFS) rates were 92%, 81%, and 44% for Class 1, Class 2A, and Class 2B patients, respectively; and those having a Class 2B or Class 2A result had a significantly higher hazard ratios (HR) relative to Class 1 patients in multivariate analysis with either AJCC8 or BWH binary T stages, indicating independent prognostic value. The demonstrated accuracy of the 40-GEP test for predicting risk for metastasis in patients with high-risk cSCC is based on tumor-intrinsic factors alone, and improved prognostic value relative to current staging systems.

This Example demonstrates the clinical validity of the 40-GEP test when incorporated into routine clinicopathologic factor-based cSCC risk assessment. In an expanded cohort of cSCC patients (n=420) with high-risk factors, this Example shows independent prognostic value of the 40-GEP test performed using clinical laboratory-developed standard operating procedures (SOPs). Combining novel molecular prognostication with clinicopathologic risk assessment demonstrated improved risk stratification, which can facilitate risk-appropriate management decisions for high-risk cSCC patients.

Methods

Study Cohort

Figure 17:
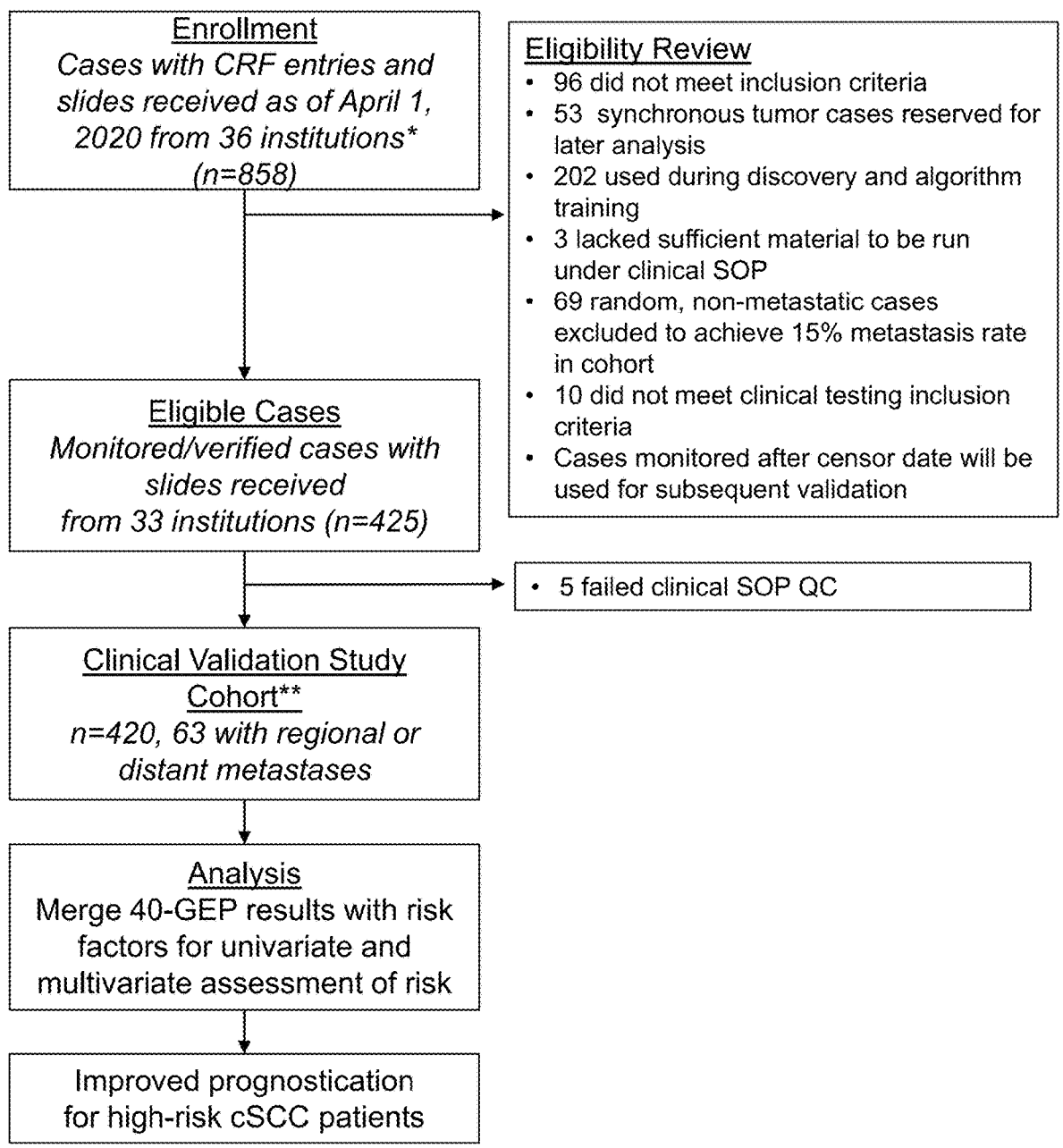
FIG. 17 shows the study design and cohort (n=420). Clinicopathologic and outcomes data were collected from 33 institutions from Sep. 3, 2016 to Apr. 1, 2020.

Using an ongoing, institutional review board-approved protocol, formalin-fixed paraffin-embedded (FFPE) samples from primary cSCC lesions and corresponding clinicopathologic and outcomes data were collected from 33 institutions from Sep. 3, 2016 to Apr. 1, 2020 (FIG. 17). All cases underwent review of biopsy and definitive surgery reports, and medical records. Tested tissue was independently reviewed by a board-certified dermatopathologist for tumor content and high-risk factors. Clinicopathologic factors were deemed positive/present if identified during any review step.

All cases (307 previously-run and 113 new) were either high-risk by NCCN guidelines for localized cSCC or met Mohs Micrographic Surgery (MMS) appropriate use criteria (AUC). Methods of individual case risk factor assessment are noted in Table 16. The seven risk factors assessed include: tumor size and location, immune status, PNI, depth of invasion, differentiation, histological subtype, and lymphovascular invasion. For cases with metastases, all samples received and monitored during the time period were included. Random samples from non-metastatic cases were included to align with a ~15% overall metastasis rate, which corresponds with previously published metastasis rates in high-risk cSCC (FIG. 17).

TABLE 16

Risk factors captured and used for factor count by case

| Risk Factors | Factor Count |
|---|---|
| Tumor size and location* | 1 |
| Any size on the head, neck, genitalia, hands, feet or pretibial surface (Areas H or M), or | |
| ≥2 cm size (or ≥1 cm if keratoacanthoma type) on any other area of the body (Area L) | |
| Immunosuppressed** | 1 |
| Perineural involvement: Large (≥0.1 mm), named nerve involvement, <0.1 mm in caliber, or unknown | 1 |
| Depth (any one or combination of) | 1 |
| Invasion beyond subcutaneous fat | |
| Depth ≥ 2 mm | |
| Clark level ≥ IV | |
| Poorly differentiated tumor histology | 1 |
| Aggressive histologic subtypes*** | 1 |
| Lymphovascular invasion | 1 |
| TOTAL POSSIBLE COUNTS# | 7 |

*Location definitions per National Comprehensive Cancer Network (NCCN) Guidelines: Area H, 'mask areas' of face (central face, eyelids, eyebrows, periorbital, nose, lips [cutaneous and vermillion], chin, mandible, preauricular and postauricular skin/sulci, temple, and ear); genitalia, hands, and feet; Area M, cheeks, forehead, scalp, neck, and pretibia; and Area L, trunk and extremities (excluding hands, nail units, pretibial, ankles, and feet).
**Types of immunosuppression included per protocol were from organ transplant, leukemia, lymphoma, HIV.
***Any of: Acantholytic, adenosquamous, desmoplastic, sclerosing, basosquamous, small cell, spindle cell, infiltrating, clear cell, lymphoepithelial, sarcomatoid, or metaplastic subtypes.
Note,
tumors with poorly defined borders, that were rapidly growing, with neurologic symptoms in tumor region, and/or at a site of prior radiation therapy or chronic inflammatory process were not captured by this current study but will be allowed for clinical testing as defined as high risk per NCCN.

Gene Expression Analysis

All samples were assayed under clinical SOPs in a central College of American Pathologists-accredited laboratory with personnel blinded to patient outcomes. Briefly, FFPE primary cSCC tumor tissue was macrodissected, processed for real-time PCR, and assayed in triplicate. Duplicate sample runs were used to generate clinical 40-GEP Class scores.

Statistics

Statistical analyses were performed in R (v3.6.3). Survival analyses were performed using Kaplan-Meier methods and log-rank test. Univariate and multivariate Cox regression analyses were performed using standard methods.

Results

Risk Assessment by Molecular Prognostication Alone

To validate the 40-GEP algorithm for use in the clinical setting, FFPE samples from 436 primary cSCC tumors were assessed using the 40-GEP algorithm disclosed herein and validated clinical SOPs. Six samples failed amplification at predetermined operating thresholds and 10 cases did not meet testing criteria of one high-risk factor, leaving 420 samples for final clinical validation (cohort characteristics, Table 17). The cohort included 63 cases with regional and/or distant metastases and 357 without an event within ≥3 years of follow-up. Median time-to-metastasis was 0.9 years ($95^{th}$ percentile: 2.7 years). The following clinicopathologic characteristics had significantly different rates for non-metastatic versus metastatic cases: male sex, location on the head and neck, tumor diameter, tumor thickness, poor differentiation, PNI, invasion beyond subcutaneous fat, and cases undergoing MMS (p<0.03; Table 17).

Figure 18A:
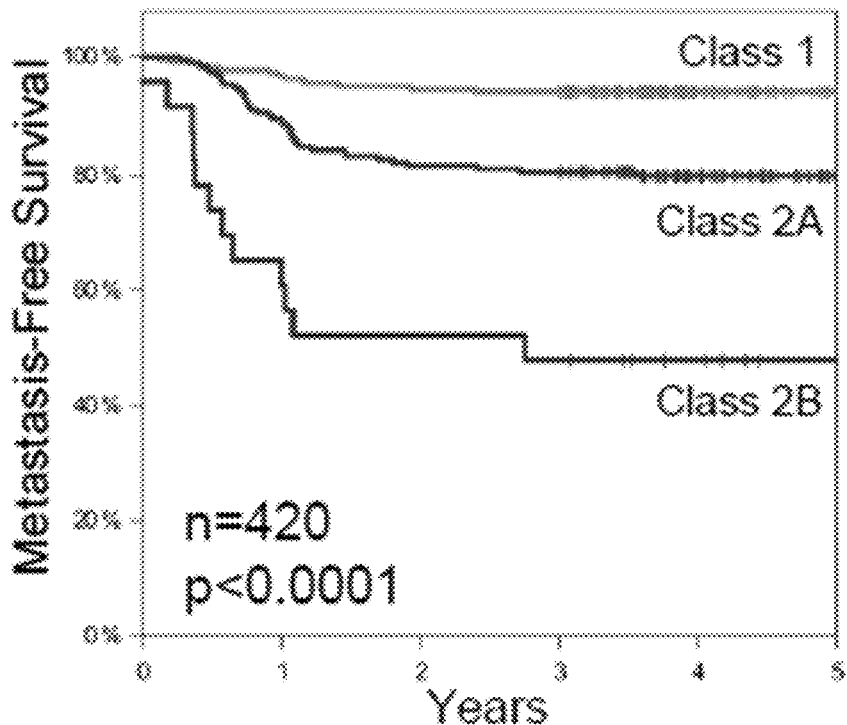
FIG. 18A shows that the 40-GEP test accurately stratified patients based on risk for regional or distant metastasis.

The 40-GEP test accurately stratified patients based on risk for regional or distant metastasis (FIG. 18A). Of the 420 cases included in the study, 212 were identified as Class 1 (low risk), 185 as Class 2A (moderate risk), and 23 as Class 2B (high risk), with metastasis rates of 6.6%, 20.0%, and 52.2%, respectively, and Kaplan-Meier 3-year MFS rates of 93.9%, 80.5% and 47.8% (log-rank, p<0.001, FIG. 18A).

TABLE 17

Demographics and clinical characteristics of the study cohort (n = 420)
Clinical Validation Cohort (n = 420)

| Characteristics | All (n = 420) | Non-Metastatic (n = 357) | Regional/distant Met (n = 63) | p Value |
|---|---|---|---|---|
| Age: Median years (range) | 71 (34-95) | 71 (34-95) | 70 (44-90) | ns |
| Male sex | 308 (73.3%) | 253 (70.9%) | 55 (87.3%) | 0.007 |
| Caucasian | 417 (99.3%) | 355 (99.4%) | 62 (98.4%) | ns |
| Immunosuppressed* | 103 (24.5%) | 83 (23.2%) | 20 (31.7%) | ns |
| Located on H&N | 278 (66.2%) | 224 (62.7%) | 54 (85.7%) | 0.0002 |
| Ear | 64 (15.2%) | 53 (14.8%) | 11 (17.5%) | |
| Lip | 25 (6.1%) | 17 (4.8%) | 8 (12.7%) | |
| Scalp | 56 (13.3%) | 40 (11.2%) | 16 (25.4%) | |
| Tumor diameter: Mean cm (StDev)** | 2.01 (±1.86) | 1.84 (±1.67) | 3.11 (±2.52) | <0.0001 |
| Tumor thickness: Mean mm (StDev)*** | 4.34 (±6.45) | 3.72 (±6.63) | 7.71 (±4.07) | <0.0001 |
| Poorly differentiated | 58 (13.8%) | 36 (10.1%) | 22 (34.9%) | <0.0001 |
| PNI present (≥0.1 mm) | 7 (1.7%) | 5 (1.4%) | 2 (3.2%) | <0.0001 |
| present (<0.1 mm) | 22 (5.2%) | 12 (3.4%) | 10 (15.9%) | |
| present (unknown) | 24 (5.7%) | 17 (4.8%) | 7 (11.1%) | |
| not present | 367 (87.4%) | 323 (90.5%) | 44 (69.8%) | |

TABLE 17-continued

Demographics and clinical characteristics of the study cohort (n = 420)
Clinical Validation Cohort (n = 420)

| Characteristics | All (n = 420) | Non-Metastatic (n = 357) | Regional/distant Met (n = 63) | p Value |
|---|---|---|---|---|
| Invasion beyond subcutaneous fat | 51 (12.1%) | 34 (9.5%) | 17 (27.0%) | <0.0001 |
| Definitive surgery MMS# | 333 (79.3%) | 291 (81.5%) | 42 (66.7%) | 0.023 |
| NCCN High risk | 407 (96.9%) | 345 (96.6%) | 62 (98.4%) | ns |

Data analyzed using Chi-square test or Kruskal-Wallis F test as appropriate for variable type.
Abbreviations:
H&N, head and neck;
StDev, standard deviation;
PNI, perineural invasion;
MMS, Mohs micrographic surgery;
NCCN, National Comprehensive Cancer Network.
*86 of 103 immunosuppressed patients were transplant patients.
**Tumor diameter reported (n = 393).
***Tumor thickness reported (n = 123).
MMS or wide local excision (n = 415) with 2 cases not having additional surgery beyond biopsy, 3 with unknown definitive surgery.

Incorporation of the 40-GEP with Clinicopathologic Factor-Based Risk Assessment

Figure 18B:
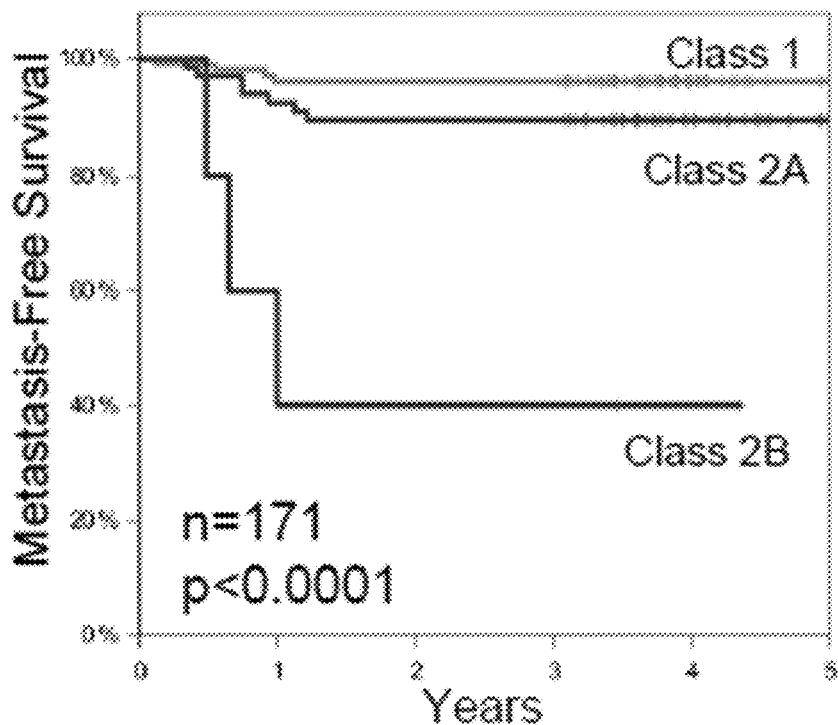
FIG. 18B shows that incorporating the 40-GEP test results identified Class 1 subsets with metastasis rates of 4.0% for 1 risk factor (>50% lower than pre-40-GEP testing).
Figure 18C:
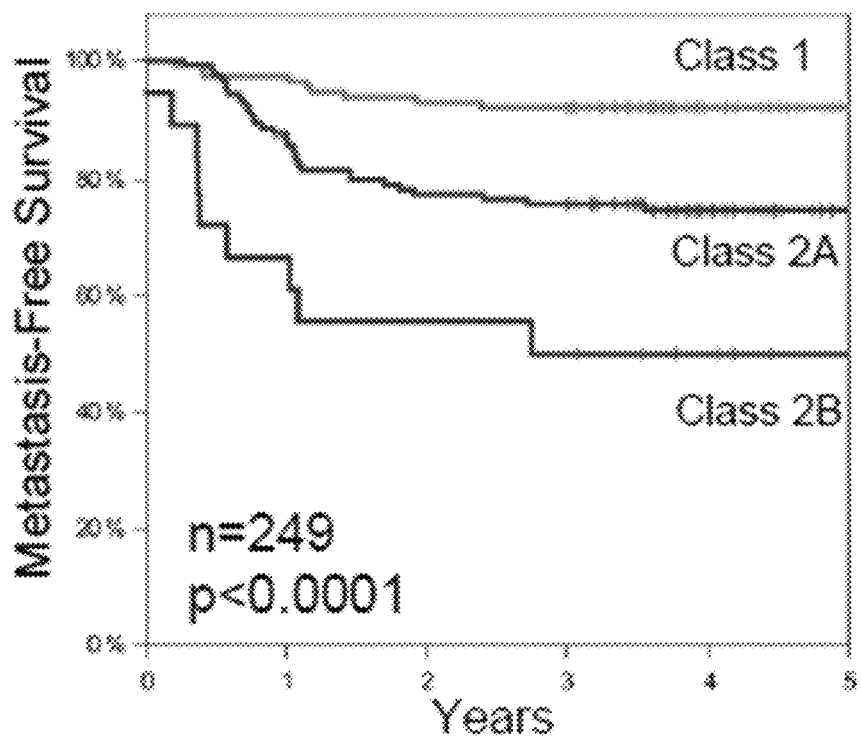
FIG. 18C shows that incorporating the 40-GEP test results identified Class 1 subsets with metastasis rates of 9.0% for ≥2 risk factors (>50% lower than pre-40-GEP testing).
Figure 19B:
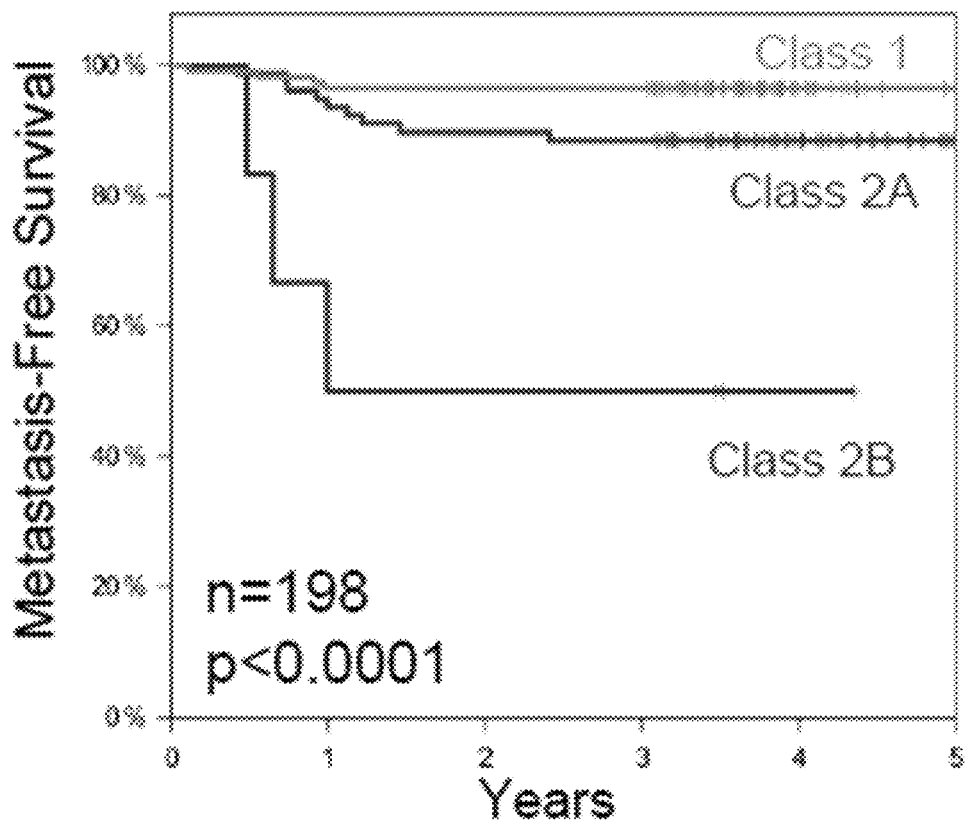
FIG. 19B shows that when only including cases classified as NCCN high risk (n=407, 62 metastatic cases), stratification of risk by the 40-GEP in line with that of the full cohort was observed and identified Class 1 subsets with metastasis rates of 3.5% for 1 risk factor.
Figure 19C:
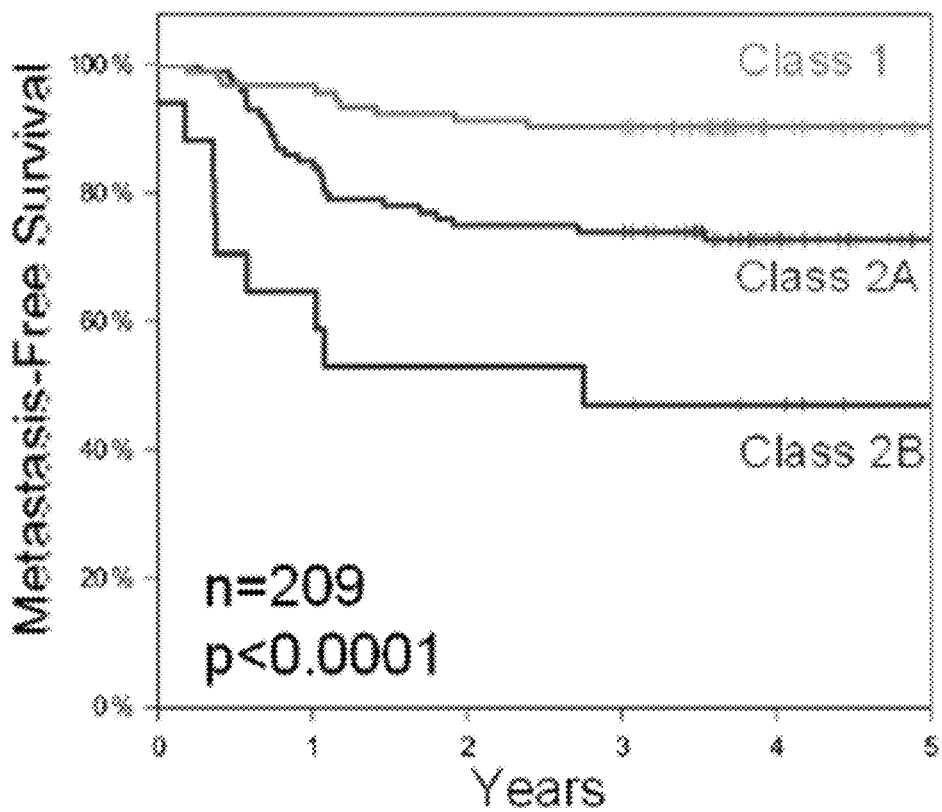
FIG. 19C shows that when only including cases classified as NCCN high risk (n=407, 62 metastatic cases), stratification of risk by the 40-GEP in line with that of the full cohort was observed and identified Class 1 subsets with metastasis rates of 10.9% for ≥2 risk factors.

To determine the impact of molecular prognostication on existing risk assessment strategies, subgroups composed of molecular class and combinations of risk factors were interrogated by Kaplan-Meier and regression analysis. First, cases were assessed for total count of risk factors, as determined by NCCN risk criteria or Mohs AUC (as described in the methods, Table 16), and then binned into two groups: those with 1 risk factor (n=171) and those with >2 risk factors (n=249) (FIGS. 18B and 18C). The results demonstrate that there was a direct relationship between risk factor count and overall metastasis rates. The metastasis rate for those with 1 risk factor was 8.2% (versus 15.0% for the whole cohort) compared to 19.7% for cases with >2 risk factors. Incorporating the 40-GEP test results identified Class 1 subsets with metastasis rates of 4.0% and 9.0% for 1 and ≥2 risk factors, respectively (>50% lower than pre-40-GEP testing; FIGS. 18B and 18C). Combining Class 2A results with risk factors identified subsets with moderately higher metastasis rates relative to pre-40-GEP testing (10.8% and 25.0% for 1 and ≥2 factors, respectively). Regardless of risk factor count, Class 2B metastasis rates were ≥50% (more than double the rate for each subset prior to molecular prognostication). These findings were supported by statistically significant differences in 3-year MFS rates for the cohort and corresponding changes for each subset (FIGS. 18A, 18B, and 18C). Similar changes in metastasis rates were observed when cases were binned by NCCN risk factor count or BWH T stage, and assessed by 40-GEP results (Table 18). When only including cases classified as NCCN high risk (n=407, 62 metastatic cases), stratification of risk by the 40-GEP in line with that of the full cohort was observed (FIG. 19A-19C).

TABLE 18

Metastasis rates by 40-GEP and NCCN risk factor count or BWH T-stage

| 40-GEP | ≤1 NCCN Factors | | ≥2 NCCN Factors | |
|---|---|---|---|---|
| Result | n | Met rate | n | Met rate |
| Class 1 | 120 | 3.3% | 92 | 10.9% |
| Class 2A | 85 | 11.8% | 100 | 27.0% |
| Class 2B | 6 | 50.0% | 17 | 52.9% |
| Pre-Test | 211 | 8.1% | 209 | 22.0% |

| 40-GEP | T1/T2a BWH T-stage | | T2b/T3 BWH T-stage | |
|---|---|---|---|---|
| Result | n | Met rate | n | Met rate |
| Class 1 | 193 | 5.7% | 19 | 15.8% |
| Class 2A | 155 | 16.8% | 30 | 36.7% |
| Class 2B | 16 | 43.8% | 7 | 71.4% |
| Pre-Test | 364 | 12.1% | 56 | 33.9% |

Next, to understand how individual factors contribute to metastatic risk, factors with best-supported evidence for association with metastasis and molecular prognostication by the 40-GEP were assessed by Cox regression analyses (Table 19). Using univariate analysis, the risk of metastasis for Class 2A and 2B results was 3.22- and 11.61-fold greater, respectively, than that for Class 1 results (p<0.001). The presence of poor differentiation, PNI, and deep invasion (i.e., beyond the subcutaneous fat, depth>6 mm, or Clark level V) were significant risk factors for metastasis, with HRs of 3.93, 3.28, and 3.11, respectively (p<0.001). Tumor diameter was also predictive of metastatic risk with an HR of 1.15 per cm increase (p<0.001). Despite prior support for immunosuppression as a prognostic risk factor, this variable was not statistically significant in this cohort.

TABLE 19

Univariate and multivariate Cox regression analyses for risk of metastasis in validation cases with common risk factors for poor outcomes in cSCC

| Risk Factor | n | Univariate Cox Regression | | Multivariate Cox Regression* | |
|---|---|---|---|---|---|
| | | Hazard Ratio (95% CI) | p value | Hazard Ratio (95% CI) | p value |
| 40-GEP Result | | | | | |
| Class 1 | 212 | 1.00 (—) | — | 1.00 (—) | — |
| Class 2A | 185 | 3.22 (1.74-5.95) | <0.001 | 2.33 (1.20-4.53) | 0.013 |
| Class 2B | 23 | 11.61 (5.36-25.15) | <0.001 | 6.86 (2.73-17.22) | <0.001 |
| Clinicopathological Risk Factors | | | | | |
| Poor Differentiation | 58 | 3.93 (2.34-6.60) | <0.001 | 2.29 (1.21-4.33) | 0.011 |
| Perineural Invasion** | 53 | 3.28 (1.41-14.36) | <0.001 | 1.22 (0.58-2.59) | ns |
| Deep Invasion[#] | 72 | 3.11 (1.86-5.20) | <0.001 | 2.05 (1.04-4.04) | 0.039 |
| Tumor Diameter[##] | N/A | 1.15 (1.08-1.22) | <0.001 | 1.07 (0.97-1.17) | ns |
| Immunosuppressed | 103 | 1.46 (0.86-2.49) | ns | — | — |

*n = 393, 54 events, excluding cases without tumor diameter reported;
**Perineural invasion was considered positive regardless of nerve caliber.
[#]Deep invasion: beyond the subcutaneous fat, depth > 6 mm or Clark level V;
[##]Tumor diameter: continuous variable per cm;
ns: not statistically significant;
N/A: not applicable.

When a multivariate model was generated using factors found to be significant in univariate analysis, only 40-GEP results, poor differentiation, and deep invasion were independent factors for metastatic risk (Table 19). In this multivariate analysis, similar HRs were observed for a Class 2A result, poor differentiation, and deep invasion (2.33, 2.29, and 2.05, respectively; p<0.05); whereas, a 40-GEP Class 2B result was found to have the greatest independent prognostic value (HR, 6.86; p<0.001). Based on MFS rates, as well as Cox regression analyses, incorporation of 40-GEP results with clinicopathologic risk factor-based assessment improved patient metastasis risk stratification.

Discussion

This Example demonstrates that molecular prognostication, in conjunction with patient and tumor characteristics, increases accuracy and reproducibility of risk assessment for patients with cSCC. The 40-GEP test was further validated as a stand-alone clinical assay to identify cSCC tumors at low (Class 1), moderate (Class 2A), and high (Class 2B) risk for metastasis within 3 years of diagnosis, the time by which most metastatic events occur. This Example also further validates the algorithm for determining metastatic risk with improved accuracy metrics relative to currently available staging systems, validates the test under SOPs implemented for clinical testing, and demonstrates impactful incorporation with clinicopathologic risk factor-based assessment.

Current prognostication suffers from low accuracy, stemming from lack of standardization in reporting and subjectivity during histopathological assessment, and, importantly, failure to capture biological risk at the molecular level. For example, differentiation was removed from AJCC8 T staging as the definitions of well, moderate, and poor differentiation were deemed too inconsistent between centers, limiting its clinical application. While tumor depth/invasion is a well-accepted risk factor for metastasis, how this variable should be captured and what degree of invasion is needed to be considered high risk is debated. Additionally, the rarity of large nerve PNI20 (1.7% in this study) may limit its widespread utility for identifying high-risk patients. These caveats to clinical utility likely contribute to the poor PPV associated with traditional risk assessment, supporting the need for objective and consistent molecular tools to assess tumor biology.

Integration of molecular prognostication into risk assessment can mitigate limitations of assessment based on clinicopathologic factors alone. Findings from this Example demonstrate the 40-GEP complements clinicopathologic risk assessment. In a multivariate model with commonly-utilized high-risk factors, the 40-GEP provided independent prognostic value. Class 2B and Class 2A results were higher and equivalent indicators, respectively, of risk for metastasis relative to other significant factors (poor differentiation and deep invasion, Table 19), indicating the 40-GEP can further stratify patients. Both deep invasion and tumor diameter were significant risk factors in univariate, but tumor diameter was not significant in multivariate analysis, suggesting directionality of growth (i.e., invasive behavior rather than surface spread) is an important distinction. Perineural invasion was also only statistically significant in univariate analysis, consistent with prior studies showing PNI loses significance in analysis with other high-risk factors. In this high-risk cohort, immunosuppression did not reach statistical significance for association with metastasis, despite the fact that it has been strongly associated with risk for additional cSCC lesions and poor outcomes. The archival nature of samples and possible underreporting of high-risk factors are potential limitations of this study. However, the cohort represents a high-risk cSCC population (15% metastasis, 97% NCCN high-risk) and reflects current clinical pathology practices.

Incorporation of molecular prognostication with clinicopathologic factors has improved risk stratification in multiple cancer types. The 40-GEP test, along with clinicopathologic risk factor-based assessment, can identify a group of cSCC patients, in a high-risk cohort, with metastasis rates similar to the general cSCC population (Class 1 40-GEP with 1 risk factor). Even with ≥2 risk factors, the metastasis rate for patients with a Class 1 result was below 10%, (>50% lower than the rate for the whole cohort, pre-40-GEP). Patients identified by the 40-GEP as highest risk for metastasis (Class 2B) consistently had metastasis rates>50%, regardless of having 1 or >2 risk factors. Thus, inclusion of molecular prognostication improved risk stratification via a more objective and standardized risk assessment, and incorporating molecular tools into cSCC patient risk assessment, could lead to more personalized and risk-appropriate pathways to improve patient management and outcomes.

All references cited in this application are expressly incorporated by reference herein.

What is claimed is:

1. A method for treating a patient with a cutaneous squamous cell carcinoma (cSCC) tumor, the method comprising:
   (a) obtaining a diagnosis identifying a risk of metastasis in a cSCC tumor sample from the patient, wherein the diagnosis was obtained by:
      (1) determining the expression level of 34 genes in a gene set; wherein the 34 genes in the gene set are: ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839;
      (2) comparing the expression levels of the 34 genes in the gene set from the cSCC tumor sample to the expression levels of the 34 genes in the gene set from a predictive training set to generate a probability score of the risk of metastasis;
      (3) providing an indication as to whether the cSCC tumor has a low risk to a high risk of metastasis based on the probability score generated in step (2); and
      (4) identifying that the cSCC tumor has a high risk of metastasis based on the probability score in combination with at least one risk factor and diagnosing the cSCC tumor as having a high risk of metastasis; and
   (b) administering to the patient an aggressive treatment to increase relapse free survival of the patient when the determination is made in the affirmative that the patient has a cSCC tumor with a high risk of metastasis, wherein the aggressive treatment is one or more of radiation therapy, chemoradiation, chemotherapy, regional limb therapy, surgery, systemic therapy, or immunotherapy.

2. The method of claim 1, further comprising performing a resection of the cSCC tumor when the determination is made in the affirmative that the patient has a cSCC tumor with a high risk of metastasis.

3. The method of claim 1, wherein the expression level of each gene in a gene set is determined by reverse transcribing the isolated mRNA and measuring a level of fluorescence for each gene in the gene set by a nucleic acid sequence detection system following RT-PCR.

4. The method of claim 1, wherein the cSCC tumor sample is obtained from a formalin-fixed, paraffin embedded sample.

5. The method of claim 1, wherein the probability score is between 0 and 1, and wherein a value of 1 indicates a higher probability of metastasis than a value of 0.

6. The method of claim 1, wherein the probability score is a bimodal, two-Class analysis, wherein a patient having a value of between 0 and 0.499 is designated as Class 1 (low risk) and a patient having a value of between 0.500 and 1.00 is designated as Class 2 (high risk).

7. The method of claim 1, wherein the probability score is a tri-modal, three-Class analysis, wherein patients are designated as Class 1 (low risk), Class 2A (moderate risk), or Class 2B (high risk).

8. The method of claim 1, wherein the gene set further comprises at least one control gene, wherein the at least one control gene is selected from the group consisting of BAG6, KMT2D/MLL2, MDM2, FXR1, KMT2C, MDM4, VIM, and NF1B.

9. The method of claim 8, wherein the control genes are MDM2, KMT2D, BAG6, FXR1, MDM4, and KMT2C.

10. The method of claim 1, wherein the at least one risk factor is selected from tumor size, tumor location, immune status, perineural involvement (PNI), depth of invasion, differentiation, histological subtype, and lymphovascular invasion.

11. A method of treating a patient with a cutaneous squamous cell carcinoma (cSCC) tumor, the method comprising administering an aggressive cancer treatment regimen to the patient to increase relapse free survival of the patient, wherein the aggressive treatment is one or more of radiation therapy, chemoradiation, chemotherapy, regional limb therapy, surgery, systemic therapy, or immunotherapy, and wherein the patient has a cSCC tumor with a moderate risk (Class 2A), or a high risk (Class 2B) as generated by comparing the expression levels of 34 genes, in combination with at least one risk factor, wherein the 34 genes are ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839, from the cSCC tumor with the expression levels of the same 34 genes ACSBG1, ALOX12, APOBEC3G, ATP6V0E2, BBC3, BHLHB9, CEP76, DUXAP8, GTPBP2, HDDC3, ID2, LCE2B, LIME1 (ZGPAT), LOC100287896, LOC101927502, MMP10, MRC1, MSANTD4, NFASC, NFIC, PDPN, PI3, PLS3, RCHY1, RNF135, RPP38, RUNX3, SLC1A3, SPP1, TAF6L, TFAP2B, ZNF48, ZNF496, and ZNF839 from a predictive training set.

12. The method of claim 11, wherein the moderate risk (Class 2A) cSCC tumor has about a 10-49% risk for metastasis, and the high risk (Class 2B) cSCC tumor has about a 50-100% risk for metastasis.

13. The method of claim 11, wherein the gene set further comprises at least one control gene, wherein the at least one control gene is selected from the group consisting of BAG6, KMT2D/MLL2, MDM2, FXR1, KMT2C, MDM4, VIM, and NF1B.

14. The method of claim 13, wherein the control genes are MDM2, KMT2D, BAG6, FXR1, MDM4, and KMT2C.

15. The method of claim 11, wherein the at least one risk factor is selected from tumor size, tumor location, immune status, perineural involvement (PNI), depth of invasion, differentiation, histological subtype, and lymphovascular invasion.

16. The method of claim 1, wherein the radiation therapy is (a) adjuvant therapy, (b) neoadjuvant therapy, or (c) both adjuvant therapy and neoadjuvant therapy.

17. The method of claim 11, wherein the radiation therapy is (a) adjuvant therapy, (b) neoadjuvant therapy, or (c) both adjuvant therapy and neoadjuvant therapy.

* * * * *